(12) United States Patent
Kurihara et al.

(10) Patent No.: US 6,660,718 B1
(45) Date of Patent: Dec. 9, 2003

(54) 3-MODIFIED LEUCOMYCIN DERIVATIVES

(75) Inventors: Ken-ichi Kurihara, Kawasaki (JP); Takeshi Furuuchi, Yokohama (JP); Takuji Yoshida, Yokohama (JP); Tomoaki Miura, Yokohama (JP); Keiichi Ajito, Kawasaki (JP)

(73) Assignee: Meiji Seika Kaisha, Ltd., Tokyo (JP)

(*) Notice: Subject to any disclaimer, the term of this patent is extended or adjusted under 35 U.S.C. 154(b) by 0 days.

(21) Appl. No.: 09/980,113

(22) PCT Filed: May 31, 2000

(86) PCT No.: PCT/JP00/03507

§ 371 (c)(1), (2), (4) Date: Nov. 30, 2001

(87) PCT Pub. No.: WO00/73317

PCT Pub. Date: Dec. 7, 2000

(30) Foreign Application Priority Data

Jun. 1, 1999 (JP) .................... 11-153587

(51) Int. Cl.$^7$ .................... C07H 17/08; A61K 31/70
(52) U.S. Cl. .................... 514/30; 536/7.1
(58) Field of Search .................... 536/7.1; 514/30

(56) References Cited

U.S. PATENT DOCUMENTS 5,407,918 A * 4/1995 Ajito et al. .................... 514/30

OTHER PUBLICATIONS

R. Okamoto et al. J. Ferment. Technol., 57 519, 1979.
H.A. Kirst, Journal of Antimicrobial Chemotherapy, 28, 787, 1991.
Shomura et al., J. Pharmaceutical Society of Japan 102, 781, 1982.
K. Ajito et al., J Anibiot., 50, 92, 1997.
K. Kurihara et al., J. Antibiot., 50, 32, 1997.
Inoue, Annual Report of Meiji Seika, 13, 100, 1973.
A. Inoue et al., J. Anitiot., 36 442, 1983.
Omura et al., Japanese Patent Unexamined Publication (Kokai) No. 61–126096 with an English excerpt (Patent Abstracts of Japan).
R.F. Heck, Org. Reactions, 27, 345 (1982).
K. Ajito et al., J. Antibiot., 50, 366, 1997.
K. Kurihara et al., J. Antibiot, 51, 771, 1998.
S. Omura et al., J. Antibiot., 34, 1577, 1981.

* cited by examiner

*Primary Examiner*—Elli Peselev
(74) *Attorney, Agent, or Firm*—Sughrue Mion, PLLC

(57) ABSTRACT

A compound represented by the following general formula (I) or a salt thereof:

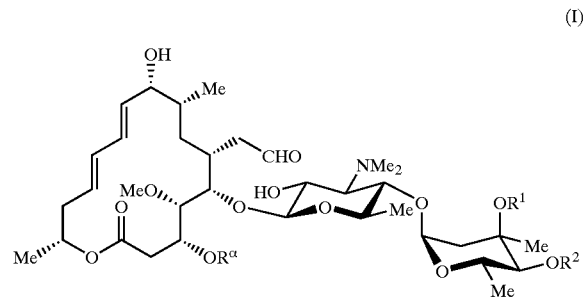

wherein $R^\alpha$ represents a C1–C10 alkyl group, a C3–C10 alkenyl group, a C7–C15 aralkyl group, a quinolinylalkyl group, a quinolinylalkenyl group, a C2–C10 alkylcarbonyl group, a C7–C15 aralkylcarbonyl group, a C4–C7 cycloalkylcarbonyl group, benzoyl group, an imidazolylcarbonyl group and the like; $R^1$ represents hydrogen atom, a C1–C10 alkyl group, or a C2–C10 alkylcarbonyl group; and $R^2$ represents hydrogen atom, a C1–C10 alkyl group, or a C2–C10 alkylcarbonyl group, provided that the compound wherein $R^\alpha$ represents a C2–C10 alkylcarbonyl group and both of $R^1$ and $R^2$ represent a C1–C10 alkyl group is excluded.

13 Claims, 1 Drawing Sheet

3-MODIFIED LEUCOMYCIN DERIVATIVES

This application is a 371 of PCT/JP00/03507 filed May 31, 2000.

TECHNICAL FIELD

The present invention relates to novel leucomycin derivatives effective against Gram-positive bacteria.

BACKGROUND ART

Macrolide antibiotics is a class of clinically important antibacterial agents that generally have low toxicity and can be orally administered. They are basically classified into 14-membered ring macrolides and 16-membered ring macrolides based on the structural atom number of the lactone ring as an aglycone. Those frequently used clinically among the 16-membered ring macrolides are leucomycin and derivatives thereof, and studies have been made so far by many research groups to improve their efficacy. The 16-membered ring macrolide antibiotics are known to give a lower blood level than the 14-membered ring macrolides (R. Okamoto et al. J. Ferment. Technol., 57, 519, 1979), and it is one of important objects to eliminate this drawback (H. A. Kirst, Journal of Antimicrobial Chemotherapy, 28, 787, 1991).

Many studies have been made to improve the blood level. Recently, the inventors of the present invention focused their researches to the neutral saccharide moiety of the leucomycin-type 16-membered ring macrolides, which is one of metabolic sites (Shomura et al., J. Pharmaceutical Society of Japan, 102, 781, 1982), and they created various leucomycin derivatives in which said moiety was converted into a neutral saccharide that was hardly metabolized. They revealed that the derivatives had desired superior pharmacokinetics in experiments using animals (K. Ajito et al., J. Antibiot., 50, 92, 1997 and K. Kurihara et al., J. Antibiot., 50, 32, 1997).

Through various studies mainly from a viewpoint of pharmacokinetics or antibacterial activity, it is known that pharmacokinetics of the leucomycin type 16-membered ring macrolides may significantly vary depending on a structural difference, i.e., whether the hydroxyl group at 3-position of the lactone ring is free or acylated, and that those having an acyl group generally give better results in blood level in vivo (Inoue, Annual Report of Meiji Seika, 13, 100, 1973).

Spiramycin (SPM) is also a 16-membered ring macrolide having 17-demetyl-17-formylplatenolide II as a basic aglycone like leucomycin. SPMs also have different stabilities in blood serum depending on a structure at 3-position, i.e., SPM I having a free 3-hydroxyl group is less stable in rat blood serum than SPM II or SPM III which has an acyl group at the 3-position. As one of rat major metabolites of SPM I, a metabolite is reported in which the 3-hydroxyl group and the aldehyde portion form a hemiacetal and thus the lactone ring is cleaved (A. Inoue et al., J. Antibiot., 36, 442, 1983).

Both of leucomycins and SPMs have a unique chemical property that the 3-hydroxyl group and the 18-aldehyde portion easily form a hemiacetal under a basic condition. Assuming that this chemical property is attributable to the fact that they have the same basic aglycone moiety, it is presumed that leucomycins having a free hydroxyl group at the 3-position have the same in vivo behavior as that of SPM I.

On the basis of the above facts, it is also presumed that a free hydroxyl group at the 3-position is disadvantageous in the leucomycin-type 16-membered ring macrolides from viewpoints of stability and metabolism, and improvements of stability and efficacy is expected by a structural conversion at that position.

As for SPM I, compounds are reported which are derived by introducing methyl group at the hydroxyl group at the 3-position of SPM I derivatives of which 3"- and 4"-positions are diacylated. However, since the publication fails to give a result of direct comparison of the SPM I derivatives as a raw material of which 3"- and 4"-positions were diacylated and the methylated derivative, contribution of the methylation of 3-hydroxyl group to the activity was identified (Omura et al., Japanese Patent Publication (Kokai) No. 61-126096).

Whilst as for 16-membered ring macrolides other than SPM, no compound is known in which hydroxyl group at the 3-position is alkylated (for example, methylated). Therefore, it is impossible to predict activity and stability of compounds with an alkylated hydroxyl group at the 3-position which is derived from the natural and non-natural leucomycin-type 16-membered ring macrolides having free hydroxyl group at the 3-position.

Further, from a viewpoint of inhibition of the aforementioned hemiacetal formation of the hydroxyl group at the 3-position and the aldehyde moiety at the 18-position, epi-type derivatives wherein the hydroxyl group at the 3-position of the natural-type compounds is inverted are expected to be effective for inhibition of the hemiacetal formation, since the inversion of the hydroxyl group at the 3-position may have a reaction site of the hydroxyl group alienate from the 18-aldehyde portion. However, no 3-epi-type derivative of the 16-membered ring macrolide is known in which the hydroxyl group at the 3-position is inverted, and therefore, activity of such compound is also unpredictable.

DISCLOSURE OF THE INVENTION

The present invention mainly relates to useful novel leucomycin derivatives and pharmacologically acceptable salts thereof.

The inventors of the present invention conducted various studies to solve the aforementioned problems, and synthesized novel leucomycin derivatives by using leucomycin-type 16-membered ring macrolides having a free hydroxyl group at the 3-position as starting materials and alkylating the hydroxyl group at the 3-position. At the same time, they established a method for alkylating the hydroxyl group at the 3-position regardless of a side chain structure modifying the 3"- and 4"-hydroxyl groups of the mycarose as the neutral saccharide moiety. In addition, they found that the Heck reaction (R. F. Heck, Org. Reactions, 27, 345 (1982)) progressed on the 3-O-alkenyl derivatives obtained by the above method, thereby various side chains can be introduced into the derivatives.

Furthermore, they successfully created novel 3-epi type leucomycin derivatives having a non-natural type 3-hydroxyl group by producing key intermediate compounds which were obtained by efficiently oxidizing the free hydroxyl group at the 3-position of the natural-type leucomycins.

As a result, the inventors found that the derivatives provided as the compounds of the present invention had enhanced activity and higher stability in blood plasma compared with the conventional leucomycin analogues, and on the basis of the finding, they achieved the present invention. In the leucomycin-type 16-membered ring macrolides, no compound is known that apparently has generally enhanced antibacterial activity attributable to an introduced atomic group, except for the report made by the inventors of the present invention (K. Ajito et al., J. Antibiot., 50, 366, 1997 and K. Kurihara et al., J. Antibiot., 51, 771, 1998).

The present invention thus provides compounds represented by the following general formula (I):

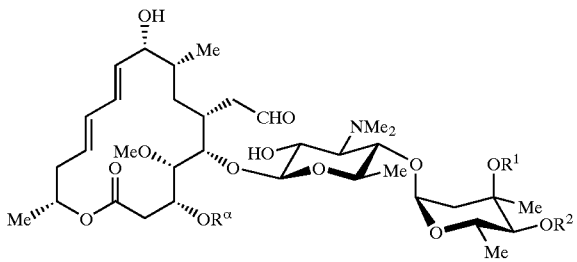

(I)

[in the formula, $R^\alpha$ represents a C1–C10 alkyl group, a C3–C10 alkenyl group, a C7–C15 aralkyl group, a quinolinylalkyl group, a quinolinylalkenyl group, a C2–C10 alkylcarbonyl group, a C7–C15 aralkylcarbonyl group, a C4–C7 cycloalkylcarbonyl group, benzoyl group, an imidazolylcarbonyl group, a quinolinylcarbonyl group, an N-alkylaminocarbonyl group, an N,N-dialkylaminocarbonyl group, or an N-aralkylaminocarbonyl group; $R^1$ represents hydrogen atom, a C1–C10 alkyl group, or a C2–C10 alkylcarbonyl group; and $R^2$ represents hydrogen atom, a C1–C10 alkyl group, or a C2–C10 alkylcarbonyl group provided that a compound wherein $R^\alpha$ represents a C2–C10 alkylcarbonyl group and both of $R^1$ and $R^2$ represent a C1–C10 alkyl group] and salts thereof.

According to the second aspect of the present invention, there are provided compounds represented by the following general formula (II):

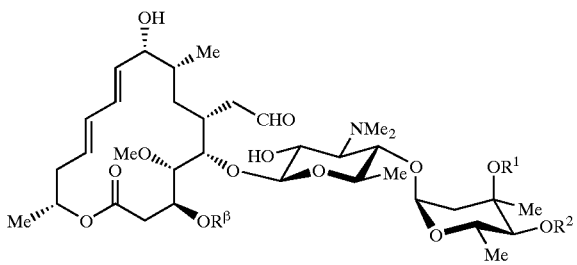

(II)

[in the formula, $R^\beta$ represents hydrogen atom, a C2–C10 alkylcarbonyl group, a C4–C7 cycloalkylcarbonyl group, a C7–C15 aralkylcarbonyl group, benzoyl group, a pyridinylcarbonyl group, an imidazolylcarbonyl group, a quinolinylcarbonyl group, an N,N-dialkylaminocarbonyl group, an N-alkylaminocarbonyl group, or an N-aralkylaminocarbonyl group; $R^1$ represents hydrogen atom, a C1–C10 alkyl group, or a C2–C10 alkylcarbonyl group; and $R^2$ represents hydrogen atom, a C1–C10 alkyl group, or a C2–C10 alkylcarbonyl group] and salts thereof.

According to further aspect of the present invention, there are provided compounds and salts thereof that are preferably used for the manufacture of the compounds of the aforementioned general formula (I) and salts thereof. That is, the present invention provides compounds represented by the following general formula (III):

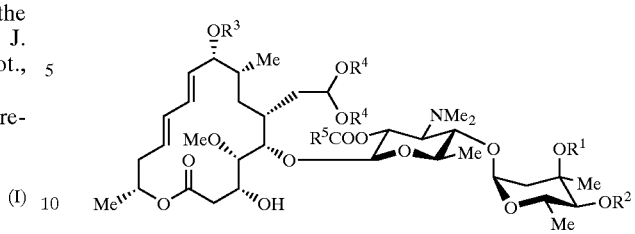

(III)

[in the formula, $R^1$ represents hydrogen atom, a C1–C10 alkyl group or a C2–C10 alkylcarbonyl group, $R^2$ represents hydrogen atom, a C1–C10 alkyl group or a C2–C10 alkylcarbonyl group, $R^3$ represents triethylsilyl group, triisopropylsilyl group, triphenylsilyl group, tribenzylsilyl group, dimethylisopropylsilyl group, t-butyldimethylsilyl group or t-butyldiphenylsilyl group, $R^4$ represents a C1–C5 alkyl group, and $R^5$ represents a C1–C5 alkyl group] and salts thereof.

According to still further aspect of the present invention, there are provided compounds that are preferably used for the manufacture of the compounds of the aforementioned general formula (II) and salts thereof. That is, the present invention provides compounds represented by the following general formula (IV):

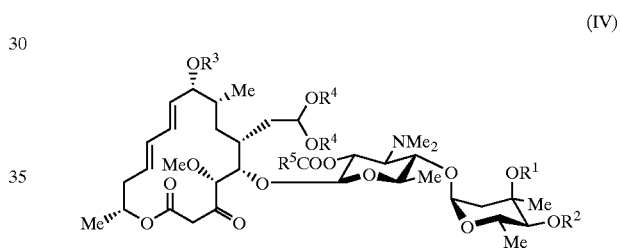

(IV)

[in the formula, $R^1$ represents hydrogen atom, a C1–C10 alkyl group, or a C2–C10 alkylcarbonyl group, $R^2$ represents hydrogen atom, a C1–C10 alkyl group or a C2–C10 alkylcarbonyl group, $R^3$ represents triethylsilyl group, triisopropylsilyl group, triphenylsilyl group, tribenzylsilyl group, dimethylisopropylsilyl group, t-butyldimethylsilyl group or t-butyldiphenylsilyl group, $R^4$ represents a C1–C5 alkyl group, and $R^5$ represents a C1–C5 alkyl group] and salts thereof.

The present invention also provides medicaments comprising a compound represented by the aforementioned general formula (I) or a pharmaceutically acceptable salt thereof as an active ingredient, and medicaments comprising a compound represented by the aforementioned general formula (II) or a pharmaceutically acceptable salt thereof as an active ingredient. These medicaments are useful for therapeutic and/or prophylactic treatment of infectious diseases, particularly therapeutic and/or prophylactic treatment of infectious diseases caused by Gram-positive bacteria. The present invention also provides antibacterial agents comprising the compounds represented by the aforementioned general formula (I) or pharmaceutically acceptable salts thereof as an active ingredient and antibacterial agents comprising the compounds represented by the aforementioned general formula (II) or pharmaceutically acceptable salts thereof as an active ingredient. These antibacterial agents are preferably used as antibacterial agents against Gram-positive bacteria.

The present invention also provides use of the compounds represented by the aforementioned general formula (I) or pharmaceutically acceptable salts thereof for the manufacture of the aforementioned medicaments, and use of the compounds represented by the aforementioned general formula (II) or pharmaceutically acceptable salts thereof for the manufacture of the aforementioned medicaments. The present invention further provides methods for therapeutic and/or prophylactic treatment of infectious diseases, which comprises the step of administering a therapeutically and/or prophylactically effective amount of a compound represented by the aforementioned general formula (I) or a pharmaceutically acceptable salt thereof to a mammal including human, and methods for therapeutic and/or prophylactic treatment of infectious diseases, which comprises the step of administering a therapeutically and/or prophylactically effective amount of a compound represented by the aforementioned general formula (II) or a pharmaceutically acceptable salt thereof to a mammal including human.

According to a further aspect of the present invention, there are provided compounds represented by the aforementioned general formula (III) or salts thereof as synthetic intermediates for the manufacture of the compounds represented by the aforementioned general formula (I) or salts thereof, and compounds represented by the aforementioned general formula (IV) or salts thereof as synthetic intermediates for the manufacture of the compounds represented by the aforementioned general formula (II) or salts thereof.

The present invention further provides use of the compounds represented by the aforementioned general formula (III) or salts thereof as synthetic intermediates for the manufacture of the compounds represented by the aforementioned general formula (I) or salts thereof, and use of the compounds represented by the aforementioned general formula (IV) or salts thereof as synthetic intermediates for the manufacture of the compounds represented by the aforementioned general formula (II) or salts thereof.

BEST MODE FOR CARRYING OUT THE INVENTION

Definition

Figure 1:
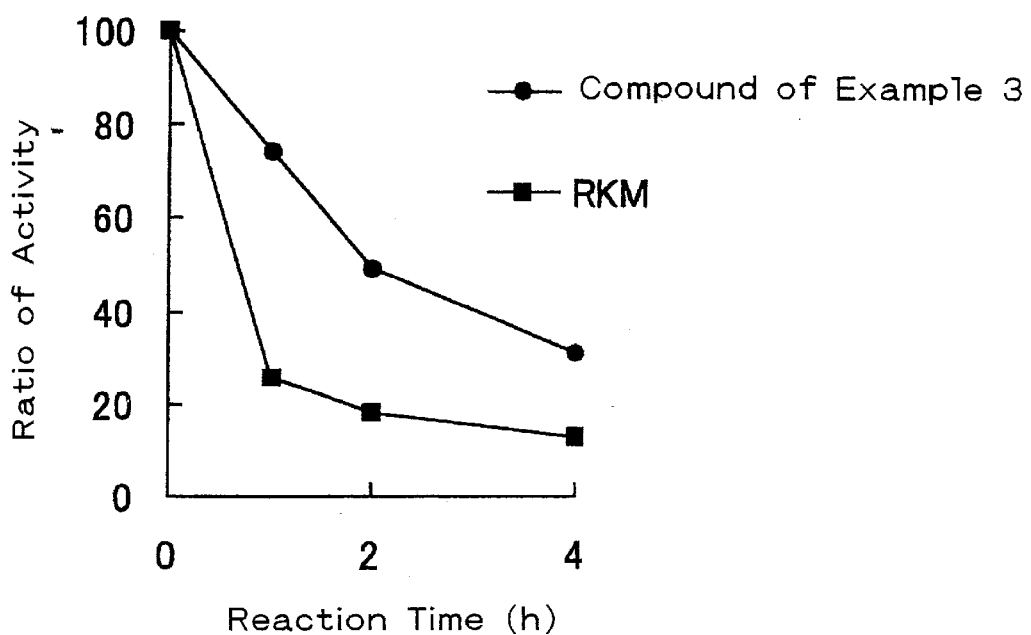
FIG. 1 shows change of antibacterial activity of the compound of the present invention (Example 3) with time in rat blood plasma that demonstrates stability in plasma.

In the specification, an alkyl group or an alkyl moiety of a functional group that contains the alkyl moiety (e.g., an alkoxy group or the like) may be linear, branched, cyclic, or a combination thereof, unless otherwise specifically mentioned, and may preferably be linear or branched. In a functional group containing an alkenyl moiety, the number of double bond contained in the alkenyl moiety is not particularly limited. The alkenyl portion may be linear, branched, cyclic, or a combination thereof, unless otherwise specifically mentioned, and may preferably be linear or branched. A double bond contained in the alkenyl portion may be in either Z-configuration or E-configuration.

In the specification, the aralkyl group means an alkyl group or alkenyl group having a 6- to 14-membered aromatic ring (monocyclic to tricyclic, preferably monocyclic or bicyclic) such as phenyl, 1-naphthyl, 2-naphthyl, biphenyl and 2-anthrylnaphthyl. In the specification, the acyl group preferably means a group selected form the group consisting of a linear or branched C2–C10 alkylcarbonyl group, a C7–C15 aralkylcarbonyl group, a C4–C7 cycloalkylcarbonyl group, imidazol-1-ylcarbonyl-group, benzoyl group, a quinolinylcarbonyl group, an N,N-dialkylaminocarbonyl group, an N-alkylaminocarbonyl group, an N-aralkylaminocarbonyl group, and a pyridinylcarbonyl group. The halogen atom means fluorine, chlorine, bromine or iodine. The hetero atom preferably means nitrogen atom, oxygen atom, or sulfur atom.

Compounds of the General Formulas (I) and (II)

The C1–C10 alkyl group represented by $R^\alpha$ in the general formula (I) and the C1–C10 alkyl group represented by $R^1$ or $R^2$ in the general formula (I) or (II) is preferably a C1–C6 alkyl group.

The C3–C10 alkenyl group represented by $R^\alpha$ may be linear or branched and is preferably a C3–C6 alkenyl group, more preferably allyl group. Examples of the C7–C15 aralkyl group represented by $R^\alpha$ include benzyl group, phenethyl group, and phenylpropyl group, and a phenyl (C1–C5)alkyl group is preferred. The quinolinylalkyl group represented by $R^\alpha$ is preferably a (quinolin-2-yl)-(C1–C5) alkyl group or a (quinolin-3-yl)-(C1–C5) alkyl group. The quinolinylalkenyl group represented by $R^\alpha$ is preferably (quinolin-2-yl)allyl group or (quinolin-3-yl)allyl group.

In the general formula (I) or (II), examples of the C2–C10 alkylcarbonyl group represented by $R^\alpha$, $R^\beta$, $R^1$ or $R^2$ include acetyl group, propionyl group, butyryl group, valeryl group, caprolyl group, enantyl group, isobutyryl group, isovaleryl group, isocaprolyl group and isoenantyl group, and a C2–C7 alkylcarbonyl group is preferred and a C2–C5 alkylcarbonyl group is more preferred.

The C7–C15 aralkylcarbonyl group represented by $R^\alpha$ or $R^\beta$ is preferably a phenyl(C1–C5)alkylcarbonyl group. The C4–C7 cycloalkylcarbonyl group represented by $R^\alpha$ or $R^\beta$ is preferably cyclohexylcarbonyl group. One or more of hydrogen atoms on the benzoyl group represented by $R^\alpha$ or $R^\beta$ may be substituted with a halogen atom, a C1–C4 alkoxy group or nitro group.

The imidazolylcarbonyl group represented by $R^\alpha$ or $R^\beta$ is preferably (imidazol-1-yl)carbonyl group. The quinolinylcarbonyl group represented by $R^\alpha$ or $R^\beta$ is preferably (quinolin-2-yl)carbonyl group or (quinolin-3-yl)carbonyl group. The N-alkylaminocarbonyl group represented by $R^\alpha$ or $R^\beta$ is preferably an N-(C1–C5)alkylaminocarbonyl group, more preferably N-methylaminocarbonyl group. The N,N-dialkylaminocarbonyl group represented by $R^\alpha$ or $R^\beta$ is preferably an N,N-di(C1–C5)alkylaminocarbonyl group, more preferably N,N-dimethylaminocarbonyl group. The N-aralkylaminocarbonyl group represented by $R^\alpha$ or $R^\beta$ is preferably an N-(phenyl-(C1–C5)alkyl)aminocarbonyl group.

The pyridinylcarbonyl group represented by $R^\beta$ in the general formula (II) is preferably (pyridine-4-yl)carbonyl group.

Among the compounds represented by the general formula (I), a class of preferred compounds include those wherein $R^\alpha$ represents a C1–C10 alkyl group, a C3–C10 alkenyl group, a quinolinylalkenyl group, a C7–C15 aralkylcarbonyl group, a benzoyl group, an imidazolylcarbonyl group, a quinolinylcarbonyl group, a C4–C7 cycloalkylcarbonyl group, an N-alkylaminocarbonyl group, an N,N-dialkylaminocarbonyl group, or an N-aralkylaminocarbonyl group, $R^1$ represents hydrogen atom, a C1–C10 alkyl group, or a C2–C10 alkylcarbonyl group, and $R^2$ represents hydrogen atom, a C1–C10 alkyl group, or a C2–C10 alkylcarbonyl group.

A class of more preferred compounds include those wherein $R^\alpha$ represents a C1–C10 alkyl group, a C3–C10 alkenyl group, a quinolinylalkenyl group, an imidazolylcarbonyl group, an N-alkylaminocarbonyl group, an N,N-dialkylaminocarbonyl group, a quinolinylcarbonyl group, or an N-aralkylaminocarbonyl group, $R^1$ represents a C2–C10 alkylcarbonyl group, and $R^2$ represents a C2–C10 alkylcarbonyl group.

Further, another class of more preferred compounds include those wherein $R^\alpha$ represents a C1–C10 alkyl group, $R^1$ represents a C1–C10 alkyl group, and $R^2$ represents a C1–C10 alkyl group.

Furthermore, another class of more preferred compounds include those wherein $R^\alpha$ represents a C1–C10 alkyl group, $R^1$ represents hydrogen atom, and $R^2$ represents a C2–C10 alkylcarbonyl group.

The compounds represented by the aforementioned general formula (I) wherein $R^\alpha$ represents a C2–C10 alkylcarbonyl group and both of $R^1$ and $R^2$ represent a C1–C10 alkyl group are not included in the scope of the present invention.

Among the compounds represented by the general formula (II), a class of preferred compounds include those wherein $R^\beta$ represents hydrogen atom, a C2–C10 alkylcarbonyl group, a C4–C7 cycloalkylcarbonyl group, a C7–C15 aralkylcarbonyl group, a benzoyl group, 2-quinolinylcarbonyl group, 4-pyridinylcarbonyl group, an N-alkylaminocarbonyl group, or an N-aralkylaminocarbonyl group, $R^1$ represents hydrogen atom or a C2–C10 alkylcarbonyl group, and $R^2$ represents hydrogen atom or a C2–C10 alkylcarbonyl group.

More preferred compounds include those wherein $R^\beta$ represents hydrogen atom, a benzoyl group, an N-alkylaminocarbonyl group or an N-aralkylaminocarbonyl group, $R^1$ represents a C2–C10 alkylcarbonyl group, and $R^2$ represents a C2–C10 alkylcarbonyl group.

Another class of more preferred compounds include those wherein $R^\beta$ represents hydrogen atom, a C2–C10 alkylcarbonyl group, benzoyl group, a C4–C7 cycloalkylcarbonyl group, a C7–C15 aralkylcarbonyl group, benzoyl group, 2-quinolinylcarbonyl group or 4-pyridinylcarbonyl group, $R^1$ represents hydrogen atom, and $R^2$ represents a C2–C10 alkylcarbonyl group.

Compound of the General Formula (III) or (IV)

In the general formula (III) or (IV), the C1–C10 alkyl group and the C2–C10 alkylcarbonyl group represented by $R^1$ or $R^2$ are preferably selected from those groups mentioned as for the general formula (I) or (II), respectively. The silyl group represented by $R^3$ is preferably t-butyldimethylsilyl group. The C1–C5 alkyl group represented by $R^4$ or $R^5$ is preferably methyl group.

Among the compounds represented by the general formula (III) or (IV), a class of preferred compounds include those wherein $R^1$ represents hydrogen atom, a C1–C10 alkyl group or a C2–C10 alkylcarbonyl group, $R^2$ represents hydrogen atom, a C1–C10 alkyl group or a C2–C10 alkylcarbonyl group, $R^3$ represents t-butyldimethylsilyl group, $R^4$ represents methyl group, and $R^5$ represents methyl group.

Specific examples of preferred compounds represented by the general formula (I) or (II) include the followings compounds:

3-O-methylrokitamycin,
3-O-allylrokitamycin,
3-O-(3-(quinolin-3-yl)-2-propenyl)rokitamycin,
3-O-(quinolin-2-yl)carbonylrokitamycin,
3-O-(imidazol-1-yl)carbonylrokitamycin,
3-O-(N-methylamino)carbonylokitamycin,
3-O-(N,N-dimethylamino)carbonylrokitamycin,
3-O-(N-benzylamino)carbonylrokitamycin,
4"-O-isoamyl-3,3"-di-O-methylleucomycin,
3-O-methylleucomycin $A_7$,
3-O-benzoylleucomycin $A_7$,
3-O-(6-phenylhexanoyl)leucomycin $A_7$,
3-epi-rokitamycin,
3-epi-3-O-benzoylrokitamycin,
3-epi-3-O-(N-methylamino)carbonylrokitamycin,
3-epi-3-O-(N-benzylamino)carbonylrokitamycin,
3-epi-leucomycin $A_7$,
3-epi-3-O-propionylleucomycin $A_7$,
3-epi-3-O-benzoylleucomycin $A_7$,
3-epi-3-O-(4-methoxybenzoyl)leucomycin $A_7$,
3-epi-3-O-(4-nitrobenzoyl)leucomycin $A_7$,
3-epi-3-O-(pyridin-4-yl)carbonylleucomycin $A_7$,
3-epi-3-O-(3-phenylpropionyl)leucomycin $A_7$,
3-epi-3-O-cyclohexanecarbonylleucomycin $A_7$,
3-epi-3-O-(6-phenylhexanoyl)leucomycin $A_7$, and
3-epi-3-O-(quinolin-2-yl)carbonylleucomycin $A_7$.

However, the compounds are not limited to these examples.

Specific examples of preferred compounds represented by the general formula (III) or (IV) include the followings compounds:

2'-O-acetyl-9-O-tert-butyldimethylsilylrokitamycin 18-dimethylacetal,

2'-O-acetyl-9-O-tert-butyldimethylsilyl-4"-O-isoamyl-3"-O-methylleucomycin V 18-dimethylacetal, 2'-O-acetyl-9-O-tert-butyldimethylsilylleucomycin $A_7$ 18-dimethylacetal, 2'-O-acetyl-9-O-tert-butyldimethylsilyl-3-deoxy-3-oxorokitamycin 18-dimethylacetal, and 2'-O-acetyl-9-O-tert-butyldimethylsilyl-3-deoxy-3-oxoleucomycin $A_7$ 18-dimethylacetal.

However, the compounds are not limited to these examples.

The compounds of the present invention represented by the aforementioned general formulas can be prepared, for example, through the eleven steps shown in the following schemes. The following methods will be explained as typical methods for preparing the compounds of the present invention by referring to the following schemes: a methods for preparing compounds represented by the general formula (I) and (II) via a compound represented by the general formula (VI), as a compound represented by the general formula (III), wherein $R^3$ represents tert-butyldimethylsilyl group, $R^4$ represents methyl group and $R^5$ represents methyl group, and via a compound of the formula (XI), as a compound represented by the formula (IV), wherein $R^3$ represents tert-butyldimethylsilyl (TBDMS) group, $R^4$ represents methyl group and $R^5$ represents methyl group, respectively. The compounds that fall within the scope of general formula (I) and the general formula (III) are indicated in Scheme 1 as (VI)=(III), for example. This example means that a compound represented by the formula (VI) falls within the scope of the general formula (III). Novel compounds that fall within the scopes of the general formula (II) and the general formula (IV) are similarly indicated in Scheme 2 as, for example, (XI)=(IV) and the like.

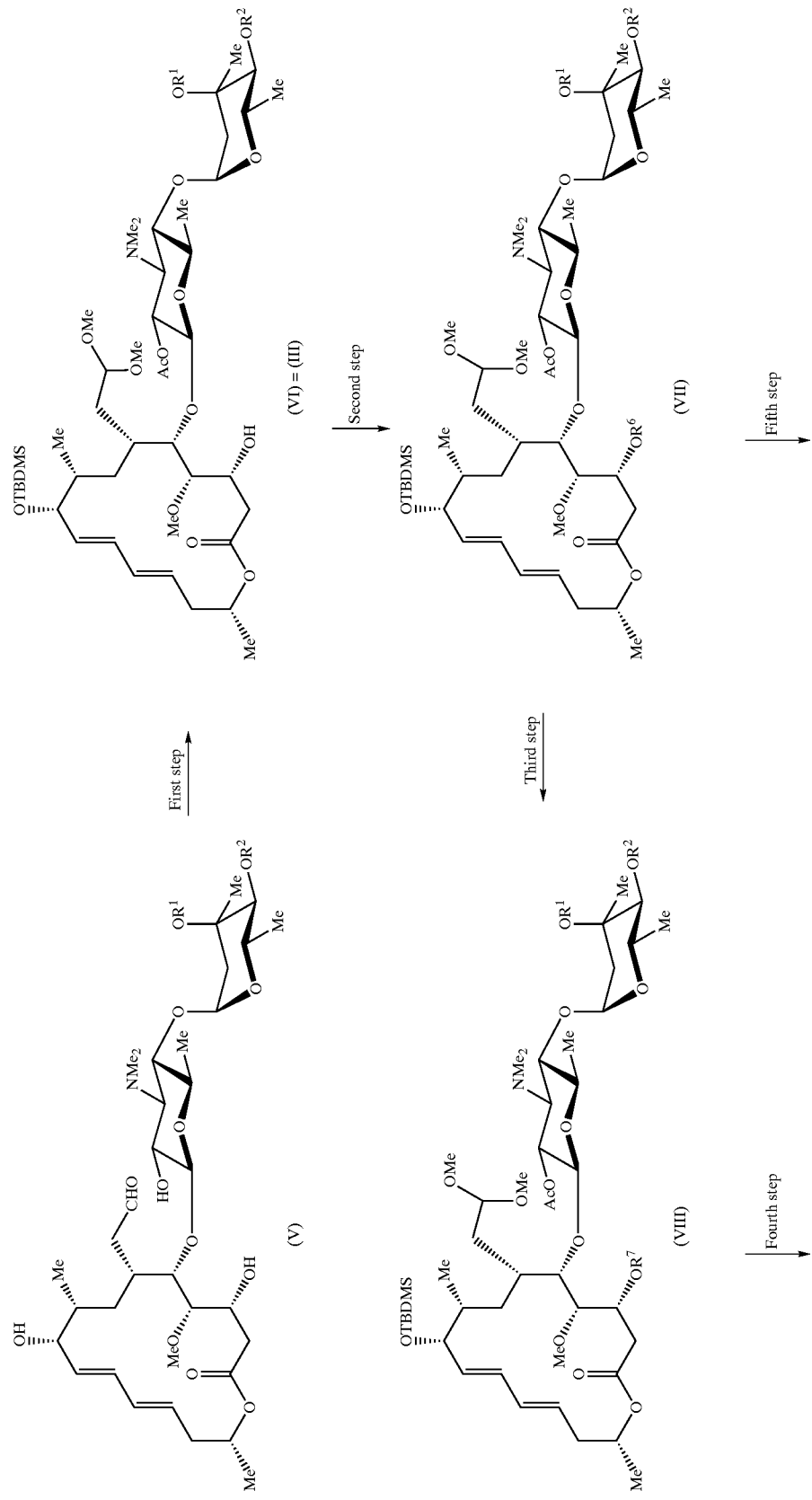
Scheme 1

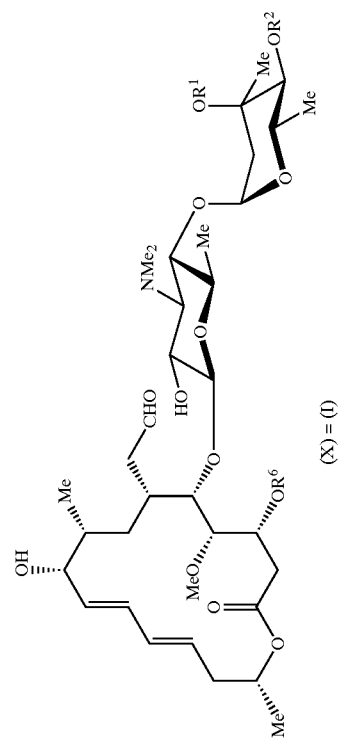
(X) = (I)
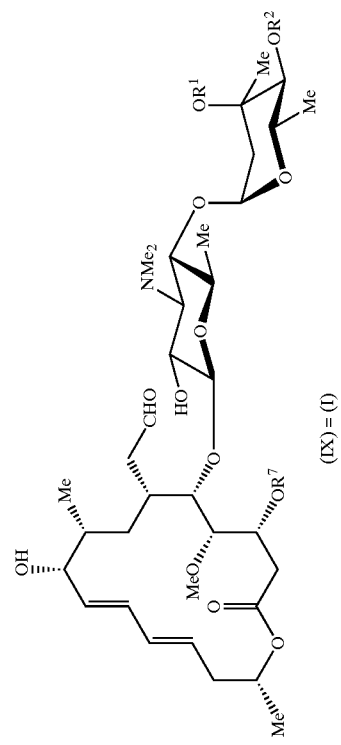
(IX) = (I)

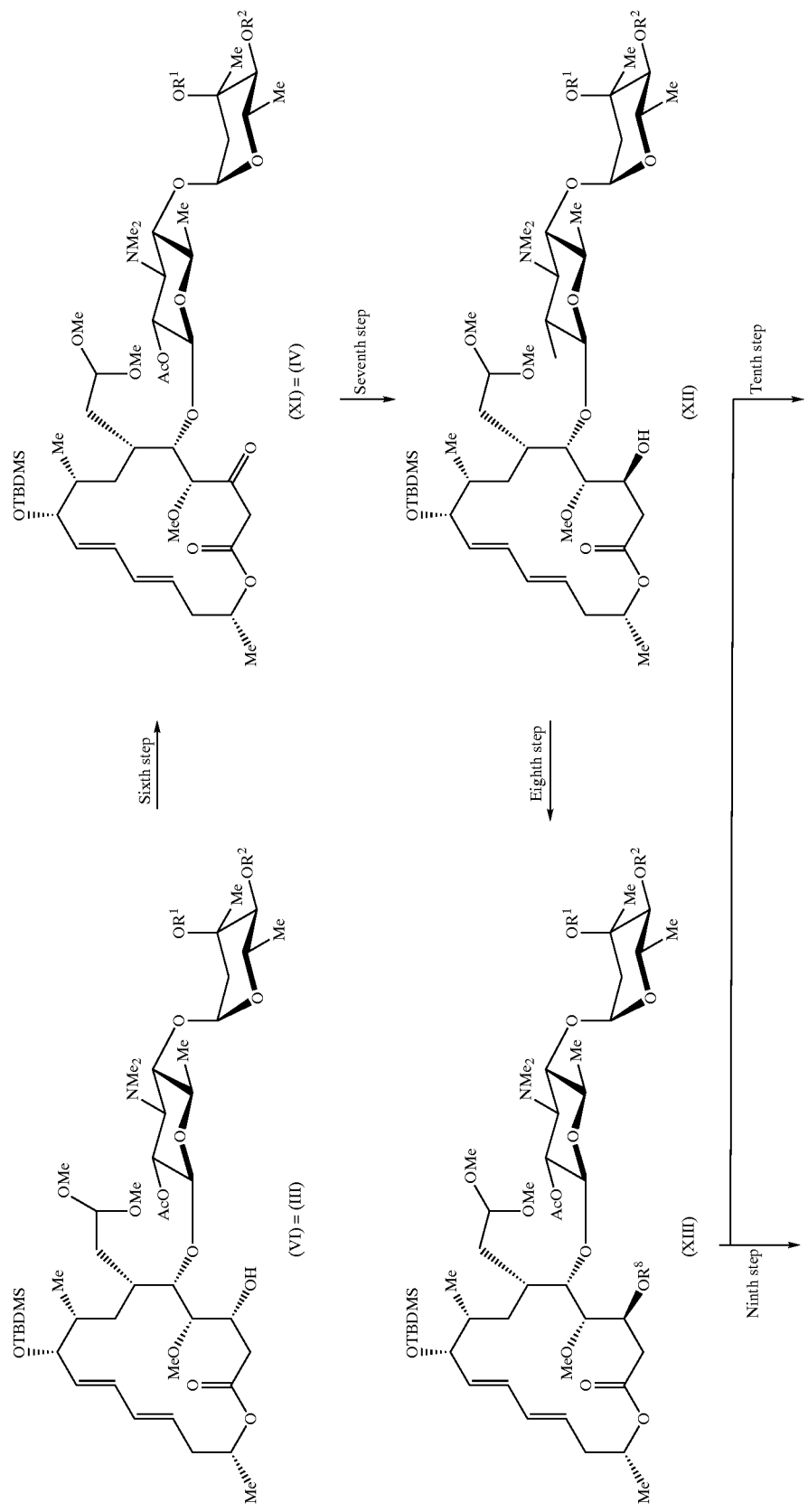

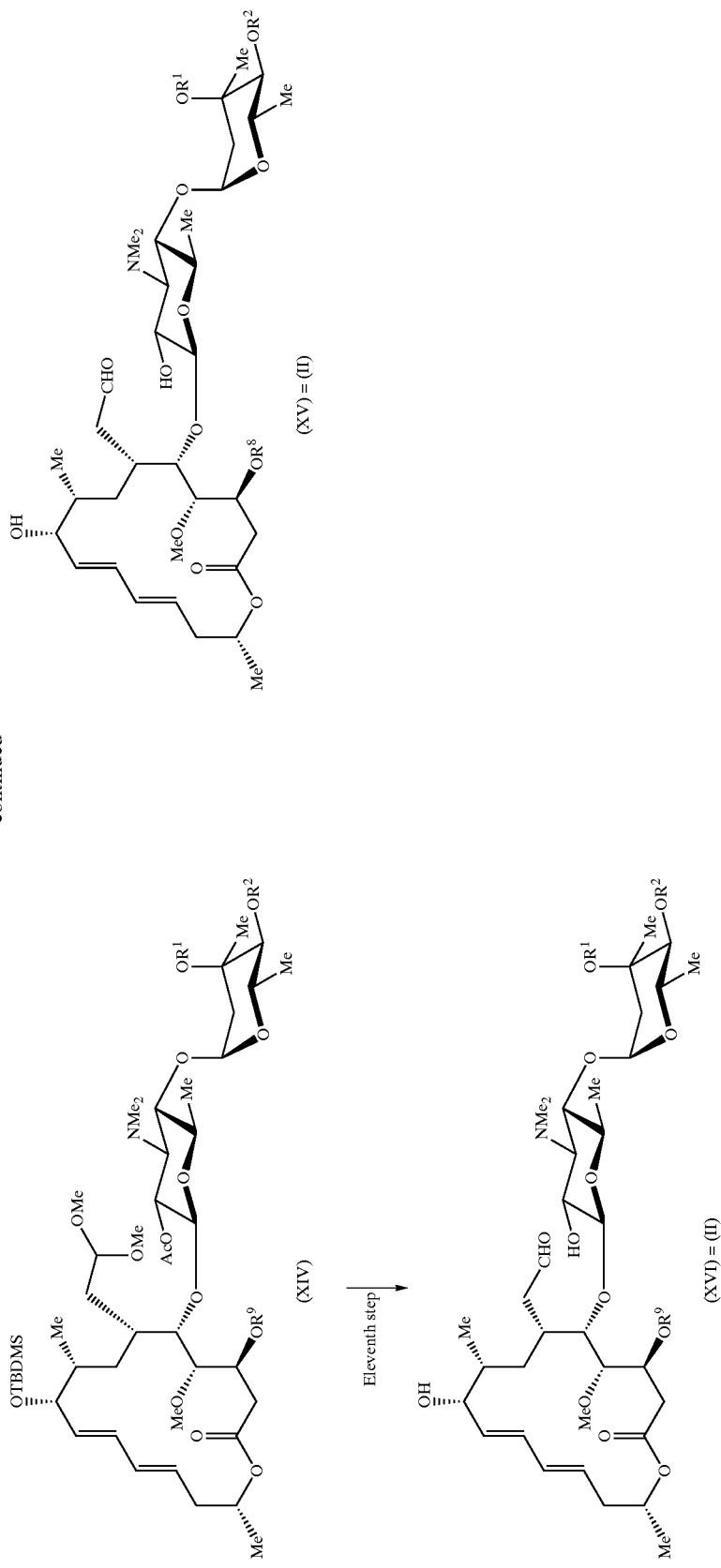

The method for preparing a compound represented by the general formula (I) (a novel compound having a modified hydroxyl group at the 3-position in the natural-type configuration) via a compound represented by the general formula (III) shown in Scheme 1 will be explained.

The first step is to produce a compound represented by the formula (VI), which falls within the scope of the general formula (III), by using a compound represented by the formula (V) as a starting material. In the previously reported synthesis of a 3-O-methyl-3",4"-O-diacyl-SPM I derivative, since SPM I itself has a saccharide at the 9-hydroxyl group, protection and deprotection of the 9-hydroxyl group are not required. Whilst, leucomycins a free hydroxyl group at the 9-position and therefore it is necessary to modify the 9-position with a protective group that can be selectively removed. Further, since alkylation may optionally be performed under a basic condition for the modification of the 3-position in the second step, it is desirable to select a protective group that can be removed under a stable and mild condition as well as under a basic condition. As a protected compound successively introduced stepwise with protective groups satisfying these requirements, a compound represented by the formula (VI) was selected. In the first step, the 9-hydroxyl group of the starting material represented by the formula (V) is protected with a silyl-type protective group, then the aldehyde portion at the 18-position is modified with an acetal type protective group, and the remaining 2'-hydroxyl group is acylated to obtain a compound represented by the formula (VI).

The modification of the 9-hydroxyl group of a compound represented by the formula (V) with a silyl-type protective group will be explained. In SPM or leucomycins having 17-demetyl-17-formylplatenolide II as a basic aglycone, a hemiacetal is formed between the 3- and 18-positions under a basic condition, and the acetal type hydroxyl group is readily silylated (S. Ōmura et al., J. Antibiot., 34, 1577, 1981 and K. Kurihara et al., J. Antibiot., 50, 32, 1997). As the silyl type protective group, a TBDMS group is most frequently used from viewpoints of its stability and ease of deprotection. In order to selectively introduce TBDMS solely at the 9-hydroxyl group, for example, the compound can be reacted with a required amount of TBDMSCl in a dry dimethylformamide (DMF) solution in the presence of imidazole. As the silylating reagent used for the introduction of TBDMS, 1 to 3 equivalents of a regent used for usual introduction of TBDMS such as $TBDMSOClO_3$, $TBDMSOSO_2CF_3$ and TBDMSCN, besides TBDMSCl. As the base, an organic base such as pyridine, lutidine and triethylamine can be used. 2 to 6 equivalents of imidazole can be preferably used. As a reaction solvent, dimethylformamide (DMF) as well as acetonitrile, methylene chloride, tetrahydrofuran (THF) and so forth may be used. The reaction proceeds in a good yield at a temperature in the range of 20° C. to 50° C., and the reaction time is 1 hour to 24 hours.

To introduce a silyl type protective group other than TBDMS group ($R^3$=TBDMS) into a compound represented by the general formula (III), a reaction can be similarly performed by using a silylating regent suitably selected depending on the structure of a desired $R^3$, for example, triethylsilyl chloride, triisopropylsilyl chloride, triphenylsilyl chloride, tribenzylsilyl chloride, dimethylisopropylsilyl chloride, t-butyldiphenylsilyl chloride or the like.

The subsequent modification of the 18-aldehyde with an acetal type protective group proceeds in a good yield in a mixed solvent of methyl orthoformate and methanol in the presence of an acid catalyst. As the acid used as a catalyst, an organic acid such as paratoluenesulfonic acid and camphorsulfonic acid may be used. 1.5 to 3 equivalents of pyridinium paratoluenesulfonate (PPTS) can preferably be used. As a reaction solvent, a mixed solution of equivalent amounts of methyl orthoformate, which also serves as a reagent, and methanol may be used in a 10-fold (v/w) to 60-fold (v/w) amount. The reaction proceeds in a good yield at a temperature within the range of 20° C. to 50° C., and the reaction time is 1 hour to 24 hours.

To introduce an acetal-type protective group other than dimethylacetal ($R^4$=methyl) into a compound represented by the general formula (III), a reaction can be similarly performed by using an alcohol suitably selected depending on the structure of a desired $R^4$, for example, ethanol, propanol, butanol, pentanol and so forth in combination of a corresponding ortho acid.

Then, the 2'-hydroxyl group in the mycaminose moiety can be acetylated to obtain a protected compound represented by the formula (VI). This protection step quantitatively proceeds by reacting acetic anhydride in acetonitrile. As the acetylating agent used for this reaction, 1 to 5 equivalents of acetic anhydride is preferably used, and acetonitrile is preferred as a reaction solvent. The reaction proceeds in a good yield at a temperature within the range of 20° C. to 60° C., and the reaction time is 1 hour to 24 hours.

When an acyl-type protective group other than acetyl group ($R^5$=methyl group) is introduced into a compound represented by the general formula (III), a reaction can be similarly performed by using an acylating agent suitably selected depending on the structure of a desired $R^5$, for example, propionic anhydride, butyric anhydride, valeric anhydride, caproic anhydride or the like.

The method for performing the second step and the optional third step to obtain a compound represented by the formula (VI), which is introduced at the 3-hydroxyl group with any one of organic groups of a C1–C10 alkyl group, a C3–C10 alkenyl group, a C7–C15 aralkyl group, a quinolinylalkyl group, a quinolinylalkenyl group, a C2–C10 alkylcarbonyl group, a C7–C15 aralkylcarbonyl group, a C4–C7 cycloalkylcarbonyl group, an imidazol-1-ylcarbonyl group, a benzoyl group, a quinolinylcarbonyl group, an N,N-dialkylaminocarbonyl group, an N-alkylaminocarbonyl group or an N-aralkylaminocarbonyl group, will be explained for each of the groups.

The method for introducing a C1–C10 alkyl group, a C3–C10 alkenyl group or a C7–C15 aralkyl group into the 3-hydroxyl group of a compound represented by the formula (VI) will be explained. In the usual Williamson alkylation, an unfavorable side reaction may occur depending on side chains that modify the 3"- and 4"-hydroxyl groups of mycarose (for example, when one is a free hydroxyl group and the other is acylated, an acyl rearrangement or the like may progress). To obtain a desired target compound while suppressing such a side reaction, for example, the 3-hydroxyl group may be solely and selectively alkylated by a reaction with an alkyl halide ($R^6X$) in dimethyl sulfoxide (DMSO) in the presence of potassium hydroxide (KOH). By the aforementioned alkylation, the 3-hydroxyl group can be solely and selectively alkylated without the aforementioned side reaction and without a change of the dimethylamino group of the mycaminose moiety into an onium salt, and a compound of the formula (VII) wherein $R^6$ is a C1–C10 alkyl group, a C3–C10 alkenyl group or a C7–C15 aralkyl group can be obtained.

The alkyl halide in the reaction of the second step is preferably used in an amount of 1–15 equivalents, and as the base, 1–15 equivalents of KOH is preferably used. DMSO is preferably used as a reaction solvent. The reaction proceeds in a good yield at a temperature within the range of 0° C. to 50° C., and the reaction time is 1 hour to 12 hours.

The third step is performed to produce a derivative of a compound represented by the formula (VI) where an alkenyl group having a substituent such as a quinolinylalkenyl group is introduced to the 3-hydroxyl group of the compound represented by the formula (VI). In the third step, the compound of the formula (VII) synthesized in the second step where $R^6$ represents allyl group is used and can be reacted with an alkyl halide by adding potassium carbonate and tetrabutylammonium chloride in DMF in the presence of palladium(II) acetate catalyst to obtain a compound represented by the formula (VIII). The alkyl halide used in the reaction of the third step is preferably used in an amount of 1 to 10 equivalents. Palladium(II) acetate as the catalyst is preferably used in an amount of 0.1 to 1 equivalent, and at this time, the catalyst may be activated by adding a ligand to palladium, such as triphenylphosphine, tri-(O-tolyl)phosphine and trimesitylphosphine. As the base, although it is also possible to use an organic base such as triethylamine, an inorganic base such as potassium carbonate, sodium carbonate and sodium hydrogencarbonate in an amount of 1 to 10 equivalents is preferably used in combination with an equivalent amount of tetrabutylammonium chloride. As a reaction solvent, acetonitrile, dioxane, toluene, dimethylacetamide, N-methylpyrrolidone, THF and the like may be used. DMF is preferred. The reaction proceeds in a good yield at a temperature within the range of 20° C. to 100° C., and the reaction time is 30 minutes to 4 days.

To introduce a C2–C10 alkylcarbonyl group, a C7–C15 aralkylcarbonyl group, a C4–C7 cycloalkylcarbonyl group, a benzoyl group or a quinolinylcarbonyl group to the 3-hydroxyl group of a compound represented by the formula (VI), the compound can be reacted with an acylating agent suitably selected depending on the structure of a desired $R^6$ (for example, when $R^6$ is defined as $COR^{6'}$, an acyl halide ($R^{6'}COX$), an acid anhydride (($R^{6'}CO)_2O$)) and the like). As the acylating agent in the reaction of the second step, either $R^{6'}COX$ or $(R^{6'}CO)_2O$ is preferably used in an amount of 1 to 15 equivalents, and as the base, 1 to 40 equivalents of an organic base such as pyridine as well as lutidine, collidine, triethylamine and diisopropylamine is preferably used. Furthermore, the reaction may be sometimes enhanced by addition of 0.1 to 4 equivalents of 4-dimethylaminopyridine. An aprotic solvent such as, besides methylene chloride, dichloroethane, chloroform, benzene, toluene, and xylene is preferred as a reaction solvent. The reaction proceeds in a good yield at a temperature within the range of 20° C. to 70° C., and the reaction time is 1 hour to 4 days.

The method for introducing an imidazol-1-ylcarbonyl-group, an N,N-dialkylaminocarbonyl group, an N-alkylaminocarbonyl group, or an N-aralkylaminocarbonyl group will be explained. The compounds of this class are obtained via a compound of the formula (VII) synthesized in the second step wherein $R^6$ represents an imidazol-1-yl carbonyl group and via the third step explained below. In the second step, a compound represented by the formula (VI) is first reacted with 1,1-carbonyldiimidazole (CDI) to obtain a compound of which 3-hydroxyl group is imidazol-1-ylcarbonylated. CDI for this reaction is preferably used in an amount of 1 to 15 equivalents, and as a reaction solvent, methylene chloride as well as chloroform, THF, benzene, toluene, xylene and the like can be used. The reaction proceeds in a good yield at a temperature within the range of 0° C. to 50° C., and the reaction time is 1 hour to 3 days.

Then, the compound of the formula (VII) obtained in the aforementioned method wherein $R^6$ is an imidazol-1-ylcarbonyl group can be subjected to the third step, in which the resulting compound is reacted with an amine selected from various amines including ammonia, primary amines and secondary amines, to obtain a compound of the formula (VIII) in which $R^7$ is an N-alkylaminocarbonyl group, an N,N-dialkylaminocarbonyl group or an N-aralkylaminocarbonyl group. The amine used in the reaction of the third step may be suitably selected depending on the structure of a desired $R^7$, and can be used in an amount of from 1 equivalent to an excess amount. As a reaction solvent, methylene chloride as well as chloroform, benzene, toluene, xylene, THF, DMF and the like can be used. The reaction proceeds in a good yield at a temperature within the range of 20° C. to 50° C., and the reaction time is 1 hour to 3 days.

The method for producing a compound represented by the formula (IX) or (X) by a deprotection reaction of a compound represented by the formula (VII) or (VIII) in accordance with the fourth and fifth steps will be explained. For the deprotection step, it is generally desirable to chose a mild condition in view of the side reactions such as the allyl rearrangement of 9- and 13-positions of the final compound.

After the 2-acetyl group is deprotected in an alcohol, the protective groups of the 9- and 18-positions are simultaneously deprotected under a weakly acidic condition to obtain a compound represented by the formula (I). As for the deacetylation reaction at the 2'-position, a lower alcohol such as methanol is preferably used in a 10-fold (v/w) to 200-fold (v/w) amount. The reaction is sometimes accelerated by addition of 1–10% of water. The reaction proceeds in a good yield at a temperature within the range of 20° C. to 50° C., and the reaction time is 1 hour to 4 days.

The subsequent deprotections at the 9-position and the 18-position can be performed by a reaction with difluoroacetic acid in a mixed solvent of acetonitrile and water. Although the acid catalyst for this reaction may be acetic acid, monofluoroacetic acid, trifluoroacetic acid or the like, difluoroacetic acid is preferred which is preferably used in an amount of 1–10 equivalents. As a reaction solvent, a mixture of equivalent amounts of acetonitrile and water is preferably used in a 10-fold (g/ml) to 500-fold (g/ml) amount. The reaction proceeds in a good yield at a temperature within the range of 20° C. to 50° C., and the reaction time is 12 hour to 4 days.

The method for producing a compound represented by the general formula (II), in which a modified 3-hydroxyl group has a non-natural type configuration, via a compound represented by the general formula (IV) will be explained by referring to Scheme 2.

The method for producing a compound represented by the formula (XI) by the sixth step using a compound represented by the formula (VI) as a starting material will be explained. In this step, if the oxidation is performed with a metal reagent, the dimethylamino group of the mycaminose moiety may be damaged. Therefore, it is desirable to perform the oxidation by a reaction with activated DMSO. However, in the oxidation reaction for converting the 3-hydroxyl group into carbonyl group by the reaction with activated DMSO, by-products usually observed in oxidation utilizing DMSO may sometimes cause a problem. In order to suppress these by-products, for example, the compound represented by the formula (VI) can be reacted with required amounts of DMSO and trifluoroacetic anhydride (TFAA) in a methylene chloride solvent in the presence of triethylamine, and a compound represented by the formula (XI) of which 3-hydroxyl group is oxidized can be obtained by this reaction. DMSO used for this reaction is preferably used in an amount of 1 to 10 equivalents. As an activating agent for DMSO, acetic anhydride, thionyl chloride, dicyclohexylcarbodiimide, sulfur trioxide/pyridine complex and the like may be used. TFAA is preferably used in an amount of 1 to 5 equivalents. Triethylamine is preferably used as the base in an amount of 1 to 15 equivalents, and methylene chloride is preferably used as a reaction solvent. The reaction proceeds in a good yield at a temperature within the range of −78° C. to 25° C., and the reaction time is 30 minutes to 3 hours.

In accordance with the successive seventh step, the compound represented by the formula (XI) can be reduced to obtain a compound represented by the formula (XII). This step requires a stereoselective reducing condition, and selection of the reaction solvent is especially important. For example, the 3-carbonyl group of the compound represented by the formula (XI) can be stereoselectively reduced by a reaction with sodium borohydride in dioxane as a solvent to obtain a compound represented by the formula (XII) in which the 3-carbonyl group is converted into a hydroxyl group having a non-natural-type configuration. As the reducing agent used for this reaction, sodium borohydride is preferably used in an amount of 1 to 10 equivalents. As the reaction solvent, although a lower alcohol such as methanol and ethanol may also be used, dioxane is preferably used. The reaction proceeds in a good yield at a temperature within the range of 0° C. to 50° C., and the reaction time is 6 hours to 2 days.

Then, the eighth step and the optional ninth step can be performed to produce a compound represented by the formula (XII) wherein any one of organic groups of C2–C10 alkylcarbonyl group, a C7–C15 aralkylcarbonyl group, a C4–C7 cycloalkylcarbonyl group, a benzoyl group, a quinolinylcarbonyl group, an imidazol-1-ylcarbonyl group, an N,N-dialkylaminocarbonyl group, an N-alkylaminocarbonyl group, N-aralkylaminocarbonyl group or a pyridinylcarbonyl group is introduced to the 3-hydroxyl group.

The reaction for introducing a C2–C10 alkylcarbonyl group, a C7–C15 aralkylcarbonyl group, a C4–C7 cycloalkylcarbonyl group, a benzoyl group, a quinolinylcarbonyl group or a pyridinylcarbonyl group to the 3-hydroxyl group of a compound represented by the formula (XII) can be performed by reacting the compound with an acylating agent suitably selected depending on the structure of a desired $R^8$ (for example, when $R^8$ is defined as $COR^{8'}$, an acyl halide ($R^{8'}COX$), an acid anhydride (($R^{8'}CO)_2O$)) and the like). As the acylating agent used in the reaction of the eighth step, either $R^{8'}COX$ or $(R^{8'}CO)_2O$ can be used in an amount of 1 to 20 equivalents, and as the base, 1 to 50 equivalents of an organic base such as pyridine as well as lutidine, collidine, triethylamine and diisopropylamine is preferably used. Furthermore, the reaction may sometimes be accelerated by addition of 0.1–4 equivalents of 4-dimethylaminopyridine. An aprotic solvent such as methylene chloride as well as dichloroethane, chloroform, benzene, toluene and xylene may preferably be used as a reaction solvent. The reaction proceeds in a good yield at a temperature within the range of 20° C. to 70° C., and the reaction time is 1 hour to 4 days.

The compounds introduced with an imidazol-1-ylcarbonyl-group, an N,N-dialkylaminocarbonyl group, an N-alkylaminocarbonyl group or an N-aralkylaminocarbonyl group can be produced via a compound of the formula (XIII) synthesized in the eighth step wherein $R^8$ represents an imidazol-1-ylcarbonyl group through the ninth step explained below. In the eighth step, the compound represented by the formula (XII) can be first reacted with 1,1-carbonyldiimidazole (CDI) to obtain a compound of which 3-hydroxyl group is imidazol-1-ylcarbonylated. CDI for this reaction is preferably used in an amount of 1–15 equivalents, and methylene chloride as well as chloroform, THF, benzene, toluene, xylene and the like can be used as a reaction solvent. The reaction proceeds in a good yield at a temperature within the range of 0° C. to 50° C., and the reaction time is 1 hour to 3 days.

Then, the compound of the formula (XIII) obtained in the aforementioned method wherein $R^8$ is an imidazol-1-ylcarbonyl group can be subjected to the ninth step, in which the compound is reacted with an amine selected from various amines including primary amines and secondary amines to obtain a compound of the formula (XIV) in which $R^9$ is an N,N-dialkylaminocarbonyl group, an N-alkylaminocarbonyl group or an N-aralkylaminocarbonyl group. The amine used in the reaction of the ninth step may be suitably selected depending on structure of a desired $R^9$, and can be used in an amount of from 1 equivalent to an excess amount. As the reaction solvent, methylene chloride as well as chloroform, benzene, toluene, xylene, THF, DMF and the like can be used. The reaction proceeds in a good yield at a temperature within the range of 20° C. to 50° C., and the reaction time is 1 hour to 4 days.

Finally, the compound represented by the formula (XIII) or (XIV) can be subjected to a deprotection reaction in accordance with the tenth and eleventh steps to produce a compound represented by the formula (XV) or (XVI). The same procedures as described in the fourth and fifth steps can be employed for the deprotection to obtain a compound represented by the general formula (II).

Specific methods for preparing the compounds falling within the scopes of the aforementioned general formulas of the present invention and physicochemical properties thereof are described in the examples in the specification. Accordingly, those skilled in the art can easily produce any of the compounds falling within the scopes of the aforementioned general formulas by referring to the general explanations of the production methods and specific preparation methods described in the examples, and making suitable modifications or alterations thereto as required. It should be understood that the methods for producing the compounds of the present invention are not limited to those explained above and those specifically described in the examples. Further, the compounds of the present invention are not limited to those prepared by the methods explained above or the methods specifically disclosed in the examples, and those produced by any methods are also fall within the scope of the present invention. For example, it should be understood that compounds obtained by chemical synthesis, industrial manufacture, extraction and purification, those based on the aforementioned general explanations and the specific explanations in the examples but modified further with known means, fall within the scope of the present invention. Furthermore, the 9-hydroxyl group of the compounds of the present invention can be acylated by a known method, and the resulting acylated compounds also fall within the scope of the present invention.

The compounds represented by the aforementioned general formulas (I), (II), (III) and (IV) can form salts with various bases or acids, and this property can be used for preparation of substances in a pure form, manufacture of active ingredients as medicaments and the like. For example, for the manufacture of the compounds, for example, the compounds can be solubilized in a polar solvent such as water by acidification, for example, so that they can be purified by extraction and isolated in the forms of salts having preferred physicochemical properties.

The forms of the salts that can be formed with the compounds represented by the aforementioned general formulas (I), (II), (III) and (IV) are not particularly limited. Forms of pharmaceutically acceptable salts of the compounds are preferred. For example, examples of base addition salts include lithium salts, sodium salts, potassium salts, magnesium salt, calcium salt, salts with ammonia and suitable non-toxic amines such as salts with C1–C6 alkylamine (e.g., triethylamine), salts with C1–C6 alkanolamine (e.g., diethanolamine, triethanolamine and the like), procaine salts, salts with cyclohexylamine (e.g., dicyclohexylamine), salts with benzylamine (e.g., N-methylbenzylamine, N-ethylbenzylamine, N-benzyl-β-phenethylamine, N,N-dibenzylethylenediamine, dibenzylamine and the like), and salts with heterocyclic amine (e.g., morpholine, N-ethylpyridine and the like), and examples of acid addition salts include, for example, salts of hydrohalogenic acids such as hydrofluoric acid, hydrochloric acid, hydrobromic acid and hydroiodic acid, salts of inorganic acids such as sulfuric acid, nitric acid, phosphoric acid, perchloric acid and carbonic acid, salts of organic acids, for example, salts of carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid and malic acid, salts of amino acids such as arginine, aspartic acid and glutamic acid, methanesulfonic acid, paratoluenesulfonic acid and the like.

The stereo structure indicated in the aforementioned general formulas (I), (II), (III) and (IV) of the present invention represent absolute configurations (according to ordinary expressions for configurations). The compounds of the present invention represented by the aforementioned general formulas (I), (II), (III) and (IV) may have one or more asymmetric carbons depending on the kinds of substituents, besides the asymmetric carbons shown in the aforementioned formulas. Any stereoisomers (optically active isomers or diastereoisomers) based on one or more of asymmetric carbons existing in the substituents and any mixtures thereof (racemates, mixtures of diastereomers and the like) fall within the scope of the present invention. In addition to the compounds of the present invention represented by the aforementioned general formulas (I), (II), (III) and (IV) in free forms and salts thereof, any hydrates thereof and any solvates thereof also fall within the scope of the present invention.

The compounds of the present invention represented by the aforementioned general formula (I) or (II) have antimicrobial activity and antibacterial activity, preferably antibacterial activity against Gram-positive bacteria, and useful as active ingredients of medicaments for therapeutic and/or prophylactic treatment of infectious diseases caused by microorganisms, preferably those caused by Gram-positive bacteria. The active ingredients of the medicaments provided by the present invention are selected from the group consisting of the compounds represented by the general formula (I) or (II) in free forms, pharmaceutically acceptable salts thereof, hydrates thereof and solvates thereof, and two or more kinds of active ingredients selected from the aforementioned group may be used in combination.

The medicament of the present invention can be administered to human or a mammal other than human via either an oral or parenteral route (for example, intravenous, intramuscular, subcutaneous, intraperitoneal, intrarectal, transdermal, transmucosal, ear dropping and nasal administration, inhalation and the like). As the medicaments of the present invention, the aforementioned active ingredients per se may be administered. In general, the medicament is provided as a pharmaceutical composition suitable for administration route using one or more additives for pharmaceutical preparations. Specifically, the medicaments of the present invention can be prepared as a pharmaceutical composition in the form of an oral medicament such as capsule, tablet, granule, powder, pill, subtilized granule and troche, injection or drip infusion mainly for intravenous administration, injection for intramuscular administration, agent for rectal administration, suppository containing oil or fat, aqueous suppository or the like.

These pharmaceutical compositions can be produced by a conventional method using additives for pharmaceutical preparation usually used for the manufacture thereof, for example, excipients, fillers, binders, wetting agents, disintegrating agents, surfactants, lubricants, dispersing agents, buffers, preservatives, dissolving aids, antiseptics, corrigants, soothing agents, stabilizers and the like. Examples of the excipients include lactose, fructose, glucose, corn starch, sorbit, crystalline cellulose and the like. Examples of the disintegrating agents include starch, sodium arginate, gelatin, calcium carbonate, calcium citrate, dextrin, magnesium carbonate, synthetic magnesium silicate and the like. Examples of the binders include, for example, methyl cellulose or salts thereof, ethyl cellulose, gum arabic, gelatin, hydroxypropyl cellulose, polyvinylpyrrolidone and the like. Examples of the lubricants include, for example, talc, magnesium stearate, polyethylene glycol, hydrogenated vegetable oil and the like. Examples of other additives include syrup, vaseline, glycerol, ethanol, propylene glycol, citric acid, sodium chloride, sodium sulfite, sodium phosphate and the like.

Although the content of the active ingredient in the pharmaceutical composition may vary depending on the dosage form, it is usually about 1–70% by weight, preferably 5–50% by weight based on a whole composition. The dose is suitably decided in view of administration route, the age and sexuality of a patient, a type of a disease and degree of symptoms and the like. The dose is usually about 0.1–5000 mg, preferably 1–600 mg, per day for an adult, and such a dose can be administered once a day or several times a day as divided portions.

EXAMPLES

The present invention will be explained more specifically with reference to the following examples. However, the scope of the present invention is not limited to these Examples.

Example 1

Preparation of 2'-O-Acetyl-9-O-tert-butyldimethylsilylrokitamycin 18-Dimethylacetal (Compound Represented by Formula (III) Wherein $R^1$ Represents Propionyl Group, $R^2$ Represents Normal Butyryl Group, $R^3$ Represents tert-Butyldimethylsilyl Group and $R^4$ and $R^5$ Both Represent Methyl Group)

2.5 g of rokitamycin (RKM), 0.71 g of TBDMSCl and 0.68 g of imidazole were stirred overnight in 30 ml of DMF at room temperature. The reaction mixture was added with 50 ml of methanol, concentrated under reduced pressure, then poured into ice water and extracted with 200 ml of ethyl acetate. The organic layer was washed successively with 50 ml each of saturated aqueous sodium hydrogencarbonate and saturated brine, dried over anhydrous sodium sulfate and filtered. The filtrate was concentrated under reduced pressure, and the resulting residue was purified by silica gel column chromatography (hexane:ethyl acetate (2:1)) to obtain 1.1 g of 9-O-tert-butyldimethylsilylrokitamycin.

1.1 g of the resulting compound was added with 30 ml of methanol and dissolved, and further added with 30 ml of methyl orthoformate and 0.98 g of PPTS and stirred overnight at 50° C. The reaction mixture was added with saturated aqueous sodium hydrogencarbonate and concentrated under reduced pressure. Then, the residue was diluted with 150 ml of chloroform and washed with 50 ml of saturated brine. The organic layer was dried over anhydrous sodium sulfate and the filtrate was concentrated under reduced pressure. Without purification, the resulting oil was added with 30 ml of acetonitrile and dissolved, further added with 0.59 ml of acetic anhydride and stirred overnight at 50° C. The reaction mixture was added with saturated aqueous sodium hydrogencarbonate and concentrated under reduced pressure. The resulting residue was extracted with 100 ml of ethyl acetate. The organic layer was washed with 50 ml of saturated brine, dried over anhydrous sodium sulfate and filtered. The filtrate was concentrated under reduced pressure, and the resulting residue was purified by silica gel column chromatography (hexane:ethyl acetate (5:1→2:1)) to obtain 0.92 g of a compound.

Physicochemical Properties of the Compound (1) Molecular formula: $C_{52}H_{91}NO_{17}Si$; (2) Mass spectrum (TSP): m/z 1030 (M+H)$^+$; (3) Specific rotation: $[\alpha]_D^{23}$ −98° (c 1.1, CHCl$_3$); (4) $^1$H NMR spectrum (300 MHz, CDCl$_3$) δ (ppm): 0.69 (br t, 7-H), 0.93 (d, 19-H), 0.96 (t, 4"-OCOCH$_2$CH$_2$CH$_3$), 1.05 (d, 6"-H), 1.11 (t, 3"-OCOCH$_2$CH$_3$), 1.18 (d, 6'-H), 1.29 (d, 16-H), 1.40 (s, 3"-CH$_3$), 1.45 (br dt, 7-H), 1.66 (dd, 2"-Hax), 1.68 (sex, 4"-OCOCH$_2$CH$_2$CH$_3$), 2.00 (s, 2'-OCOCH$_3$), 2.07 (dt, 14-H), 2.18 (br d, 2-H), 2.25 (q, 3"-OCOCH$_2$CH$_3$), 2.27 (q, 3"-OCOCH$_2$CH$_3$), 2.36 (t, 4"-OCOCH$_2$CH$_2$CH$_3$), 2.40 (s, 3'-N(CH$_3$)$_2$), 2.47 (m, 14-H), 2.55 (t, 3'-H), 2.63 (dd, 2-H), 2.94 (br d, 4-H), 3.09 (t, 4'-H), 3.17 (d, 2"-Heq), 3.18 (m, 5'-H), 3.25 (s, 18-OCH$_3$), 3.38 (s, 18-OCH$_3$), 3.44 (s, 4-OCH$_3$), 3.71 (br d, 3-H), 3.88 (br s, 3-OH), 4.02 (d, 5-H), 4.22 (dd, 9-H), 4.46 (dq, 5"-H), 4.47 (dd, 18-H), 4.55 (d, 4"-H), 4.67 (d, 1'-H), 4.79 (d, 1"-H), 4.93 (dd, 2'-H), 5.27 (ddq, 15-H), 5.49 (ddd, 13-H), 5.62 (dd, 10-H), 5.95 (br dd, 12-H), 6.02 (dd, 11-H).

Example 2

Preparation of 2'-O-Acetyl-9-O-tert-butyldimethylsilyl-3-O-methylrokitamycin 18-Dimethylacetal (Compound Represented by Formula (VII) Wherein R$^1$ Represents Propionyl Group, R$^2$ Represents Normal Butyryl Group and R$^6$ Represents Methyl Group)

99 mg of the compound of Example 1 was added with 2.0 ml of DMSO and dissolved, further added with 24 μl of methyl iodide and 91 mg of KOH, and the mixture was reacted at room temperature for 4 hours. The reaction mixture was added with 10 ml of water and extracted with 50 ml of chloroform. The organic layer was washed with 10 ml of saturated brine, dried over anhydrous sodium sulfate and filtered. The filtrate was concentrated under reduced pressure, and the resulting residue was purified by silica gel column chromatography (hexane:ethyl acetate (5:1)) to obtain 81 mg of a compound.

Physicochemical Properties of the Compound (1) Molecular formula: $C_{53}H_{93}NO_{17}Si$; (2) Mass spectrum (TSP): m/z 1044 (M+H)$^+$; (3) Specific rotation: $[\alpha]_D^{24}$ −105° (c 0.53, CHCl$_3$); (4) $^1$H NMR spectrum (300 MHz, CDCl$_3$) δ (ppm): 0.96 (d, 19-H), 0.97 (t, 4'-OCOCH$_2$CH$_2$CH$_3$), 1.05 (d, 6"-H), 1.12 (t, 3"-OCOCH$_2$CH$_3$), 1.19 (d, 6'-H), 1.28 (d, 16-H), 1.40 (s, 3"-CH$_3$), 1.66 (dd, 2"-Hax), 1.68 (sex, 4"-OCOCH$_2$CH$_2$CH$_3$), 2.00 (s, 2'-OCOCH$_3$), 2.14 (dt, 14-H), 2.26 (q, 3"-OCOCH$_2$CH$_3$), 2.28 (q, 3"-OCOCH$_2$CH$_3$), 2.37 (t, 4"-OCOCH$_2$CH$_2$CH$_3$), 2.40 (s, 3'-N(CH$_3$)$_2$), 2.59 (t, 3'-H), 2.65 (dd, 2H), 2.84 (dd, 4-H), 3.09 (t, 4'-H), 3.17 (d, 2"-Heq), 3.19 (m, 5'-H), 3.27 (s, 18-OCH$_3$), 3.31 (s, 18-OCH$_3$), 3.39 (s, 4-OCH$_3$), 3.40 (s, 3-OCH$_3$), 3.94 (br d, 5-H), 4.17 (dd, 9-H), 4.46 (dq, 5"-H), 4.53 (dd, 18-H), 4.55 (d, 4"-H), 4.65 (d, 1'-H), 4.79 (d, 1"-H), 4.95 (dd, 2'-H), 5.08 (ddq, 15-H), 5.51 (ddd, 13-H), 5.62 (dd, 10-H), 6.02 (br dd, 12-H), 6.07 (dd, 11-H).

Example 3

Preparation of 3-O-Methylrokitamycin (Compound Represented by Formula (I) Wherein R$^1$ Represents Propionyl Group, R$^2$ Represents Normal Butyryl Group and R$^\alpha$ Represents Methyl Group)

206 mg of the compound of Example 2 was added with 9.0 ml of methanol:water (9:1) and reacted overnight at 50° C. The reaction mixture was concentrated under reduced pressure, and the resulting residue was purified by silica gel column chromatography (hexane:ethyl acetate (5:1→3:1→2:1→1:1)) to obtain 166 mg of oil. 81 mg of this compound was added with 13 ml of acetonitrile and dissolved, further added with 13 ml of water and 26 μl of difluoroacetic acid, and the mixture was stirred at room temperature for 2 days. The reaction mixture was added with 15 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (200:10:1)) to obtain 53 mg of a compound.

Physicochemical Properties of the Compound (1) Molecular formula: $C_{43}H_{71}NO_{15}$; (2) Mass spectrum (TSP): m/z 842 (M+H)$^+$; (3) Specific rotation: $[\alpha]_D^{24}$ −89° (c 0.51, CHCl$_3$); (4) $^1$H NMR spectrum (300 MHz, CDCl$_3$) δ (ppm): 0.97 (t, 4"-OCOCH$_2$CH$_2$CH$_3$), 1.01 (d, 19-H), 1.07 (d, 6"-H), 1.10 (t, 3"-OCOCH$_2$CH$_3$), 1.15 (d, 6'-H), 1.29 (d, 16-H), 1.40 (s, 3"-CH$_3$), 1.42 (br dt, 7-H), 1.68 (sex, 4"-OCOCH$_2$CH$_2$CH$_3$), 1.68 (dd, 2"-Hax), 1.83 (m, 8-H), 2.04 (m, 6-H), 2.16 (dt, 14-H), 2.25 (q, 3"-OCOCH$_2$CH$_3$), 2.27 (q, 3"-OCOCH$_2$CH$_3$), 2.35 (t, 4"-OCOCH$_2$CH$_2$CH$_3$), 2.36 (dd, 2-H), 2.51 (s, 3'-N(CH$_3$)$_2$), 2.73 (dd, 2-H), 2.96 (dd, 4-H), 2.96 (dd, 17-H), 3.14 (t, 4'-H), 3.18 (m, 5'-H), 3.20 (d, 2"-Heq), 3.38 (dd, 2'-H), 3.46 (s, 4-OCH$_3$), 3.48 (s, 3-OCH$_3$), 3.86 (br d, 5-H), 4.09 (dd, 9-H), 4.38 (d, 1'-H), 4.50 (dq, 5"-H), 4.57 (d, 4"-H), 4.82 (d, 1"-H), 5.12 (ddq, 15-H), 5.62 (ddd, 13-H), 5.67 (dd, 10-H), 6.07 (br dd, 12-H), 6.26 (dd, 11-H), 9.77 (br s, 18-H).

Example 4

Preparation of 2'-O-Acetyl-3-O-allyl-9-O-tert-butyldimethylsilylrokitamycin 18-Dimethylacetal (Compound Represented by Formula (VII) Wherein R$^1$ Represents Propionyl Group, R$^2$ Represents Normal Butyryl Group and R$^6$ Represents Allyl Group)

187 mg of the compound of Example 1 was added with 1 ml of DMSO and dissolved, further added with 166 μl of allyl iodide and 140 mg of KOH, and then the mixture was reacted at room temperature for 4 hours. The reaction mixture was added with 10 ml of water and extracted with 50 ml of diethyl ether. The organic layer was washed with 15 ml of saturated brine, dried over anhydrous sodium sulfate and filtered. The filtrate was concentrated under reduced pressure, and the resulting residue was purified by silica gel column chromatography (hexane:ethyl acetate (10:1→5:1→1:1)) to obtain 66 mg of a compound.

Physicochemical Properties of the Compound (1) Molecular formula: $C_{52}H_{95}NO_{15}Si$; (2) Mass spectrum (TSP): m/z 1070 (M+H)$^+$; (3) Specific rotation: $[\alpha]_D^{22}$ −103° (c 0.58, CHCl$_3$); (4) $^1$H NMR spectrum (300 MHz, CDCl$_3$) δ (ppm): 0.95 (d, 19-H), 0.96 (t, 4"-OCOCH$_2$CH$_2$CH$_3$), 1.04 (d, 6"-H), 1.11 (t, 3"-OCOCH$_2$CH$_3$), 1.17 (d, 6'-H), 1.27 (d, 16-H), 1.39 (s, 3"-CH$_3$), 1.65 (dd, 2"-Hax), 1.67 (sex, 4"-OCOCH$_2$CH$_2$CH$_3$), 2.00 (s, 2'-OCOCH$_3$), 2.11 (dt, 14-H), 2.24 (q, 3"-OCOCH$_2$CH$_3$), 2.27 (q, 3"-OCOCH$_2$CH$_3$), 2.36 (t, 4"-OCOCH$_2$CH$_2$CH$_3$), 2.39 (s, 3'-N(CH$_3$)$_2$), 2.44 (m, 14-H), 2.59 (t, 3'-H), 2.66 (dd, 2-H), 2.78 (dd, 4-H), 3.07 (t, 4'-H), 3.16 (d, 2"-Heq), 3.18 (m, 5'-H), 3.27 (s, 18-OCH$_3$), 3.30 (s, 18-OCH$_3$), 3.38 (s, 4-OCH$_3$), 3.48 (br t, 3-H), 3.95 (br dd, 3-OCH$_2$CH=CH$_2$), 4.15 (dd, 9-H), 4.18 (br d, 5-H), 4.45 (dq, 5"-H), 4.49 (dd, 18-H), 4.54 (d, 4"-H), 4.62 (d, 1'-H), 4.77 (d, 1"-H), 4.94 (dd, 2'-H), 5.15 (ddq, 15-H), 5.16 (dd, 3-OCH$_2$CH=CH$_2$), 5.25 (dd, 3-OCH$_2$CH=CH$_2$), 5.52 (ddd, 13-H), 5.59 (dd, 10-H), 5.89 (ddt, 3-OCH$_2$CH=CH$_2$), 6.00 (br dd, 12-H), 6.05 (dd, 11-H).

Example 5

Preparation of 3-O-Allylrokitamycin (Compound Represented by Formula (I) Wherein R$^1$ Represents Propionyl Group, R$^2$ Represents Normal Butyryl Group and R$^\alpha$ Represents Allyl Group)

108 mg of the compound of Example 4 was added with 5.0 ml of methanol:water (9:1) and reacted overnight at 45° C. The reaction mixture was concentrated under reduced pressure, and the resulting residue was purified by silica gel column chromatography (hexane:ethyl acetate (5:1→3:1)) to obtain 95 mg of oil. 85 mg of the resulting compound was added with 14 ml of acetonitrile and dissolved, further added with 14 ml of water and 26 μl of difluoroacetic acid, and then the mixture was stirred at room temperature for 2 days. The reaction mixture was added with 15 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by silica gel column chromatography (chloroform:methanol:aqueous ammonia (250:1:0.1→100:1:0.1)) to obtain 54 mg of a compound.

Physicochemical Properties of the Compound (1) Molecular formula: $C_{42}H_{73}NO_{13}$; (2) Mass spectrum (TSP): m/z 868 (M+H)$^+$; (3) Specific rotation: $[\alpha]_D^{22}$ −86° (c 0.53, CHCl$_3$); (4) $^1$H NMR spectrum (300 MHz, CDCl$_3$) δ (ppm): 0.96 (t, 4"-OCOCH$_2$CH$_2$CH$_3$), 1.01 (d 19-H), 1.06 (d, 6"-H), 1.09 (t, 3"-OCOCH$_2$CH$_3$), 1.13 (d, 6'-H), 1.28 (d, 16-H), 1.40 (s, 3"-CH$_3$), 1.67 (dd, 2"-Hax), 1.68 (sex, 4"-OCOCH$_2$CH$_2$CH$_3$), 1.79 (m, 8-H), 1.98 (br t, 6-H), 2.15 (dt, 14-H), 2.24 (q, 3"-OCOCH$_2$CH$_3$), 2.27 (q, 3"-OCOCH$_2$CH$_3$), 2.34 (dd, 3'-H), 2.35 (t, 4"-OCOCH$_2$CH$_2$CH$_3$), 2.43 (dd, 2-H), 2.50 (s, 3'-N(CH$_3$)$_2$), 2.71 (dd, 2-H), 2.91 (dd, 4-H), 2.92 (dd, 17-H), 3.12 (t, 4'-H), 3.13 (m, 5'-H), 3.19 (d, 2"-Heq), 3.40 (dd, 2'-H), 3.48 (s, 4-OCH$_3$), 3.63 (br t, 3-H), 3.83 (br d, 5-H), 4.06 (br ddt, 3-OCH$_2$CH=CH$_2$), 4.10 (br dd, 9-H), 4.17 (br ddt, 3-OCH$_2$CH=CH$_2$), 4.38 (d, 1'-H), 4.50 (dq, 5"-H), 4.56 (d, 4"-H), 4.80 (d, 1"-H), 5.14 (br dd, 3-OCH$_2$CH=CH$_2$), 5.15 (ddq, 15-H), 5.29 (br dq, 3-OCH$_2$CH=CH$_2$), 5.62 (ddd, 13-H), 5.66 (dd, 10-H), 6.05 (br dd, 12-H), 6.23 (dd, 11-H), 9.77 (br s, 18-H).

Example 6

Preparation of 2'-O-Acetyl-9-O-tert-butyldimethylsilyl-3-O-(3-(quinolin-3-yl)-2-propenyl)rokitamycin 18-Dimethylacetal (Compound Represented by Formula (III) Wherein R$^1$ Represents Propionyl Group, R$^2$ Represents Normal Butyryl Group and R$^7$ Represents 3-(Quinolin-3-yl)-2-propenyl Group)

71.4 mg of the compound of Example 4 was added with 0.7 ml of DMF and dissolved, further added with 27.8 mg of potassium carbonate, 77.9 mg of tetrabutylammonium chloride, 2.6 mg of palladium acetate and 36.0 μl of 3-bromoquinoline, and the mixture was reacted at 50° C. for 4 days. The reaction mixture was added with 50 ml of ethyl acetate, and the organic layer was washed with water, saturated aqueous sodium hydrogencarbonate and saturated brine, dried over anhydrous sodium sulfate and filtered. The filtrate was concentrated under reduced pressure, and the resulting residue was purified by silica gel column chromatography (hexane:ethyl acetate (3:1)) to obtain 32.5 mg of a compound.

Physicochemical Properties of the Compound (1) Molecular formula: $C_{64}H_{100}N_2O_{17}Si$; (2) Mass spectrum (FAB): m/z 1197 (M+H)$^+$; (3) Specific rotation: $[\alpha]_D^{22}$ −68° (c 0.87, CHCl$_3$); (4) $^1$H NMR spectrum (300 MHz, CDCl$_3$) δ (ppm): 0.95 (d, 19-H), 0.96 (t, 4"-OCOCH$_2$CH$_2$CH$_3$), 1.04 (d, 6"-H), 1.11 (t, 3"-OCOCH$_2$CH$_3$), 1.12 (d, 6'-H), 1.28 (d, 16-H), 1.39 (s, 3"-CH$_3$), 1.61 (dd, 2"-Hax), 1.67 (sex, 4"-OCOCH$_2$CH$_2$CH$_3$), 1.76 (m, 8-H), 2.02 (s, 2'-OCOCH$_3$), 2.12 (dt, 14-H), 2.24 (q, 3"-OCOCH$_2$CH$_3$), 2.27 (q, 3"-OCOCH$_2$CH$_3$), 2.35 (t, 4"-OCOCH$_2$CH$_2$CH$_3$), 2.40 (s, 3'-N(CH$_3$)$_2$), 2.59 (t, 3'-H), 2.75 (dd, 2-H), 2.91 (dd, 4-H), 3.09 (t, 4'-H), 3.12 (d, 2"-Heq), 3.20 (s, 18-OCH$_3$), 3.25 (s, 18-OCH$_3$), 3.44 (s, 4-OCH$_3$), 3.64 (m, 3-H), 4.02 (m, 5-H), 4.15 (dd, 9-H), 4.30 (br dd, 3-O—CH$_2$CH=CH-quinoline), 4.37 (br dd, 3-O—CH$_2$CH=CH-quinoline), 4.45 (dq, 5"-H), 4.53 (d, 4"-H), 4.55 (dd, 18-H), 4.68 (d, 1'-H), 4.74 (d, 1"-H), 4.96 (dd, 2'-H), 5.12 (ddq, 15-H), 5.52 (ddd, 13-H), 5.62 (dd, 10-H), 6.02 (br dd, 12-H), 6.06 (dd, 11-H), 6.54 (dt, 3-O—CH$_2$CH=CH-quinoline), 6.75 (d, 3-O—CH$_2$CH=CH-quinoline), 7.52 (ddd, quinoline), 7.53 (br d, quinoline), 7.65 (ddd, quinoline), 7.83 (dd, quinoline), 8.04 (br d, quinoline), 8.06 (s, quinoline), 8.98 (d, quinoline).

Example 7

Preparation of 3-O-(3-(Quinolin-3-yl)-2-propenyl)rokitamycin (Compound Represented by Formula (I) Wherein R$^1$ Represents Propionyl Group, R$^2$ Represents Normal Butyryl Group and R$^\alpha$ Represents 3-(Quinolin-3-yl)-2-propenyl Group)

120 mg of the compound of Example 6 was added with 6.0 ml of methanol:water (9:1) and reacted overnight at 50° C. The reaction mixture was concentrated under reduced pressure, and the resulting residue was purified by silica gel column chromatography (chloroform:methanol (200:1→50:1)) to obtain 103 mg of a compound. 95.7 mg of the resulting compound was added with 14 ml of acetonitrile and dissolved, further added with 14 ml of water and 27.0 μl of difluoroacetic acid, and then the mixture was stirred at room temperature for 2 days. The reaction mixture was added with 30 ml of saturated aqueous sodium hydrogencarbonate and extracted with 80 ml of chloroform. The organic layer was washed with 30 ml of saturated brine, dried over anhydrous sodium sulfate and filtered. The filtrate was concentrated under reduced pressure, and the resulting residue was purified by preparative TLC (chloroform:methanol:aqueous ammonia (100:10:1)) to obtain 51.0 mg of a compound.
Physicochemical Properties of the Compound
(1) Molecular formula: $C_{54}H_{78}N_2O_{15}$; (2) Mass spectrum (FAB): m/z 995 (M+H)$^+$; (3) Specific rotation: $[\alpha]_D^{24}$ −32° (c 0.59, CHCl$_3$); (4) $^1$H NMR spectrum (300 MHz, CDCl$_3$) δ (ppm): 0.95 (t, 4"-OCOCH$_2$CH$_2$CH$_3$), 1.00 (d, 19-H), 1.02 (d, 6'-H), 1.03 (t, 3"-OCOCH$_2$CH$_3$), 1.05 (d, 6"-H), 1.10 (br t, 7-H), 1.29 (d, 16-H), 1.37 (s, 3"-CH$_3$), 1.39 (ddd, 7-H), 1.62 (dd, 2"-Hax), 1.66 (sex, 4"-OCOCH$_2$CH$_2$CH$_3$), 1.83 (m, 8-H), 2.15 (dt, 14-H), 2.19 (q, 3"-OCOCH$_2$CH$_3$), 2.21 (q, 3"-OCOCH$_2$CH$_3$), 2.34 (t, 4"-OCOCH$_2$CH$_2$CH$_3$), 2.50 (s, 3'-N(CH$_3$)$_2$), 2.81 (dd, 2-H), 2.96 (dd, 17-H), 3.01 (dd, 4-H), 3.12 (m, 5'-H), 3.13 (t, 4'-H), 3.13 (d, 2"-H), 3.36 (dd, 2'-H), 3.51 (s, 4-OCH$_3$), 3.73 (br d, 3-H), 3.91 (br d, 5-H), 4.09 (br dd, 9-H), 4.34 (dd, 3-O—CH$_2$CH=CH-quinoline), 4.42 (d, 1'-H), 4.44 (dd, 3-O—CH$_2$CH=CH-quinoline), 4.46 (dq, 5"-H), 4.53 (d, 4"-H), 4.76 (d, 1"-H), 5.11 (ddq, 15-H), 5.60 (ddd, 13-H), 5.67 (dd, 10-H), 6.05 (br dd, 12-H), 6.24 (dd, 11-H), 6.63 (dt, 3-O—CH$_2$CH=CH-quinoline), 6.78 (d, 3-O—CH$_2$CH=CH-quinoline), 7.49 (ddd, quinoline), 7.63 (ddd, quinoline), 7.81 (dd, quinoline), 8.04 (d, quinoline), 8.10 (d, quinoline), 9.02 (d, quinoline), 9.75 (br s, 18-H).

Example 8

Preparation of 2'-O-Acetyl-9-O-tert-butyldimethylsilyl-3-O-(quinolin-2-yl)carbonylrokitamycin 18-Dimethylacetal (Compound Represented by Formula (VII) Wherein $R^1$ Represents Propionyl Group, $R^2$ Represents Normal Butyryl Group and $R^6$ Represents Quinolin-2-ylcarbonyl Group)

151 mg of the compound of Example 1 was added with 1.5 ml dichloroethane and dissolved, further added with 228 μl of triethylamine, 168 mg of quinolin-2-ylcarbonyl chloride and 40.9 mg of 4-dimethylaminopyridine, and the mixture was reacted at 60° C. for 3 days. The reaction mixture was added with 30 ml of saturated aqueous sodium hydrogencarbonate and extracted with 100 ml of chloroform. The organic layer was washed successively with 30 ml of 5% KHSO$_4$ aqueous solution, 30 ml of saturated aqueous sodium hydrogencarbonate and saturated brine, dried over anhydrous sodium sulfate and filtered. The filtrate was concentrated under reduced pressure, and the resulting residue was purified by silica gel column chromatography (hexane:ethyl acetate (3:1)) to obtain 137 mg of a compound.
Physicochemical Properties of the Compound
(1) Molecular formula: $C_{62}H_{96}N_2O_{18}Si$; (2) Mass spectrum (TSP): m/z 1185 (M+H)$^+$; (3) Specific rotation: $[\alpha]_D^{24}$ −57° (c 0.57, CHCl$_3$); (4) $^1$H NMR spectrum (300 MHz, CDCl$_3$) δ (ppm): 0.95 (d, 19-H), 0.97 (t, 4"-OCOCH$_2$CH$_2$CH$_3$), 0.98 (d, 6'-H), 1.05 (d, 6"-H), 1.18 (t, 3"-OCOCH$_2$CH$_3$), 1.23 (d, 16-H), 1.41 (s, 3"-CH$_3$), 1.47 (dd, 17-H), 1.64 (dd, 2"-Hax), 1.68 (sex, 4"-OCOCH$_2$CH$_2$CH$_3$), 1.83 (m, 8-H), 2.03 (s, 2'-OCOCH$_3$), 2.14 (dt, 14-H), 2.30 (q, 3"-OCOCH$_2$CH$_3$), 2.33 (q, 3"-OCOCH$_2$CH$_3$), 2.37 (t, 4"-OCOCH$_2$CH$_2$CH$_3$), 2.41 (s, 3'-N(CH$_3$)$_2$), 2.44 (br d, 14-H), 2.58 (t, 3'-H), 2.90 (s, 18-OCH$_3$), 2.93 (dd, 2-H), 2.97 (s, 18-OCH$_3$), 3.07 (t, 4'-H), 3.15 (d, 2"-Heq), 3.23 (dq, 5'-H), 3.30 (br d, 4-H), 3.54 (s, 4-OCH$_3$), 3.99 (br d, 5-H), 4.19 (dd, 18-H), 4.23 (dd, 9-H), 4.47 (dq, 5"-H), 4.55 (d, 4"-H), 4.73 (d, 1"-H), 4.79 (d, 1'-H), 4.94 (dd, 2'-H), 5.01 (ddq, 15-H), 5.38 (br d, 3-H), 5.61 (dd, 10-H), 5.89 (ddd, 13-H), 6.08 (br dd, 12-H), 6.50 (dd, 11-H), 7.63 (ddd, 3-OCO-quinoline), 7.81 (ddd, 3-OCO-quinoline), 7.88 (br d, 3-OCO-quinoline), 8.16 (d, 3-OCO-quinoline), 8.30 (d, 3-OCO-quinoline), 8.31 (br d, 3-OCO-quinoline).

Example 9

Preparation of 3-O-(Quinolin-2-yl)carbonylrokitamycin (Compound Represented by Formula (I) Wherein $R^1$ Represents Propionyl Group, $R^2$ Represents Normal Butyryl Group and $R^\alpha$ Represents Quinolin-2-ylcarbonyl Group)

104 mg of the compound of Example 8 was added with 7.0 ml of methanol:water (9:1) and reacted overnight at 45° C. The reaction mixture was concentrated under reduced pressure, and the resulting residue was purified by silica gel column chromatography (hexane:ethyl acetate (1:1)) to obtain 88.4 mg of a compound. 83.0 mg of the resulting compound was added with 12 ml of acetonitrile and dissolved, further added with 12 ml of water and 23.0 μl of difluoroacetic acid and stirred at room temperature for 2 days. The reaction mixture was added with 20 ml of saturated aqueous sodium hydrogencarbonate and extracted with 60 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (100:10:1)) to obtain 33.2 mg of a compound.
Physicochemical Properties of the Compound
(1) Molecular formula: $C_{52}H_{74}N_2O_{16}$; (2) Mass spectrum (FAB): m/z 983 (M+H)$^+$; (3) Specific rotation: $[\alpha]_D^{24}$ +3.0° (c 0.53, CHCl$_3$); (4) $^1$H NMR spectrum (300 MHz, CDCl$_3$) δ (ppm): 0.96 (t, 4"-OCOCH$_2$CH$_2$CH$_3$), 0.96 (d, 6'-H), 0.99 (d, 19-H), 1.06 (d, 6"-H), 1.12 (t, 3"-OCOCH$_2$CH$_3$), 1.22 (d, 16-H), 1.39 (s, 3"-CH$_3$), 1.53 (br t, 7-H), 1.67 (dd, 2"-Hax), 1.67 (sex, 4"-OCOCH$_2$CH$_2$CH$_3$), 1.89 (m, 8-H), 2.14 (dt, 14-H), 2.26 (q, 3"-OCOCH$_2$CH$_3$), 2.27 (q, 3"-OCOCH$_2$CH$_3$), 2.35 (t, 4"-OCOCH$_2$CH$_2$CH$_3$), 2.39 (br d, 2-H), 2.45 (br d, 14-H), 2.55 (s, 3'-N(CH$_3$)$_2$), 2.74 (dd, 17-H), 3.02 (dd, 2-H), 3.17 (d, 2"-H), 3.31 (dd, 2'-H), 3.40 (dd, 4-H), 3.63 (s, 4-OCH$_3$), 3.99 (br d, 5-H), 4.15 (dd, 9-H), 4.44 (dq, 5"-H), 4.45 (d, 1'-H), 4.56 (d, 4"-H), 4.80 (d, 1"-H), 5.06 (ddq, 15-H), 5.48 (br d, 3-H), 5.67 (dd, 10-H), 5.89 (ddd, 13-H), 6.12 (br dd, 12-H), 6.83 (dd, 11-H), 7.60 (br t, 3-OCO-quinoline), 7.76 (d, 3-OCO-quinoline), 7.86 (br d, 3-OCO-quinoline), 8.23 (d, 3-OCO-quinoline), 7.31 (d, 3-OCO-quinoline), 8.35 (br d, 3-OCO-quinoline), 9.42 (br s, 18-H).

Example 10

Preparation of 2'-O-Acetyl-9-O-tert-butyldimethylsilyl-3-O-(imidazol-1-yl)carbonylrokitamycin 18-Dimethylacetal (Compound Represented by Formula (VII) Wherein $R^1$ Represents Propionyl Group, $R^2$ Represents Normal Butyryl Group and $R^6$ Represents Imidazol-1-ylcarbonyl Group)

200 mg of the compound of Example 1 was added with 14 ml of THF and dissolved, further added with 320 mg of 1,1-carbonyldiimidazole, and the mixture was reacted at 40° C. for 17 hours. The reaction mixture was added with 20 ml of 10% $KHSO_4$ aqueous solution and extracted with 20 ml of chloroform. The organic layer was washed with 20 ml of saturated aqueous sodium hydrogencarbonate and then saturated brine, dried over anhydrous sodium sulfate and filtered. The filtrate was concentrated under reduced pressure and the resulting residue was purified by silica gel column chromatography (chloroform:methanol (50:1)) to obtain 220 mg of a compound.
Physicochemical Properties of the Compound (1) Molecular formula: $C_{56}H_{93}N_3O_{18}Si$; (2) Mass spectrum (FAB): m/z 1124 $(M+H)^+$; (3) Specific rotation: $[\alpha]_D^{22}$ −85° (c 1.0, MeOH); (4) $^1H$ NMR spectrum (300 MHz, $CDCl_3$) δ (ppm): 0.93 (d, 19-H), 0.97 (t, 4"-OCOCH$_2$CH$_2$CH$_3$), 1.05 (d, 6"-H), 1.14 (t, 3"-OCOCH$_2$CH$_3$), 1.16 (d, 6'-H), 1.23 (d, 16-H), 1.39 (s, 3"-CH$_3$), 1.65 (dd, 2"-Hax), 1.66 (sex, 4"-OCOCH$_2$CH$_2$CH$_3$), 1.83 (m, 8-H), 2.01 (s, 2'-OCOCH$_3$), 2.10 (dt, 14-H), 2.30 (m, 3"-OCOCH$_2$CH$_3$), 2.38 (t, 4"-OCOCH$_2$CH$_2$CH$_3$), 2.40 (s, 3'-N(CH$_3$)$_2$), 2.43 (m, 14-H), 2.56 (t, 3'-H), 2.86 (dd, 2-H), 3.00 (s, 18-OCH$_3$), 3.06 (s, 18-OCH$_3$), 3.13 (br d, 2"-Heq), 3.22 (dd, 4-H), 3.48 (s, 4-OCH$_3$), 3.83 (br d, 5-H), 4.17 (dd, 9-H), 4.30 (dd, 18-H), 4.46 (dq, 5"-H), 4.55 (d, 4"-H), 4.66 (d, 1'-H), 4.78 (d, 1"-H), 4.92 (dd, 2'-H), 5.04 (ddq, 15-H), 5.15 (br d, 3-H), 5.60 (dd, 10-H), 5.67 (ddd, 13-H), 6.03 (br dd, 12-H), 6.39 (dd, 11-H), 7.06 (br d, 3-OCO-imidazole), 7.42 (dd, 3-OCO-imidazole), 8.16 (br s, 3-OCO-imidazole).

Example 11

Preparation of 3-O-(Imidazol-1-yl) carbonylrokitamycin (Compound Represented by Formula (I) Wherein $R^1$ Represents Propionyl Group, $R^2$ Represents Normal Butyryl Group and $R^\alpha$ Represents Imidazol-1-ylcarbonyl Group)

70 mg of the compound of Example 10 was added with 5.0 ml of methanol and reacted overnight at 40° C. The reaction mixture was concentrated under reduced pressure to obtain 65 mg of oil. 65 mg of the resulting compound was added with 5.0 ml of acetonitrile and dissolved, further added with 5.0 ml of water and 22 μl of difluoroacetic acid, and the mixture was stirred overnight at room temperature. The reaction mixture was added with 15 ml of saturated aqueous sodium hydrogencarbonate and extracted with 50 ml of chloroform. The organic layer was washed with 50 ml of saturated brine, dried over anhydrous sodium sulfate and filtered. The filtrate was concentrated under reduced pressure, and the resulting residue was purified by preparative TLC (chloroform:methanol:aqueous ammonia (500:10:1)) to obtain 10 mg of a compound product. The resulting compound product consisted of a mixture of inseparable allyl-rearranged compounds. Physicochemical properties of the main compound are shown below.
Physicochemical Properties of the Compound (1) Molecular formula: $C_{46}H_{71}N_3O_{16}$; (2) Mass spectrum (TSP): m/z 922 $(M+H)^+$; (3) Specific rotation: $[\alpha]_D^{22}$ −54° (c 1.0, MeOH); (4) $^1H$ NMR spectrum (300 MHz, CDCl$_3$) δ (ppm): 0.96 (t, 4"-OCOCH$_2$CH$_2$CH$_3$), 1.07 (d, 19-H), 1.10 (d, 6"-H), 1.10 (t, 3"-OCOCH$_2$CH$_3$), 1.12 (d, 6'-H), 1.28 (d, 16-H), 1.40 (s, 3"-CH$_3$), 1.67 (sex, 4"-OCOCH$_2$CH$_2$CH$_3$), 1.89 (m, 8-H), 2.52 (s, 3'-N(CH$_3$)$_2$), 2.78 (dd, 2-H), 3.18 (dd, 4-H), 3.18 (t, 4'-H), 3.18 (d, 2"-Heq), 3.30 (dd, 2'-H), 3.50 (s, 4-OCH$_3$), 3.76 (br d, 5-H), 4.08 (br dd, 9-H), 4.46 (d, 1'-H), 4.46 (dq, 5"-H), 4.58 (d, 4"-H), 4.82 (d, 1"-H), 5.27 (ddq, 15-H), 5.22 (br d, 3-H), 7.04 (br s, 3-OCO-imidazole), 7.45 (br dd, 3-OCO-imidazole), 8.21 (br s, 3-OCO-imidazole), 9.78 (br s, 18-H).

Example 12

Preparation of 2'-O-Acetyl-9-O-tert-butyldimethylsilyl-3-O-(N-methylamino) carbonylrokitamycin 18-Dimethylacetal (Compound Represented by Formula (VIII) Wherein $R^1$ Represents Propionyl Group, $R^2$ Represents Normal Butyryl Group and $R^7$ Represents N-Methylaminocarbonyl Group)

65 mg of the compound of Example 10 was added with 1.3 ml of 2 M methylamine solution in THF and reacted at 40° C. for 2 days. The reaction mixture was concentrated under reduced pressure, and the resulting residue was purified by preparative TLC (chloroform:methanol (40:1)) to obtain 38 mg of a compound.
Physicochemical Properties of the Compound (1) Molecular formula: $C_{54}H_{94}N_2O_{18}Si$; (2) Mass spectrum (TSP): m/z 1087 $(M+H)^+$; (3) Specific rotation: $[\alpha]_D^{22}$ −90° (c 1.0, MeOH); (4) $^1H$ NMR spectrum (300 MHz, $CDCl_3$) δ (ppm): 0.92 (d, 19-H), 0.96 (t, 4"-OCOCH$_2$CH$_2$CH$_3$), 1.04 (d, 6"-H), 1.12 (t, 3"-OCOCH$_2$CH$_3$), 1.16 (d, 6'-H), 1.23 (d, 16-H), 1.39 (s, 3"-CH$_3$), 1.66 (sex, 4"-OCOCH$_2$CH$_2$CH$_3$), 1.82 (m, 8-H), 2.00 (s, 2'-OCOCH$_3$), 2.09 (dt, 14-H), 2.26 (m, 3"-OCOCH$_2$CH$_3$), 2.35 (t, 4"-OCOCH$_2$CH$_2$CH$_3$), 2.39 (s, 3'-N(CH$_3$)$_2$), 2.54 (t, 3'-H), 2.67 (dd, 2-H), 2.78 (d, 3-OCOHNCH$_3$), 3.20 (s, 18-OCH$_3$), 3.28 (s, 18-OCH$_3$), 3.44 (s, 4-OCH$_3$), 3.82 (br d, 5-H), 4.22 (dd, 9-H), 4.38 (dd, 18-H), 4.46 (dq, 5"-H), 4.55 (d, 4"-H), 4.63 (d, 1'-H), 4.78 (d, 1"-H), 4.89 (br d, 3-H), 4.93 (dd, 2'-H), 4.99 (ddq, 15-H), 5.55 (dd, 10-H), 5.72 (ddd, 13-H), 6.00 (br dd, 12H), 6.36 (dd, 11-H).

Example 13

Preparation of 3-O-(N-Methylamino) carbonylrokitamycin (Compound Represented by Formula (I) Wherein $R^1$ Represents Propionyl Group, $R^2$ Represents Normal Butyryl Group and $R^\alpha$ Represents N-Methylaminocarbonyl Group)

70 mg of the compound of Example 12 was added with 5.0 ml of methanol and reacted overnight at 40° C. The reaction mixture was concentrated under reduced pressure to obtain 62 mg of oil. 62 mg of the resulting compound was added with 6.0 ml of acetonitrile and dissolved, further added with 6.0 ml of water and 22 μl of difluoroacetic acid, and the mixture was stirred overnight at 40° C. The reaction mixture was added with 15 ml of saturated aqueous sodium hydrogencarbonate and extracted with 50 ml of chloroform. The organic layer was washed with 50 ml of saturated brine, dried over anhydrous sodium sulfate and filtered. The filtrate was concentrated under reduced pressure, and the resulting residue was purified by preparative TLC (chloroform:methanol (200:15)) to obtain 12 mg of a compound product. The compound product consisted of a mixture of inseparable allyl-rearranged compounds. Physicochemical properties of the main compound are shown below.
Physicochemical Properties of the Compound (1) Molecular formula: $C_{44}H_{72}N_2O_{16}$; (2) Mass spectrum (FAB): m/z 885 $(M+H)^+$; (3) Specific rotation: $[\alpha]_D^{22}$ −52° (c 0.6, MeOH); (4) $^1H$ NMR spectrum (300 MHz, CDCl$_3$) δ (ppm): 0.96 (t, 4"-OCOCH$_2$CH$_2$CH$_3$), 1.03 (d, 19-H), 1.07 (d, 6"-H), 1.11 (t, 3"-OCOCH$_2$CH$_3$), 1.13 (d, 6'-H), 1.19 (d, 16-H), 1.40 (s, 3"-CH$_3$), 1.67 (dd, 2"-Hax), 1.67 (sex, 4"-OCOCH$_2$CH$_2$CH$_3$), 1.88 (m, 8-H), 1.88 (m, 14-H), 2.14 (br d, 2-H), 2.19 (dt, 14-H), 2.27 (m, 3"-OCOCH$_2$CH$_3$), 2.35 (t, 4"-OCOCH$_2$CH$_2$CH$_3$), 2.51 (s, 3'-N(CH$_3$)$_2$), 2.82 (d, 3-OCOHNCH$_3$), 2.75 (dd, 2-H), 3.18 (dd, 4-H), 3.18 (t, 4'-H), 3.18 (d, 2"-Heq), 3.30 (dd, 2'-H), 3.58 (s, 4-OCH$_3$), 3.79 (br d, 5-H), 4.17 (br dd, 9-H), 4.34 (d, 1'-H), 4.47 (dq, 5"-H), 4.57 (d, 4"-H), 4.83 (d, 1"-H), 5.06 (ddq, 15-H), 5.18 (br d, 3-H), 5.55 (dd, 10-H), 6.06 (br dd, 12-H), 6.25 (dd, 11-H), 5.63 (dd, 13-H), 9.64 (s, 18-H).

Example 14

Preparation of 2'-O-Acetyl-9-O-tert-butyldimethylsilyl-3-O-(N,N-dimethylamino)carbonylrokitamycin 18-Dimethylacetal (Compound Represented by Formula (VIII) Wherein R$^1$ Represents Propionyl Group, R$^2$ Represents Normal Butyryl Group and R$^7$ Represents N,N-Dimethylaminocarbonyl Group)

100 mg of the compound of Example 10 was added with 1.0 ml of methylene chloride and dissolved, further added with 1.0 ml of 4 M dimethylamine solution in methylene chloride, and the mixture was reacted at 40° C. for 3 days. The reaction mixture was concentrated under reduced pressure, and the resulting residue was purified by preparative TLC (hexane:ethyl acetate (50:1)) to obtain 65 mg of a compound.
Physicochemical Properties of the Compound
(1) Molecular formula: C$_{55}$H$_{96}$N$_2$O$_{18}$Si; (2) Mass spectrum (FAB): m/z 1101 (M+H)$^+$; (3) Specific rotation: [α]$_D^{22}$ −81° (c 1.0, CHCl$_3$); (4) $^1$H NMR spectrum (300 MHz, CDCl$_3$) δ (ppm): 0.92 (d, 19-H), 0.96 (t, 4"-OCOCH$_2$CH$_2$CH$_3$), 1.05 (d, 6"-H), 1.14 (t, 3"-OCOCH$_2$CH$_3$), 1.18 (d, 6'-H), 1.24 (d, 16-H), 1.40 (s, 3"-CH$_3$), 1.66 (dd, 2"-Hax), 1.67 (sex, 4"-OCOCH$_2$CH$_2$CH$_3$), 1.83 (m, 8-H), 2.00 (s, 2'-OCOCH$_3$), 2.11 (dt, 14-H), 2.22 (dd, 2-H), 2.28 (m, 3"-OCOCH$_2$CH$_3$), 2.36 (t, 4"-OCOCH$_2$CH$_2$CH$_3$), 2.40 (s, 3'-N(CH$_3$)$_2$), 2.56 (t, 3'-H), 2.66 (dd, 2-H), 2.70 (br s, 3-OCON(CH$_3$)$_2$), 3.20 (s, 18-OCH$_3$), 3.26 (s, 18-OCH$_3$), 3.42 (s, 4-OCH$_3$), 3.82 (br d, 5-H), 4.22 (dd, 9-H), 4.38 (dd, 18-H), 4.47 (dq, 5"-H), 4.55 (d, 4"-H), 4.66 (d, 1'-H), 4.79 (d, 1"-H), 4.86 (br d, 3-H), 4.94 (dd, 2'-H), 4.94 (ddq, 15-H), 5.54 (dd, 10-H), 5.76 (ddd, 13-H), 6.00 (br dd, 12-H), 6.33 (dd, 11-H).

Example 15

Preparation of 3-O-(N,N-Dimethylamino)carbonylrokitamycin (Compound Represented by Formula (I) Wherein R$^1$ Represents Propionyl Group, R$^2$ Represents Normal Butyryl Group and R$^α$ Represents N,N-Dimethylaminocarbonyl Group)

150 mg of the compound of Example 14 was added with 15 ml of methanol and reacted overnight at 40° C. The reaction mixture was concentrated under reduced pressure to obtain 130 mg of oil. 130 mg of the resulting compound was added with 13 ml of acetonitrile and dissolved, further added with 13 ml of water and 46 μl of difluoroacetic acid, and the mixture was stirred overnight at 40° C. The reaction mixture was added with 30 ml of saturated aqueous sodium hydrogencarbonate and extracted with 50 ml of chloroform. The organic layer was washed with 50 ml of saturated brine, dried over anhydrous sodium sulfate and filtered. The filtrate was concentrated under reduced pressure, and the resulting residue was purified by preparative TLC (chloroform:methanol (20:1)) to obtain 30 mg of a compound product. The compound product consisted of a mixture of inseparable allyl-rearranged compounds. Physicochemical properties of the main compound are shown below.
Physicochemical Properties of the Compound
(1) Molecular formula: C$_{45}$H$_{74}$N$_2$O$_{16}$; (2) Mass spectrum (TSP): m/z 899 (M+H)$^+$; (3) Specific rotation: [α]$_D^{22}$ −61° (c 1.0, MeOH); (4) $^1$H NMR spectrum (300 MHz, CDCl$_3$) δ (ppm): 0.95 (t, 4"-OCOCH$_2$CH$_2$CH$_3$), 1.02 (d, 19-H), 1.06 (d, 6"-H), 1.10 (t, 3"-OCOCH$_2$CH$_3$), 1.12 (d, 6'-H), 1.18 (d, 16-H), 1.38 (s, 3"-CH$_3$), 1.66 (dd, 2"-Hax), 1.67 (sex, 4"-OCOCH$_2$CH$_2$CH$_3$), 1.87 (m, 8-H), 1.88 (dt, 14-H), 2.15 (br d, 2-H), 2.26 (m, 3"-OCOCH$_2$CH$_3$), 2.34 (dd, 3'-H), 2.35 (t, 4"-OCOCH$_2$CH$_2$CH$_3$), 2.50 (s, 3'-N(CH$_3$)$_2$), 2.91 (s, 3-OCON(CH$_3$)$_2$), 2.76 (dd, 2-H), 3.16 (dd, 4-H), 3.16 (d, 2"-Heq), 3.18 (t, 4'-H), 3.35 (dd, 2'-H), 3.54 (s, 4-OCH$_3$), 3.72 (br d, 5-H), 4.15 (br dd, 9-H), 4.30 (d, 1'-H), 4.49 (dq, 5"-H), 4.56 (d, 4"-H), 4.82 (d, 1"-H), 5.01 (ddq, 15-H), 5.13 (br d, 3-H), 5.55 (dd, 10-H), 6.05 (br dd, 12-H), 6.23 (dd, 11-H), 6.27 (dd, 13-H), 9.64 (br s, 18-H).

Example 16

Preparation of 2'-O-Acetyl-3-O-(N-benzylamino)carbonyl-9-O-tert-butyldimethylsilylrokitamycin 18-Dimethylacetal (Compound Represented by Formula (VIII) Wherein R$^1$ Represents Propionyl Group, R$^2$ Represents Normal Butyryl Group and R$^7$ Represents N-Benzylaminocarbonyl Group)

206 mg of the compound of Example 10 was added with 4.0 ml of THF and dissolved, further added with 857 mg of benzylamine, and the mixture was reacted at 45° C. for 2 days. The reaction mixture was concentrated under reduced pressure, and the resulting residue was purified by preparative TLC (chloroform:methanol (50:1)) to obtain 165 mg of a compound.
Physicochemical Properties of the Compound
(1) Molecular formula: C$_{60}$H$_{98}$N$_2$O$_{18}$Si; (2) Mass spectrum (TSP): m/z 1163 (M+H)$^+$; (3) Specific rotation: [α]$_D^{22}$ −60° (c 1.0, CHCl$_3$); (4) $^1$H NMR spectrum (300 MHz, CDCl$_3$) δ (ppm): 0.96 (d, 19-H), 1.00 (t, 4"-OCOCH$_2$CH$_2$CH$_3$), 1.08 (d, 6"-H), 1.14 (t, 3"-OCOCH$_2$CH$_3$), 1.20 (d, 6'-H), 1.28 (d, 16-H), 1.44 (s, 3"-CH$_3$), 1.70 (sex, 4"-OCOCH$_2$CH$_2$CH$_3$), 1.86 (m, 8-H), 2.03 (s, 2'-OCOCH$_3$), 2.14 (dt, 14-H), 2.30 (m, 3"-OCOCH$_2$CH$_3$), 2.40 (t, 4"-OCOCH$_2$CH$_2$CH$_3$), 2.44 (s, 3'-N(CH$_3$)$_2$), 2.59 (t, 3'-H), 2.74 (dd, 2-H), 3.24 (s, 18-OCH$_3$), 3.29 (s, 18-OCH$_3$), 3.50 (s, 4-OCH$_3$), 3.88 (br d, 5-H), 4.27 (dd, 9-H), 4.48 (m, CH$_2$C$_6$H$_5$), 4.48 (dd, 18-H), 4.51 (dq, 5"-H), 4.59 (d, 4"-H), 4.70 (d, 1'-H), 4.82 (d, 1"-H), 4.97 (dd, 2'-H), 4.99 (br d, 3-H), 5.08 (ddq, 15-H), 5.59 (dd, 10-H), 5.76 (ddd, 13-H), 6.02 (br dd, 12-H), 6.42 (dd, 11-H), 7.35 (m, CH$_2$C$_6$H$_5$).

Example 17

Preparation of 3-O-(N-Benzylamino)carbonylrokitamycin (Compound Represented by Formula (I) Wherein R$^1$ Represents Propionyl Group, R$^2$ Represents Normal Butyryl Group and R$^α$ Represents N-Benzylaminocarbonyl Group)

150 mg of the compound of Example 16 was added with 16.5 ml of methanol and reacted overnight at 40° C. The reaction mixture was concentrated under reduced pressure to obtain 145 mg of oil. 145 mg of the resulting compound was added with 15 ml of acetonitrile and dissolved, further added with 15 ml of water and 49 μl of difluoroacetic acid, and the mixture was stirred overnight at 40° C. The reaction mixture was added with 30 ml of saturated aqueous sodium hydrogencarbonate and extracted with 50 ml of chloroform. The organic layer was washed with 50 ml of saturated brine, dried over anhydrous sodium sulfate and filtered. The filtrate was concentrated under reduced pressure, and the resulting residue was purified by preparative TLC (chloroform:methanol (10:1)) to obtain 59 mg of a compound.

Physicochemical Properties of the Compound (1) Molecular formula: $C_{50}H_{76}N_2O_{16}$; (2) Mass spectrum (FAB): m/z 961 (M+H)$^+$; (3) Specific rotation: $[\alpha]_D^{22}$ −31° (c 1.0, MeOH); (4) $^1$H NMR spectrum (300 MHz, CDCl$_3$) δ (ppm): 0.96 (t, 4"-OCOCH$_2$CH$_2$CH$_3$), 0.98 (d, 19-H), 1.07 (d, 6"-H), 1.09 (t, 3"-OCOCH$_2$CH$_3$), 1.12 (d, 6'-H), 1.25 (d, 16-H), 1.40 (s, 3"-CH$_3$), 1.67 (sex, 4"-OCOCH$_2$CH$_2$CH$_3$), 1.88 (m, 8-H), 2.12 (dt, 14-H), 2.27 (t, 3'-H), 2.28 (m, 3"-OCOCH$_2$CH$_3$), 2.36 (t, 4"-OCOCH$_2$CH$_2$CH$_3$), 2.24 (dd, 2-H), 2.44 (m, 14-H), 2.52 (s, 3'-N(CH$_3$)$_2$), 2.74 (dd, 2-H), 3.17 (dd, 4-H), 3.18 (m, 5'-H), 3.32 (dd, 2'-H), 3.53 (s, 4-OCH$_3$), 3.88 (br d, 5-H), 4.12 (br dd, 9-H), 4.38 (d, 1'-H), 4.44 (dq, 5"-H), 4.47 (m, CH$_2$C$_6$H$_5$), 4.58 (d, 4"-H), 4.81 (d, 1"-H), 5.01 (br d, 3-H), 5.03 (ddq, 15-H), 5.60 (dd, 10-H), 5.77 (ddd, 13-H), 6.03 (br dd, 12-H), 6.33 (dd, 11-H), 7.33 (m, CH$_2$C$_6$H$_5$), 9.62 (br s, 18-H).

Example 18

Preparation of 2'-O-Acetyl-9-O-tert-butyldimethylsilyl-4"-O-isoamyl-3"-O-methylleucomycin V 18-Dimethylacetal (Compound Represented by Formula (III) Wherein R$^1$ Represents Methyl Group, R$^2$ Represents Isoamyl Group, R$^3$ Represents tert-Butyldimethylsilyl Group and R$^4$ and R$^5$ Both Represent Methyl Group)

510 mg of 9,18-di-O-tert-butyldimethylsilyl-4"-O-isoamyl-3"-O-methylleucomycin V 3,18-acetal (Compound 28 described in U.S. Pat. No. 5,407,918) obtained from leucomycin A$_7$ (LM-A$_7$) was added with 2.5 ml of 1 M tetrabutylammonium fluoride solution in THF and reacted at room temperature for 15 minutes. The reaction mixture was added with 50 ml of methylene chloride and washed twice with 50 ml of saturated brine. Then, the organic layer was dried over anhydrous sodium sulfate and filtered. The filtrate was concentrated under reduced pressure, and the resulting residue was purified by silica gel column chromatography (chloroform:methanol (10:1)) to obtain 440 mg of 9-O-tertbutyldimethylsilyl-4"-O-isoamyl-3"-O-methylleucomycin V.

50 g of the resulting compound was added with 1.0 ml of methanol and dissolved, further added with 1.0 ml of methyl orthoformate and 30 mg of PPTS, and the mixture was stirred overnight at 30° C. The reaction mixture was added with 50 ml of methylene chloride and washed successively with each 50 ml of saturated aqueous sodium hydrogencarbonate and saturated brine. The organic layer was dried over anhydrous sodium sulfate and the filtrate was concentrated under reduced pressure. Without purification, the resulting oil was added with 1.0 ml of acetonitrile and dissolved, further added with 25 μl of acetic anhydride, and the mixture was stirred overnight at 30° C. The reaction mixture was added with 50 ml of methylene chloride and washed successively with each 50 ml of saturated aqueous sodium hydrogencarbonate and saturated brine. The organic layer was dried over anhydrous sodium sulfate. Then, the filtrate was concentrated under reduced pressure, and the resulting residue was purified by silica gel column chromatography (hexane:ethyl acetate (1:1)) to obtain 51 g of a compound.

Physicochemical Properties of the Compound (1) Molecular formula: $C_{51}H_{93}NO_{15}Si$; (2) Mass spectrum (SIMS): m/z 987 (M)$^+$; (3) Specific rotation: $[\alpha]_D^{24}$ −88° (c 1.0, CHCl$_3$); (4) $^1$H NMR spectrum (300 MHz, CDCl$_3$) δ (ppm): 0.86 (d, 4"-OCH$_2$CH$_2$CH(CH$_3$)$_2$), 0.91 (d, 19-H), 1.17 (d, 6-H), 1.20 (s, 3"-CH$_3$), 1.20 (d, 6"-H), 1.28 (d, 6-H), 1.48 (m, 4"-OCH$_2$CH$_2$CH(CH$_3$)$_2$), 1.98 (s, 2'-OCOCH$_3$), 2.18 (br d, 2-H), 2.18 (br d, 2"-Hax), 2.40 (s, 3'-N(CH$_3$)$_2$), 2.43 (br d, 14-H), 2.72 (d, 4"-H), 2.86 (dd, 4-H), 3.59 (dt, 4"-OCH$_2$CH$_2$CH(CH$_3$)$_2$), 3.96 (br d, 18-H), 4.18 (dd, 9-H), 4.43 (dq, 5"-H), 4.54 (br dd, 5-H), 4.68 (d, 1'-H), 4.76 (d, 1"-H), 4.91 (dd, 2'-H), 5.05 (ddq, 15-H), 5.50 (ddd, 13-H), 5.63 (dd, 10-H), 6.05 (dd, 11-H), 6.05 (br dd, 12-H).

Example 19

Preparation of 2'-O-Acetyl-9-O-tertbutyldimethylsilyl-4"-O-isoamyl-3,3"-di-O-methylleucomycin V 18-Dimethylacetal (Compound Represented by Formula (VII) Wherein R$^1$ Represents Methyl Group, R$^2$ Represents Isoamyl Group and R$^6$ Represents Methyl Group)

45 mg of the compound of Example 18 was added with 450 μl of DMSO and dissolved, further added with 11 μl of methyl iodide and 40 mg of KOH, and then the mixture was reacted at room temperature for 5 hours. The reaction mixture was added with 50 ml of methylene chloride and washed twice with 50 ml of saturated brine. Then, the organic layer was dried over anhydrous sodium sulfate and filtered. The filtrate was concentrated under reduced pressure, and the resulting residue was purified by silica gel column chromatography (hexane:ethyl acetate (1:1)) to obtain 25 mg of a compound.

Physicochemical Properties of the Compound (1) Molecular formula: $C_{52}H_{95}NO_{15}Si$; (2) Mass spectrum (SIMS): m/z 1001 (M)$^+$; (3) Specific rotation: $[\alpha]_D^{24}$ −98° (c 1.0, CHCl$_3$); (4) $^1$H NMR spectrum (300 MHz, CDCl$_3$) δ (ppm): 0.86 (d, 4"-OCH$_2$CH$_2$CH(CH$_3$)$_2$), 0.92 (d, 19-H), 1.18 (d, 6'-H), 1.20 (s, 3"-CH$_3$), 1.20 (d, 6"-H), 1.28 (d, 16-H), 1.48 (m, 4"-OCH$_2$CH$_2$CH(CH$_3$)$_2$), 1.67 (m, 4"-OCH$_2$CH$_2$CH(CH$_3$)$_2$), 1.82 (m, 8-H), 1.98 (s, 2'-OCOCH$_3$), 2.07 (dt, 14-H), 2.18 (br d, 2-H), 2.18 (br d, 2"-Hax), 2.40 (s, 3'-N(CH$_3$)$_2$), 2.46 (br d, 14-H), 2.72 (d, 4"-H), 2.93 (br d, 4-H), 3.37 (s, 4-OCH$_3$), 3.44 (s, 3-OCH$_3$), 3.59 (dt, 4"-OCH$_2$CH$_2$CH(CH$_3$)$_2$), 3.71 (br d, 3-H), 4.01 (br d, 18-H), 4.21 (dd, 9-H), 4.41 (dq, 5"-H), 4.48 (br dd, 5-H), 4.70 (d, 1'-H), 4.77 (d, 1"-H), 4.88 (dd, 2'-H), 5.26 (ddq, 15-H), 5.48 (ddd, 13-H), 5.61 (dd, 10-H), 5.98 (dd, 11-H), 5.98 (br dd, 12-H).

Example 20

Preparation of 4"-O-Isoamyl-3,3"-di-O-methylleucomycin V (Compound Represented by Formula (I) Wherein R$^1$ Represents Methyl Group, R$^2$ Represents Isoamyl Group and R$^\alpha$ Represents Methyl Group)

23 g of the compound of Example 19 was added with 2.3 ml of methanol and reacted overnight at room temperature. The methanol was concentrated under reduced pressure. Without purification, the resulting oil was added with 2.0 ml of acetonitrile and dissolved, added with 2.0 ml of water and 8.3 μl of difluoroacetic acid, and then the mixture was stirred overnight at 40° C. The reaction mixture was added with 50 ml of methylene chloride and washed successively with each 50 ml of saturated aqueous sodium hydrogencarbonate and saturated brine. The organic layer was dried over anhydrous sodium sulfate. The filtrate was concentrated under reduced pressure, and the resulting residue was purified by silica gel column chromatography (chloroform:methanol (10:1)) to obtain 4.0 mg of a compound.

Physicochemical Properties of the Compound (1) Molecular formula: $C_{42}H_{73}NO_{13}$; (2) Mass spectrum (SIMS): m/z 799 (M)$^+$; (3) Specific rotation: $[\alpha]_D^{24}$ −65° (c 0.4, $CH_3OH$); (4) $^1H$ NMR spectrum (300 MHz, $CDCl_3$) δ (ppm): 0.87 (d, 4"-$OCH_2CH_2CH(CH_3)_2$), 1.00 (d, 19-H), 1.17 (d, 6'-H), 1.21 (d, 6"-H), 1.22 (s, 3"-$CH_3$), 1.30 (d, 16-H), 1.55 (m, 4"-$OCH_2CH_2CH(CH_3)_2$), 1.67 (m, 4"-$OCH_2CH_2CH(CH_3)_2$), 1.88 (m, 8-H), 2.13 (dt, 14-H), 2.21 (br d, 2-H), 2.21 (br d, 2"-Hax), 2.29 (t, 3'-H), 2.32 (br dd, 17-H), 2.47 (br d, 14-H), 2.55 (s, 3'-$N(CH_3)_2$), 2.76 (dd, 2-H), 2.76 (d, 4"-H), 2.90 (br dd, 17-H), 3.23 (s, 3"-$OCH_3$), 3.48 (s, 4-$OCH_3$), 3.49 (s, 3-$OCH_3$), 3.60 (dt, 4"-$OCH_2CH_2CH(CH_3)_2$), 3.95 (br dd, 5-H), 4.08 (dd, 9-H), 4.41 (dq, 5"-H), 4.52 (d, 1'-H), 4.87 (d, 1"-H), 5.01 (ddq, 15-H), 5.60 (ddd, 13-H), 5.69 (dd, 10-H), 6.09 (br dd, 12-H), 6.28 (dd, 11-H), 9.76 (br s, 18-H).

Example 21

Preparation of 2'-O-Acetyl-9-O-tert-butyldimethylsilylleucomycin A$_7$ 18-Dimethylacetal (Compound Represented by Formula (III) Wherein R$^1$ Represents Hydrogen Atom, R$^2$ Represents Propionyl Group, R$^3$ Represents tert-Butyldimethylsilyl Group and R$^4$ and R$^5$ Both Represent Methyl Group)

10.9 g of LM-A$_7$, 4.9 g of TBDMSCl and 4.8 g of imidazole were stirred overnight in 130 ml of DMF at room temperature. The reaction mixture was added with 8.0 ml of methanol and extracted with 2.5 L of ethyl acetate. The organic layer was washed successively with 2.5 L each of water, saturated aqueous sodium hydrogencarbonate and saturated brine, dried over anhydrous sodium sulfate and filtered. The filtrate was concentrated under reduced pressure, and the resulting residue was purified by silica gel column chromatography (hexane:acetone (7:1→5:1→1:1)) to obtain 6.84 g of 9-O-tert-butyldimethylsilylleucomycin A$_7$.

6.84 g of the resulting compound was added with 100 ml of methanol and dissolved, further added with 100 ml of methyl orthoformate and 4.44 g of PPTS, and then the mixture was stirred overnight at 45° C. The reaction mixture was added with saturated aqueous sodium hydrogencarbonate and concentrated under reduced pressure. Then, the residue was diluted with 200 ml of chloroform and washed with 100 ml of saturated brine. The organic layer was dried over anhydrous sodium sulfate and filtered, and the filtrate was concentrated under reduced pressure. Without purification, the resulting oil was added with 220 ml of acetonitrile and dissolved, further added with 3.8 ml of acetic anhydride and stirred overnight at 50° C. The reaction mixture was added with saturated aqueous sodium hydrogencarbonate and concentrated under reduced pressure. Then, the resulting residue was extracted with 200 ml of ethyl acetate. The organic layer was washed with 100 ml of saturated brine, dried over anhydrous sodium sulfate and filtered. The filtrate was concentrated under reduced pressure, and the resulting residue was purified by silica gel column chromatography (hexane:ethyl acetate (1:1)) to obtain 6.17 g of a compound.

Physicochemical Properties of the Compound (1) Molecular formula: $C_{48}H_{85}NO_{16}Si$; (2) Mass spectrum (FAB$^+$): m/z 960 (M+H)$^+$; (3) Specific rotation: $[\alpha]_D^{25}$ −103° (c 1.0, $CH_3OH$); (4) $^1H$ NMR spectrum (300 MHz, $CDCl_3$) δ (ppm): 0.68 (br t, 7-H), 0.93 (d, 19-H), 1.10 (s, 3"-$CH_3$), 1.11 (d, 6"-H), 1.16 (t, 4"-$OCOCH_2CH_3$), 1.26 (d, 6'-H), 1.29 (d, 16-H), 1.44 (br dt, 7-H), 1.69 (br t, 6-H), 1.82 (dd, 2"-Hax), 2.00 (d, 2"-Heq), 2.01 (s, 2'-$OCOCH_3$), 2.07 (dt, 14-H), 2.19 (br d, 2-H), 2.39 (s, 3'-$N(CH_3)_2$), 2.42 (m, 4"-$OCOCH_2CH_3$), 2.62 (dd, 2-H), 2.70 (t, 3'-H), 2.95 (d, 4-H), 3.25 (s, 18-$OCH_3$), 3.30 (t, 4'-H), 3.32 (dq, 5'-H), 3.38 (s, 18-$OCH_3$), 3.44 (s, 4-$OCH_3$), 3.72 (br d, 3-H), 4.04 (d, 5-H), 4.22 (dd, 9-H), 4.37 (dq, 5"-H), 4.49 (dd, 18-H), 4.60 (d, 4"-H), 4.73 (d, 1'-H), 4.98 (dd, 2'-H), 5.07 (d, 1"-H), 5.27 (ddq, 15-H), 5.49 (ddd, 13-H), 5.62 (dd, 10-H), 5.95 (br dd, 12-H), 6.02 (dd, 11-H).

Example 22

Preparation of 2'-O-Acetyl-9-O-tert-butyldimethylsilyl-3-O-methylleucomycin A$_7$ 18-Dimethylacetal (Compound Represented by Formula (VII) Wherein R$^1$ Represents Hydrogen Atom, R$^2$ Represents Propionyl Group and R$^6$ Represents Methyl Group)

40 mg of the compound of Example 21 was added with 800 μl of DMSO and dissolved, further added with 13 μl of methyl iodide and 41 mg of KOH, and then the mixture was reacted at room temperature for 1 hour. The reaction mixture was added with 10 ml of water and extracted with 50 ml of diethyl ether. The organic layer was washed with 10 ml of saturated brine, dried over anhydrous sodium sulfate and filtered. The filtrate was concentrated under reduced pressure, and the resulting residue was purified by preparative TLC (hexane:ethyl acetate (1:1)) to obtain 16 mg of a compound.

Physicochemical Properties of the Compound (1) Molecular formula: $C_{49}H_{87}NO_{16}Si$; (2) Mass spectrum (TSP): m/z 974 (M+H)$^+$; (3) Specific rotation: $[\alpha]_D^{23}$ −106° (c 0.82, $CHCl_3$); (4) $^1H$ NMR spectrum (300 MHz, $CDCl_3$) δ (ppm): 0.96 (d, 19-H), 0.97 (br t, 7-H), 1.10 (s, 3"-$CH_3$), 1.11 (d, 6"-H), 1.16 (t, 4"-$OCOCH_2CH_3$), 1.26 (d, 6'-H), 1.28 (d, 16-H), 1.30 (br dt, 7-H), 1.77 (m, 8-H), 1.82 (dd, 2"-Hax), 1.99 (s, 2'-$OCOCH_3$), 1.99 (br d, 2-H), 2.01 (d, 2"-Heq), 2.14 (dt, 14-H), 2.38 (s, 3'-$N(CH_3)_2$), 2.42 (m, 4"-$OCOCH_2CH_3$), 2.43 (br d, 14-H), 2.66 (dd, 2-H), 2.71 (t, 3'-H), 2.87 (dd, 4'-H), 3.26 (s, 18-$OCH_3$), 3.31 (s, 18-$OCH_3$), 3.38 (s, 4-$OCH_3$), 3.39 (s, 3-$OCH_3$), 3.96 (br d, 5-H), 4.18 (dd, 9-H), 4.38 (dq, 5"-H), 4.53 (dd, 18-H), 4.60 (d, 4"-H), 4.70 (d, 1'-H), 4.99 (dd, 2'-H), 5.06 (d, 1"-H), 5.30 (ddq, 15-H), 5.50 (ddd, 13-H), 5.62 (dd, 10-H), 6.03 (br dd, 12-H), 6.08 (dd, 11-H).

Example 23

Preparation of 3-O-Methylleucomycin A$_7$ (Compound Represented by Formula (I) Wherein R$^1$ Represents Hydrogen Atom, R$^2$ Represents Propionyl Group and R$^\alpha$ Represents Methyl Group)

23 mg of the compound of Example 22 was added with 2.3 ml of methanol and reacted overnight at room temperature. The methanol was concentrated under reduced pressure. Without purification, the resulting oil was added with 2.0 ml of acetonitrile and dissolved, further added with 2.0 ml of water and 8.3 μl of difluoroacetic acid, and then the mixture was stirred overnight at 40° C. The reaction mixture was added with 50 ml of methylene chloride and washed successively with each 50 ml of saturated aqueous sodium hydrogencarbonate and saturated brine. The organic layer was dried over anhydrous sodium sulfate. The filtrate was concentrated under reduced pressure, and the resulting residue was purified by silica gel column chromatography (chloroform:methanol (10:1)) to obtain 4.0 mg of a compound.

Physicochemical Properties of the Compound (1) Molecular formula: $C_{39}H_{65}NO_{14}$; (2) Mass spectrum (SIMS): m/z 771 (M)$^+$; (3) Specific rotation: $[\alpha]_D^{24}$ −167° (c 0.40, $CH_3OH$); (4) $^1H$ NMR spectrum (300 MHz, $CDCl_3$) δ (ppm): 1.05 (d, 19-H), 1.11 (d, 6'-H), 1.14 (t, 4"-OCOCH$_2$CH$_3$), 1.22 (d, 6"-H), 1.33 (ddd, 7-H), 1.81 (dd, 2"-Hax), 1.98 (br d, 2"-Heq), 2.15 (br d, 14-H), 2.42 (m, 4"-OCOCH$_2$CH$_3$), 2.47 (s, 3'-N(CH$_3$)$_2$), 2.70 (dd, 2-H), 2.93 (dd, 4-H), 2.93 (dq, 17-H), 3.25 (dq, 5'-H), 3.43 (s, 4-OCH$_3$), 3.45 (s, 3-OCH$_3$), 3.54 (t, 4'-H), 3.79 (br dd, 5-H), 4.11 (dd, 9-H), 4.36 (d, 1'-H), 4.45 (dq, 5"-H), 4.59 (d, 4"-H), 5.05 (d, 1"-H), 5.13 (ddq, 15-H), 5.63 (dd, 10-H), 5.63 (ddd, 13-H), 6.05 (br dd, 12-H), 6.23 (dd, 11-H), 9.77 (br s, 18-H).

Example 24

Preparation of 2'-O-Acetyl-3-O-benzoyl-9-O-tert-butyldimethylsilylleucomycin A$_7$ 18-Dimethylacetal (Compound Represented by Formula (VII) Wherein R$^1$ Represents Hydrogen Atom, R$^2$ Represents Propionyl Group and R$^6$ Represents Benzoyl Group)

92.8 mg of the compound of Example 21 was added with 1.0 ml of dichloromethane and dissolved, further added with 120 μl of pyridine, 78.0 μl of benzoyl chloride and 14.5 mg of 4-dimethylaminopyridine, and the mixture was reacted at room temperature for 3 days. The reaction mixture was added with 20 ml of saturated aqueous sodium hydrogencarbonate and extracted with 50 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (3:1→2:1)) to obtain 87.0 mg of a compound.

Physicochemical Properties of the Compound (1) Molecular formula: $C_{55}H_{89}NO_{17}Si$; (2) Mass spectrum (FAB): m/z 1064 (M+H)$^+$; (3) Specific rotation: $[\alpha]_D^{23}$ −68° (c 0.62, $CHCl_3$); (4) $^1H$ NMR spectrum (300 MHz, $CDCl_3$) δ (ppm): 0.86 (m, 7-H), 0.95 (d, 19-H), 1.06 (d 6'-H), 1.10 (d, 6"-H), 1.11 (s, 3"-CH$_3$), 1.16 (t, 4"-OCOCH$_2$CH$_3$), 1.23 (d, 16-H), 1.37 (ddd, 7-H), 1.50 (br t, 17-H), 1.66 (br t, 17-H), 1.81 (dd, 2"-Hax), 1.82 (m, 8-H), 1.95 (d, 2"-Heq), 2.03 (s, 2'-OCOCH$_3$), 2.13 (dt, 14-H), 2.36 (dd, 2-H), 2.39 (s, 3'-N(CH$_3$)$_2$), 2.42 (q, 4"-OCOCH$_2$CH$_3$), 2.43 (q, 4"-OCOCH$_2$CH$_3$), 2.66 (t, 3'-H), 2.83 (dd, 2-H), 3.05 (s, 18-OCH$_3$), 3.09 (s, 18-OCH$_3$), 3.20 (dd, 4-H), 3.24 (t, 4'-H), 3.47 (s, 4-OCH$_3$), 3.83 (br d, 5-H), 4.17 (br d, 18-H), 4.25 (dd, 9-H), 4.37 (dq, 5"-H), 4.59 (d, 4"-H), 4.72 (d, 1'-H), 4.97 (dd, 2'-H), 4.99 (d, 1"-H), 4.99 (ddq, 15-H), 5.25 (br d, 3-H), 5.61 (dd, 10-H), 5.76 (ddd, 13-H), 6.06 (br dd, 12-H), 6.38 (dd, 11-H), 7.41 (br t, 3-OCOC$_6$H$_5$), 7.53 (tt, 3-OCOC$_6$H$_5$), 8.06 (br d, 3-OCOC$_6$H$_5$).

Example 25

Preparation of 3-O-Benzoylleucomycin A$_7$ (Compound Represented by Formula (I) Wherein R$^1$ Represents Hydrogen Atom, R$^2$ Represents Propionyl Group and R$^\alpha$ Represents Benzoyl Group)

86.1 mg of the compound of Example 24 was added with 4.0 ml of methanol:water (9:1) and reacted overnight at 45° C. The reaction mixture was concentrated under reduced pressure, and the resulting residue was purified by silica gel column chromatography (chloroform:methanol (350:1→100:1)) to obtain 72.4 mg of a compound. 70.1 mg of this compound was added with 11 ml of acetonitrile and dissolved, further added with 11 ml of water and 25.0 μl of difluoroacetic acid and stirred at room temperature for 2 days. The reaction mixture was added with 30 ml of saturated aqueous sodium hydrogencarbonate and extracted with 80 ml of chloroform. The organic layer was washed with 50 ml of saturated brine, dried over anhydrous sodium sulfate and filtered. The filtrate was concentrated under reduced pressure, and the resulting residue was purified by preparative TLC (chloroform:methanol (20:1)) to obtain 28.6 mg of a compound.

Physicochemical Properties of the Compound (1) Molecular formula: $C_{45}H_{67}NO_{15}$; (2) Mass spectrum (FAB): m/z 862 (M+H)$^+$; (3) Specific rotation: $[\alpha]_D^{23}$ −21° (c 0.37, $CHCl_3$); (4) $^1H$ NMR spectrum (300 MHz, $CDCl_3$) δ (ppm): 1.01 (d, 19-H), 1.09 (s, 3"-CH$_3$), 1.10 (d, 6'-H), 1.10 (d, 6"-H), 1.16 (t, 4"-OCOCH$_2$CH$_3$), 1.23 (d, 16-H), 1.45 (br ddd, 17-H), 1.80 (dd, 2"-Hax), 1.91 (m, 8-H), 1.95 (d, 2"-Heq), 2.13 (dt, 14-H), 2.34 (br dd, 17-H), 2.38 (br d, 2-H), 2.42 (q, 4"-OCOCH$_2$CH$_3$), 2.43 (q, 4"-OCOCH$_2$CH$_3$), 2.49 (s, 3'-N(CH$_3$)$_2$), 2.74 (br dd, 17-H), 2.91 (dd, 2-H), 3.19 (m, 5'-H), 3.22 (t, 4'-H), 3.31 (dd, 4-H), 3.52 (dd, 2'-H), 3.56 (s, 4-OCH$_3$), 3.81 (br d, 5-H), 4.17 (dd, 9-H), 4.32 (d, 1'-H), 4.43 (dq, 5"-H), 4.59 (d, 4"-H), 5.01 (d, 1"-H), 5.06 (ddq, 15-H), 5.37 (br d, 3-H), 5.67 (dd, 10-H), 5.78 (ddd, 13-H), 6.09 (br dd, 12-H), 6.67 (dd, 11-H), 7.43 (br t, 3-OCOC$_6$H$_5$), 7.54 (tt, 3-OCOC$_6$H$_5$), 8.06 (br d, 3-OCOC$_6$H$_5$), 9.52 (br s, 18-H).

Example 26

Preparation of 2'-O-Acetyl-9-O-tert-butyldimethylsilyl-3-O-cyclohexylcarbonylleucomycin A$_7$ 18-Dimethylacetal (Compound Represented by Formula (VII) Wherein R$^1$ Represents Hydrogen Atom, R$^2$ Represents Propionyl Group and R$^6$ Represents Cyclohexylcarbonyl Group)

83.9 mg of the compound of Example 21 was added with 0.8 ml of dichloromethane and dissolved, further added with 360 μl of triethylamine, 166 μl of cyclohexanecarbonyl chloride and 26.2 mg of 4-dimethylaminopyridine, and then the mixture was reacted at room temperature for 3 days. The reaction mixture was added with 20 ml of saturated aqueous sodium hydrogencarbonate and extracted with 20 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (5:1→3:1)) to obtain 67.1 mg of a compound.

Physicochemical Properties of the Compound (1) Molecular formula: $C_{55}H_{95}NO_{17}Si$; (2) Mass spectrum (TSP): m/z 1070 (M+H)$^+$; (3) Specific rotation: $[\alpha]_D^{24}$ −57° (c 0.90, $CHCl_3$); (4) $^1H$ NMR spectrum (300 MHz, $CDCl_3$) δ (ppm): 0.92 (d, 19-H), 0.98 (br t, 7-H), 1.10 (s, 3"-CH$_3$), 1.12 (d, 6"-H), 1.16 (t, 4"-OCOCH$_2$CH$_3$), 1.23 (d, 16-H), 1.24 (d, 6'-H), 1.44 (dq, 3-OCOC$_6$H$_{11}$), 1.64 (m, 3-OCOC$_6$H$_{11}$), 1.74 (m, 3-OCOC$_6$H$_{11}$), 1.83 (dd, 2"-Hax), 1.92 (br d, 3-OCOC$_6$H$_{11}$), 2.00 (d, 2"-Heq), 2.00 (s, 2'-OCOCH$_3$), 2.10 (dt, 14-H), 2.22 (br d, 2-H), 2.31 (tt, 3-OCOC$_6$H$_{11}$), 2.39 (s, 3'-N(CH$_3$)$_2$), 2.42 (q, 4"-OCOCH$_2$CH$_3$), 2.43 (q, 4"-OCOCH$_2$CH$_3$), 2.68 (dd, 2-H), 2.70 (t, 3'-H), 3.13 (br d, 4-H), 3.22 (s, 18-OCH$_3$), 3.27 (s, 18-OCH$_3$), 3.44 (s, 4-OCH$_3$), 3.72 (br d, 5-H), 4.24 (dd, 9-H), 4.17 (dd, 18-H), 4.38 (dq, 5"-H), 4.61 (d, 4"-H), 4.73 (d, 1'-H), 4.92 (ddq, 15-H), 4.98 (dd, 2'-H), 5.02 (br d, 3-H), 5.06 (d, 1"-H), 5.56 (dd, 10-H), 5.67 (ddd, 13-H), 6.01 (br dd, 12-H), 6.31 (dd, 11-H).

Example 27

Preparation of 3-O-Cyclohexylcarbonylleucomycin A$_7$ (Compound Represented by Formula (I) Wherein R$^1$ Represents Hydrogen Atom, R$^2$ Represents Propionyl Group and R$^\alpha$ Represents Cyclohexylcarbonyl Group)

73.0 mg of the compound of Example 26 was added with 3.0 ml of methanol:water (9:1) and reacted overnight at 50° C. The reaction mixture was concentrated under reduced pressure, and the resulting residue was purified by silica gel column chromatography (hexane:ethyl acetate (1:1)) to obtain 60.1 mg of a compound. 58.1 mg of this compound was added with 9 ml of acetonitrile and dissolved, further added with 9 ml of water and 18.5 µl of difluoroacetic acid and stirred at room temperature for 3 days. The reaction mixture was added with 20 ml of saturated aqueous sodium hydrogencarbonate and extracted with 60 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (100:10:1)) to obtain 31.2 mg of a compound.

Physicochemical Properties of the Compound (1) Molecular formula: C$_{45}$H$_{73}$NO$_{15}$; (2) Mass spectrum (TSP): m/z 868 (M+H)$^+$; (3) Specific rotation: $[\alpha]_D^{21}$ −34° (c 1.2, CHCl$_3$); (4) $^1$H NMR spectrum (300 MHz, CDCl$_3$) δ (ppm): 0.95 (br t, 7-H), 0.98 (d, 19-H), 1.10 (s, 7"-H), 1.11 (d, 6"-H), 1.16 (t, 4"-OCOCH$_2$CH$_3$), 1.20 (d, 6'-H), 1.24 (d, 16-H), 1.45 (br dq, 3-OCOC$_6$H$_{11}$), 1.45 (m, 7-H), 1.63 (m, 3-OCOC$_6$H$_{11}$), 1.74 (m, 3-OCOC$_6$H$_{11}$), 1.82 (dd, 2"-Hax), 1.90 (m, 8-H), 1.99 (d, 2"-Heq), 2.03 (m, 3-OCOC$_6$H$_{11}$), 2.12 (dt, 14-H), 2.24 (br d, 2-H), 2.33 (br dd, 17-H), 2.42 (q, 4"-OCOCH$_2$CH$_3$), 2.43 (q, 4"-OCOCH$_2$CH$_3$), 2.49 (s, 3'-N(CH$_3$)$_2$), 2.74 (dd, 2-H), 2.76 (br dd, 17-H), 3.22 (dd, 4-H), 3.25 (t, 4'-H), 3.51 (dd, 2'-H), 3.51 (s, 4-OCH$_3$), 3.79 (br d, 5-H), 4.09 (dd, 9-H), 4.38 (d, 1'-H), 4.44 (dq, 5"-H), 4.60 (d, 4"-H), 5.01 (ddq, 15-H), 5.05 (d, 1"-H), 5.10 (br d, 3-H), 5.61 (dd, 10-H), 5.74 (ddd, 13-H), 6.05 (br dd, 12-H), 6.59 (dd, 11-H), 9.64 (br s, 18-H).

Example 28

Preparation of 2'-O-Acetyl-9-O-tert-butyldimethylsilyl-3-O-(6-phenylhexanoyl)leucomycin A$_7$ 18-Dimethylacetal (Compound Represented by Formula (VII) Wherein R$^1$ Represents Hydrogen Atom, R$^2$ Represents Propionyl Group and R$^6$ Represents 6-Phenylhexanoyl Group)

102 mg of the compound of Example 21 was added with 1.5 ml of dichloromethane and dissolved, further added with 205 µl of pyridine, 143 µl of 6-phenylhexanoyl chloride and 14.0 mg of 4-dimethylaminopyridine, and then the mixture was reacted overnight at room temperature. The reaction mixture was added with 20 ml of saturated aqueous sodium hydrogencarbonate and extracted with 80 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (5:1→3:1→1:1)) to obtain 76.6 mg of a compound.

Physicochemical Properties of the Compound (1) Molecular formula: C$_{60}$H$_{99}$NO$_{17}$Si; (2) Mass spectrum (TSP): m/z 1134 (M+H)$^+$; (3) Specific rotation: $[\alpha]_D^{23}$ −54° (c 0.79, CHCl$_3$); (4) $^1$H NMR spectrum (300 MHz, CDCl$_3$) δ (ppm): 0.93 (d, 19-H), 1.11 (s, 3"-CH$_3$), 1.12 (d, 6"-H), 1.16 (t, 4"-OCOCH$_2$CH$_3$), 1.23 (d, 16-H), 1.24 (d, 6'-H), 1.39 (m, 3-OCO(CH$_2$)$_5$C$_6$H$_5$), 1.64 (m, 3-OCO(CH$_2$)$_5$C$_6$H$_5$), 1.64 (quint, 3-OCO(CH$_2$)$_5$C$_6$H$_5$), 1.83 (m, 8-H), 1.83 (dd, 2"-Hax), 1.99 (d, 2"-Heq), 2.00 (s, 2'-OCOCH$_3$), 2.10 (dt, 14-H), 2.33 (br d, 2-H), 2.35 (t, 3-OCO(CH$_2$)$_5$C$_6$H$_5$), 2.39 (s, 3'-N(CH$_3$)$_2$), 2.42 (q, 4"-OCOCH$_2$CH$_3$), 2.43 (q, 4"-OCOCH$_2$CH$_3$), 2.61 (t, 3-OCO(CH$_2$)$_5$C$_6$H$_5$), 2.65 (dd, 2-H), 2.69 (t, 3'-H), 3.14 (dd, 4-H), 3.18 (s, 18-OCH$_3$), 3.20 (s, 18-OCH$_3$), 3.46 (s, 4-OCH$_3$), 3.78 (br d, 5-H), 4.16 (dd, 9-H), 4.38 (dq, 5"-H), 4.47 (dd, 18-H), 4.61 (d, 4"-H), 4.73 (d, 1'-H), 4.92 (ddq, 15-H), 4.98 (dd, 2'-H), 5.04 (br d, 3-H), 5.06 (d, 1"-H), 5.55 (dd, 10-H), 5.69 (ddd, 13-H), 6.01 (br dd, 12-H), 6.36 (dd, 11-H), 7.15 (m, 3-OCO(CH$_2$)$_5$C$_6$H$_5$), 7.25 (m, 3-OCO(CH$_2$)$_5$C$_6$H$_5$).

Example 29

Preparation of 3-O-(6-Phenylhexanoyl)leucomycin A$_7$ (Compound Represented by Formula (I) Wherein R$^1$ Represents Hydrogen Atom, R$^2$ Represents Propionyl Group and R$^\alpha$ Represents 6-Phenylhexanoyl Group)

72.9 mg of the compound of Example 28 was added with 4.5 ml of methanol:water (9:1) and reacted at 50° C. for 2 days. The reaction mixture was concentrated under reduced pressure, and the resulting residue was purified by silica gel column chromatography (chloroform:methanol (100:1)) to obtain 63.8 mg of a compound. 60.1 mg of this compound was added with 9 ml of acetonitrile and dissolved, further added with 9 ml of water and 18.0 µl of difluoroacetic acid, and then the mixture was stirred overnight at room temperature. The reaction mixture was added with 20 ml of saturated aqueous sodium hydrogencarbonate and extracted with 60 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (100:10:1)) to obtain 20.9 mg of a compound.

Physicochemical Properties of the Compound (1) Molecular formula: C$_{50}$H$_{77}$NO$_{15}$; (2) Mass spectrum (TSP): m/z 932 (M+H)$^+$; (3) Specific rotation: $[\alpha]_D^{24}$ −36° (c 0.81, CHCl$_3$); (4) $^1$H NMR spectrum (300 MHz, CDCl$_3$) δ (ppm): 0.91 (br ddd, 7-H), 0.98 (d, 19-H), 1.11 (s, 3"-CH$_3$), 1.12 (d, 6"-H), 1.17 (t, 4"-OCOCH$_2$CH$_3$), 1.17 (d, 6'-H), 1.24 (d, 16-H), 1.42 (quint, 3-OCO(CH$_2$)$_5$C$_6$H$_5$), 1.66 (quint, 3-OCO(CH$_2$)$_5$C$_6$H$_5$), 1.71 (quint, 3-OCO(CH$_2$)$_5$C$_6$H$_5$), 1.82 (dd, 2"-Hax), 1.88 (m, 8-H), 1.99 (d, 2"-Heq), 2.12 (dt, 14-H), 2.24 (br d, 2-H), 2.33 (br dd, 17-H), 2.42 (q, 4"-OCOCH$_2$CH$_3$), 2.43 (q, 4"-OCOCH$_2$CH$_3$), 2.50 (s, 3'-N(CH$_3$)$_2$), 2.61 (t, 3-OCO(CH$_2$)$_5$C$_6$H$_5$), 2.72 (dd, 2-H), 2.79 (dd, 17-H), 3.22 (dd, 4-H), 3.25 (t, 4'-H), 3.51 (dd, 2'-H), 3.51 (s, 4-OCH$_3$), 3.84 (br d, 5-H), 4.07 (br dd, 9-H), 4.39 (d, 1'-H), 4.43 (dq, 5"-H), 4.61 (d, 4"-H), 4.99 (ddq, 15-H), 5.05 (d, 1"-H), 5.11 (br d, 3-H), 5.60 (dd, 10-H), 5.74 (ddd, 13-H), 6.05 (br dd, 12-H), 6.62 (dd, 11-H), 7.16 (m, 3-OCO(CH$_2$)$_5$C$_6$H$_5$), 7.25 (m, 3-OCO(CH$_2$)$_5$C$_6$H$_5$), 9.61 (br s, 18-H).

Example 30

Preparation of 2'-O-Acetyl-9-O-tertbutyldimethylsilyl-3-O-(quinolin-2-yl)carbonylleucomycin A$_7$ 18-Dimethylacetal (Compound Represented by Formula (VII) Wherein R$^1$ Represents Hydrogen Atom, R$^2$ Represents Propionyl Group and R$^6$ Represents Quinolin-2-ylcarbonyl Group)

107 mg of the compound of Example 21 was added with 1.5 ml of dichloromethane and dissolved, further added with 518 µl of triethylamine, 265 mg of quinolin-2-ylcarbonyl chloride and 49.3 mg of 4-dimethylaminopyridine, and then the mixture was reacted at room temperature for 2 days. The reaction mixture was added with 30 ml of saturated aqueous sodium hydrogencarbonate and extracted with 50 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (3:1→2:1→1:1)) to obtain 102 mg of a compound.

Physicochemical Properties of the Compound (1) Molecular formula: $C_{58}H_{90}N_2O_{17}Si$; (2) Mass spectrum (TSP): m/z 1115 (M+H)$^+$; (3) Specific rotation: $[\alpha]_D^{21}$ −50° (c 0.64, CHCl$_3$); (4) $^1$H NMR spectrum (300 MHz, CDCl$_3$) δ (ppm): 0.95 (d, 19-H), 0.95 (d, 6'-H), 1.08 (d, 6"-H), 1.10 (s, 3"-CH$_3$), 1.16 (t, 4"-OCOCH$_2$CH$_3$), 1.23 (d, 16-H), 1.40 (ddd, 7-H), 1.47 (d, 17-H), 1.65 (m, 17-H), 1.74 (dd, 2"-Hax), 1.82 (br d, 2"-Heq), 2.04 (s, 2'-OCOCH$_3$), 2.13 (dt, 14-H), 2.38 (s, 3'-N(CH$_3$)$_2$), 2.42 (q, 4"-OCOCH$_2$CH$_3$), 2.43 (q, 4"-OCOCH$_2$CH$_3$), 2.68 (t, 3'-H), 2.92 (s, 18-OCH$_3$), 3.04 (s, 18-OCH$_3$), 3.28 (br d, 4'-H), 3.53 (s, 4-OCH$_3$), 3.78 (br d, 5-H), 4.22 (dd, 9-H), 4.23 (dd, 18-H), 4.35 (dq, 5"-H), 4.57 (d, 4"-H), 4.80 (d, 1'-H), 4.90 (d, 1"-H), 4.97 (dd, 2'-H), 5.04 (ddq, 15-H), 5.37 (br d, 3-H), 5.63 (dd, 10-H), 5.83 (ddd, 13-H), 6.08 (br dd, 12-H), 6.46 (dd, 11-H), 7.63 (ddd, 3-OCO-quinoline), 7.78 (ddd, 3-OCO-quinoline), 7.87 (dr d, 3-OCO-quinoline), 8.20 (d, 3-OCO-quinoline), 8.28 (d, 3-OCO-quinoline), 8.31 (dr d, 3-OCO-quinoline).

Example 31

Preparation of 3-O-(Quinolin-2-yl)carbonylleucomycin A$_7$ (Compound Represented by Formula (I) Wherein R$^1$ Represents Hydrogen Atom, R$^2$ Represents Propionyl Group and R$^\alpha$ Represents Quinolin-2-ylcarbonyl Group)

102 mg of the compound of Example 30 was added with 3.0 ml of methanol:water (9:1) and reacted at 45° C. for 2 days. The reaction mixture was concentrated under reduced pressure, and the resulting residue was purified by silica gel column chromatography (hexane:ethyl acetate (1:1)→ethyl acetate) to obtain 78.8 mg of a compound. 74.7 mg of this compound was added with 11 ml of acetonitrile and dissolved, further added with 11 ml of water and 26.5 µl of difluoroacetic acid, and then the mixture was stirred at room temperature for 3 days. The reaction mixture was added with 30 ml of saturated aqueous sodium hydrogencarbonate and extracted with 80 ml of chloroform. The organic layer was washed with 30 ml of saturated brine, dried over anhydrous sodium sulfate and filtered. The filtrate was concentrated under reduced pressure, and the resulting residue was purified by preparative TLC (chloroform:methanol:aqueous ammonia (100:10:1)) to obtain 31.3 mg of a compound.

Physicochemical Properties of the Compound (1) Molecular formula: $C_{48}H_{68}N_2O_{15}$; (2) Mass spectrum (TSP): m/z 913 (M+H)$^+$; (3) Specific rotation: $[\alpha]_D^{23}$ +4.2° (c 0.34, CHCl$_3$); (4) $^1$H NMR spectrum (300 MHz, CDCl$_3$) δ (ppm): 1.01 (d, 19-H), 1.01 (d, 6'-H), 1.09 (s, 3"-H), 1.09 (d, 6"-H), 1.16 (t, 4"-OCOCH$_2$CH$_3$), 1.22 (d, 16-H), 1.46 (br ddd, 7-H), 1.78 (dd, 2"-Hax), 1.90 (m, 8-H), 1.91 (d, 2"-Heq), 2.14 (dt, 14-H), 2.32 (br d, 17-H), 2.41 (br d, 2-H), 2.41 (q, 4"-OCOCH$_2$CH$_3$), 2.43 (q, 4"-OCOCH$_2$CH$_3$), 2.49 (s, 3'-N(CH$_3$)$_2$), 2.75 (dd, 17-H), 3.02 (dd, 2-H), 3.22 (t, 4'-H), 3.39 (br d, 4-H), 3.51 (dd, 2'-H), 3.61 (s, 4-OCH$_3$), 3.79 (br d, 5-H), 4.17 (dd, 9-H), 4.41 (d, 1'-H), 4.42 (dq, 5"-H), 4.58 (d, 4"-H), 4.97 (d, 1"-H), 5.08 (ddq, 15-H), 5.49 (br d, 3-H), 5.68 (dd, 10-H), 5.86 (ddd, 13-H), 6.11 (br dd, 12-H), 6.78 (dd, 11-H), 7.61 (ddd, 3-OCO-quinoline), 7.75 (ddd, 3-OCO-quinoline), 7.86 (dr d, 3-OCO-quinoline), 8.24 (d, 3-OCO-quinoline), 8.26 (d, 3-OCO-quinoline), 8.34 (dr d, 3-OCO-quinoline), 9.64 (br s, 18-H).

Example 32

Preparation of 2'-O-Acetyl-9-O-tert-butyldimethylsilyl-3-deoxy-3-oxorokitamycin 18-Dimethylacetal (Compound Represented by Formula (IV) Wherein R$^1$ Represents Propionyl Group, R$^2$ Represents Normal Butyryl Group, R$^3$ Represents tert-Butyldimethylsilyl Group and R$^4$ and R$^5$ Both Represent Methyl Group)

386 µl of dimethyl sulfoxide and 525 µl of trifluoroacetic acid anhydride were stirred in 20 ml of dichloromethane at −78° C. for 30 minutes. The mixture was added with a solution of 1.00 mg of the compound of Example 1 in dichloromethane (10 ml), and the mixture was stirred for 1 hour and added with 1.35 ml of triethylamine, and then gradually warmed to room temperature. The reaction mixture was added with 50 ml of saturated aqueous sodium hydrogencarbonate and extracted with 150 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (5:1→3:1)) to obtain 758 mg of a compound. This compound consisted of an inseparable keto-enol equilibrated mixture.

Physicochemical Properties of the Compound (1) Molecular formula: $C_{52}H_{89}NO_{17}Si$; (2) Mass spectrum (FAB): m/z 1028 (M+H)$^+$; (3) Specific rotation: $[\alpha]_D^{22}$ −56° (c 0.63, CHCl$_3$); (4) $^1$H NMR spectrum (keto compound) (300 MHz, CDCl$_3$) δ (ppm): 0.67 (br t, 7-H), 0.91 (d, 19-H), 0.96 (t, 4"-OCOCH$_2$CH$_2$CH$_3$), 1.05 (d, 6"-H), 1.13 (t, 3"-OCOCH$_2$CH$_3$), 1.19 (d, 6'-H), 1.32 (d, 16-H), 1.40 (s, 3"-CH$_3$), 1.66 (dd, 2"-Hax), 1.68 (sex, 4"-OCOCH$_2$CH$_2$CH$_3$), 1.85 (m, 17-H), 2.04 (s, 2'-OCOCH$_3$), 2.27 (q, 3"-OCOCH$_2$CH$_3$), 2.29 (q, 3"-OCOCH$_2$CH$_3$), 2.36 (t, 4"-OCOCH$_2$CH$_2$CH$_3$), 2.40 (s, 3'-N(CH$_3$)$_2$), 2.57 (t, 3'-H), 3.08 (t, 4'-H), 3.17 (d, 2"-Heq), 3.17 (dq, 5'-H), 3.25 (s, 18-OCH$_3$), 3.28 (s, 4-OCH$_3$), 3.37 (s, 18-OCH$_3$), 3.99 (br d, 5-H), 4.18 (dd, 9-H), 4.45 (dd, 18-H), 4.47 (dq, 5"-H), 4.55 (d, 4"-H), 4.73 (d, 1'-H), 4.79 (d, 1"-H), 4.95 (dd, 2'-H), 5.28 (ddq, 15-H), 5.40 (ddd, 13-H), 5.55 (dd, 10-H), 5.88 (br dd, 12-H), 5.94 (dd, 11-H); $^1$H NMR spectrum (enol compound) (300 MHz, CDCl$_3$) δ (ppm): 0.96 (t, 4"-OCOCH$_2$CH$_2$CH$_3$), 0.98 (d, 19-H), 1.04 (d, 6"-H), 1.13 (t, 3"-OCOCH$_2$CH$_3$), 1.28 (d, 16-H), 1.40 (s, 3"-CH$_3$), 1.68 (sex, 4"-OCOCH$_2$CH$_2$CH$_3$), 2.06 (s, 2'-OCOCH$_3$), 2.27 (q, 3"-OCOCH$_2$CH$_3$), 2.29 (q, 3"-OCOCH$_2$CH$_3$), 2.36 (t, 4"-OCOCH$_2$CH$_2$CH$_3$), 2.36 (s, 3'-N(CH$_3$)$_2$), 2.54 (t, 3'-H), 3.27 (s, 18-OCH$_3$), 3.32 (s, 18-OCH$_3$), 3.48 (s, 4-OCH$_3$), 4.22 (d, 1'-H), 4.55 (d, 4"-H), 4.90 (dd, 2'-H), 4.92 (s, 2-H), 5.44 (ddd, 13-H), 5.61 (dd, 10-H), 6.04 (dd, 11-H).

Example 33

Preparation of 3-Epi-2'-O-acetyl-9-O-tert-butyldimethylsilylrokitamycin 18-Dimethylacetal (Compound Represented by Formula (XII) Wherein R$^1$ Represents Propionyl Group and R$^2$ Represents Normal Butyryl Group)

709 mg of the compound of Example 32 was added with 14 ml of 1,4-dioxane and dissolved, further added with 258 mg of sodium borohydride, and the mixture was reacted at room temperature for 2 days. The reaction mixture was added with 20 ml of water and extracted with 100 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (5:1→1:1)) to obtain 437 mg of a compound.

Physicochemical Properties of the Compound (1) Molecular formula: C$_{52}$H$_{91}$NO$_{17}$Si; (2) Mass spectrum (FAB): m/z 1030 (M+H)$^+$; (3) Specific rotation: $[\alpha]_D^{23}$ −90° (c 0.57, CHCl$_3$); (4) $^1$H NMR spectrum (300 MHz, CDCl$_3$) δ (ppm): 0.96 (d, 19-H), 0.97 (t, 4"-OCOCH$_2$CH$_2$CH$_3$), 1.05 (d, 6"-H), 1.14 (t, 3"-OCOCH$_2$CH$_3$), 1.20 (d, 6'-H), 1.30 (d, 16-H), 1.40 (s, 3"-CH$_3$), 1.48 (m, 17-H), 1.65 (dd, 2"-Hax), 1.68 (sex, 4"-OCOCH$_2$CH$_2$CH$_3$), 1.89 (m, 17-H), 2.03 (s, 2'-OCOCH$_3$), 2.15 (dt, 14-H), 2.28 (q, 3"-OCOCH$_2$CH$_3$), 2.30 (q, 3"-OCOCH$_2$CH$_3$), 2.37 (t, 4"-OCOCH$_2$CH$_2$CH$_3$), 2.40 (s, 3'-N(CH$_3$)$_2$), 2.48 (br dt, 14-H), 2.58 (t, 3'-H), 2.60 (dd, 2-H), 3.09 (t, 4'-H), 3.19 (d, 2"-Heq), 3.28 (s, 18-OCH$_3$), 3.32 (s, 18-OCH$_3$), 3.45 (s, 4-OCH$_3$), 3.62 (br d, 5-H), 3.77 (m, 3-H), 4.16 (dd, 9-H), 4.47 (dd, 18-H), 4.47 (dq, 5"-H), 4.55 (d, 4"-H), 4.59 (d, 1'-H), 4.79 (d, 1"-H), 4.94 (dd, 2'-H), 5.22 (ddq, 15-H), 5.53 (ddd, 13-H), 5.66 (dd, 10-H), 6.01 (br dd, 12-H), 6.06 (dd, 11-H).

Example 34

Preparation of 3-Epi-rokitamycin (Compound Represented by Formula (II) Wherein R$^1$ Represents Propionyl Group, R$^2$ Represents Normal Butyryl Group and R$^\beta$ Represents Hydrogen Atom)

74.7 mg of the compound of Example 33 was added with 3.0 ml of methanol:water (9:1) and reacted at 45° C. for 2 days. The reaction mixture was concentrated under reduced pressure, and the resulting residue was purified by silica gel column chromatography (chloroform:methanol (200:1)) to obtain 67.8 mg of a compound. 62.9 mg of the resulting compound was added with 10 ml of acetonitrile and dissolved, further added with 10 ml of water and 20.0 µl of difluoroacetic acid and stirred overnight at room temperature. The reaction mixture was added with 20 ml of saturated aqueous sodium hydrogencarbonate and extracted with 60 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol (10:1)) to obtain 40.3 mg of a compound.

Physicochemical Properties of the Compound (1) Molecular formula: C$_{42}$H$_{69}$NO$_{15}$; (2) Mass spectrum (TSP): m/z 828 (M+H)$^+$; (3) Specific rotation: $[\alpha]_D^{23}$ −78° (c 0.53, CHCl$_3$); (4) $^1$H NMR spectrum (300 MHz, CDCl$_3$) δ (ppm): 0.95 (t, 4"-OCOCH$_2$CH$_2$CH$_3$), 1.04 (d, 6"-H), 1.05 (d, 19-H), 1.09 (d, 6'-H), 1.10 (t, 3"-OCOCH$_2$CH$_3$), 1.28 (d, 16-H), 1.38 (s, 3"-CH$_3$), 1.64 (dd, 2"-Hax), 1.66 (sex, 4"-OCOCH$_2$CH$_2$CH$_3$), 2.18 (dt, 14-H), 2.25 (q, 3"-OCOCH$_2$CH$_3$), 2.28 (q, 3"-OCOCH$_2$CH$_3$), 2.35 (t, 4"-OCOCH$_2$CH$_2$CH$_3$), 2.48 (s, 3'-N(CH$_3$)$_2$), 2.59 (br d, 2-H), 3.04 (t, 4'-H), 3.17 (d, 2"-Heq), 3.41 (s, 4-OCH$_3$), 3.47 (dd, 2'-H), 3.83 (br t, 5-H), 3.92 (br t, 3-H), 4.16 (m, 9-H), 4.18 (d, 1'-H), 4.53 (m, 5"-H), 4.55 (d, 4"-H), 4.77 (d, 1"-H), 5.31 (ddq, 15-H), 5.62 (ddd, 13-H), 5.64 (dd, 10-H), 6.04 (br dd, 12-H), 6.16 (dd, 11-H), 9.68 (br s, 18-H).

Example 35

Preparation of 3-Epi-2'-O-acetyl-3-O-benzoyl-9-O-tertbutyldimethylsilylrokitamycin 18-Dimethylacetal (Compound Represented by Formula (XIII) Wherein R$^1$ Represents Propionyl Group, R$^2$ Represents Normal Butyryl Group and R$^8$ Represents Benzoyl Group)

96.7 mg of the compound of Example 33 was added with 0.7 ml of dichloromethane and dissolved, further added with 321 µl of pyridine, 238 µl of benzoyl chloride and 29.2 mg of 4-dimethylaminopyridine, and the mixture was reacted at room temperature for 4 days. The reaction mixture was added with 20 ml of saturated aqueous sodium hydrogencarbonate and extracted with 50 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (2:1→1:1)) to obtain 85.3 mg of a compound.

Physicochemical Properties of the Compound (1) Molecular formula: C$_{59}$H$_{95}$NO$_{18}$Si; (2) Mass spectrum (TSP): m/z 1134 (M+H)$^+$; (3) Specific rotation: $[\alpha]_D^{23}$ −135° (c 0.51, CHCl$_3$); (4) $^1$H NMR spectrum (300 MHz, CDCl$_3$) δ (ppm): 0.97 (t, 4"-OCOCH$_2$CH$_2$CH$_3$), 0.99 (d, 16-H), 1.03 (d, 19-H), 1.05 (d, 6"-H), 1.14 (t, 3"-OCOCH$_2$CH$_3$), 1.21 (d, 6'-H), 1.40 (s, 3"-CH$_3$), 1.54 (m, 17-H), 1.67 (dd, 2"-Hax), 1.68 (sex, 4"-OCOCH$_2$CH$_2$CH$_3$), 1.80 (m, 8-H), 1.83 (m, 17-H), 1.99 (s, 2'-OCOCH$_3$), 2.28 (q, 3"-OCOCH$_2$CH$_3$), 2.30 (q, 3"-OCOCH$_2$CH$_3$), 2.36 (t, 4"-OCOCH$_2$CH$_2$CH$_3$), 2.40 (s, 3'-N(CH$_3$)$_2$), 2.54 (t, 3'-H), 2.99 (dd, 2-H), 3.11 (t, 4'-H), 3.19 (d, 2"-Heq), 3.29 (s, 18-OCH$_3$), 3.35 (s, 18-OCH$_3$), 3.40 (s, 4-OCH$_3$), 3.52 (br d, 5-H), 3.62 (dd, 4-H), 4.24 (dd, 9-H), 4.47 (dq, 5"-H), 4.56 (dd, 18-H), 4.56 (d, 4"-H), 4.67 (d, 1'-H), 4.80 (d, 1"-H), 4.93 (dd, 2'-H), 5.04 (ddq, 15-H), 5.07 (br d, 3-H), 5.39 (ddd, 13-H), 5.92 (br dd, 12-H), 5.98 (dd, 10-H), 6.09 (dd, 11-H), 7.47 (br t, 3-OCOC$_6$H$_5$), 7.59 (tt, 3-OCOC$_6$H$_5$), 8.12 (dt, 3-OCOC$_6$H$_5$).

Example 36

Preparation of 3-Epi-3-O-benzoylrokitamycin (Compound Represented by Formula (II) Wherein R$^1$ Represents Propionyl Group, R$^2$ Represents Normal Butyryl Group and R$^\beta$ Represents Benzoyl Group)

81.2 mg of the compound of Example 35 was added with 5.0 ml of methanol:water (9:1) and reacted overnight at 45° C. The reaction mixture was concentrated under reduced pressure, and the resulting residue was purified by silica gel column chromatography (hexane:ethyl acetate (2:1)) to obtain 73.0 mg of a compound. 68.9 mg of this compound was added with 10 ml of acetonitrile and dissolved, further added with 10 ml of water and 20.0 μl of difluoroacetic acid, and the mixture was stirred at room temperature for 2 days. The reaction mixture was added with 20 ml of saturated aqueous sodium hydrogencarbonate and extracted with 60 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (150:10:1)) to obtain 40.7 mg of a compound.

Physicochemical Properties of the Compound (1) Molecular formula: $C_{49}H_{73}NO_{16}$; (2) Mass spectrum (TSP): m/z 932 (M+H)$^+$; (3) Specific rotation: $[\alpha]_D^{23}$ −111° (c 0.52, CHCl$_3$); (4) $^1$H NMR spectrum (300 MHz, CDCl$_3$) δ (ppm): 0.96 (t, 4"-OCOCH$_2$CH$_2$CH$_3$), 0.98 (d, 16-H), 1.06 (d, 6"-H), 1.10 (d, 19-H), 1.11 (t, 3"-OCOCH$_2$CH$_3$), 1.15 (d, 6'-H), 1.34 (br t, 7-H), 1.40 (s, 3"-CH$_3$), 1.68 (dd, 2"-Hax), 1.68 (sex, 4"-OCOCH$_2$CH$_2$CH$_3$), 1.82 (m, 8-H), 1.86 (dt, 14-H), 2.26 (q, 3"-OCOCH$_2$CH$_3$), 2.28 (q, 3"-OCOCH$_2$CH$_3$), 2.36 (t, 4"-OCOCH$_2$CH$_2$CH$_3$), 2.49 (s, 3'-N(CH$_3$)$_2$), 2.62 (br d, 2-H), 3.04 (dd, 2-H), 3.04 (dd, 17-H), 3.14 (t, 4'-H), 3.20 (d, 2"-Heq), 3.38 (dd, 2'-H), 3.43 (s, 4-OCH$_3$), 3.53 (br d, 5-H), 3.81 (br d, 4-H), 4.13 (m, 9-H), 4.27 (d, 1'-H), 4.50 (dq, 5"-H), 4.56 (d, 4"-H), 4.82 (d, 1"-H), 4.98 (ddq, 15-H), 5.18 (br d, 3-H), 5.45 (ddd, 13-H), 5.83 (dd, 10-H), 5.97 (br dd, 12-H), 6.27 (dd, 11-H), 7.46 (br t, 3-OCOC$_6$H$_5$), 7.59 (br t, 3-OCOC$_6$H$_5$), 8.10 (br d, 3-OCOC$_6$H$_5$), 9.74 (br s, 18-H).

Example 37

Preparation of 3-Epi-2'-O-acetyl-9-O-tert-butyldimethylsilyl-3-O-imidazol-1-yl) carbonylrokitamycin 18-Dimethylacetal (Compound Represented by Formula (XIII) Wherein $R^1$ Represents Propionyl Group, $R^2$ Represents Normal Butyryl Group and $R^8$ Represents Imidazol-1-ylcarbonyl Group)

324 mg of the compound of Example 33 was added with 6.5 ml of THF and dissolved, further added with 313 mg of 1,1-carbonyldiimidazole, and then the mixture was reacted at room temperature for 2 days. The reaction mixture was diluted with 50 ml of chloroform. The organic layer was washed successively with 5% KHSO$_4$ aqueous solution, saturated aqueous sodium hydrogencarbonate and saturated brine, dried over anhydrous sodium sulfate and filtered. The filtrate was concentrated under reduced pressure, and the resulting residue was purified by silica gel column chromatography (hexane:ethyl acetate (3:1→1:1)) to obtain 299 mg of a compound.

Physicochemical Properties of the Compound (1) Molecular formula: $C_{56}H_{93}N_3O_{18}Si$; (2) Mass spectrum (FAB): m/z 1124 (M+H)$^+$; (3) Specific rotation: $[\alpha]_D^{24}$ −124° (c 0.58, CHCl$_3$); (4) $^1$H NMR spectrum (300 MHz, CDCl$_3$) δ (ppm): 0.97 (t, 4"-OCOCH$_2$CH$_2$CH$_3$), 1.00 (d, 19-H), 1.01 (d, 16-H), 1.06 (d, 6"-H), 1.15 (t, 3"-OCOCH$_2$CH$_3$), 1.22 (d, 6'-H), 1.40 (s, 3"-CH$_3$), 1.54 (br dd, 17-H), 1.68 (dd, 2"-Hax), 1.68 (sex, 4"-OCOCH$_2$CH$_2$CH$_3$), 2.01 (s, 2'-OCOCH$_3$), 2.27 (q, 3"-OCOCH$_2$CH$_3$), 2.30 (q, 3"-OCOCH$_2$CH$_3$), 2.36 (t, 4"-OCOCH$_2$CH$_2$CH$_3$), 2.40 (s, 3'-N(CH$_3$)$_2$), 2.55 (t, 3'-H), 2.98 (dd, 2-H), 3.11 (t, 4'-H), 3.19 (d, 2"-Heq), 3.29 (s, 18-OCH$_3$), 3.33 (s, 18-OCH$_3$), 3.43 (s, 4-OCH$_3$), 3.51 (br d, 5-H), 3.60 (br dd, 4-H), 4.22 (dd, 9-H), 4.47 (dq, 5"-H), 4.55 (m, 18-H), 4.56 (d, 4"-H), 4.66 (d, 1'-H), 4.80 (d, 1"-H), 4.93 (dd, 2'-H), 5.05 (br d, 3-H), 5.09 (ddq, 15-H), 5.41 (ddd, 13-H), 5.87 (dd, 10-H), 5.93 (br dd, 12-H), 6.10 (dd, 11-H), 7.12 (dd, 3-OCO-imidazole), 7.50 (dd, 3-OCO-imidazole), 8.19 (br s, 3-OCO-imidazole).

Example 38

Preparation of 3-Epi-2'-O-acetyl-9-O-tertbutyldimethylsilyl-3-O-(N-methylamino) carbonylrokitamycin 18-Dimethylacetal (Compound Represented by Formula (XIV) Wherein $R^1$ Represents Propionyl Group, $R^2$ Represents Normal Butyryl Group and $R^9$ Represents N-Methylaminocarbonyl Group)

101 mg of the compound of Example 37 was added with 3.0 ml of 2 M methylamine solution in THF and reacted overnight at 40° C. The reaction mixture was concentrated under reduced pressure, and the resulting residue was purified by silica gel column chromatography (hexane:ethyl acetate (3:1)) to obtain 92.3 mg of a compound.

Physicochemical Properties of the Compound (1) Molecular formula: $C_{54}H_{94}N_2O_{18}Si$; (2) Mass spectrum (TSP): m/z 1087 (M+H)$^+$; (3) Specific rotation: $[\alpha]_D^{23}$ −121° (c 0.67, CHCl$_3$); (4) $^1$H NMR spectrum (300 MHz, CDCl$_3$) δ (ppm): 0.93 (d, 19-H), 0.97 (t, 4"-OCOCH$_2$CH$_2$CH$_3$), 1.05 (d, 6"-H), 1.15 (t, 3"-OCOCH$_2$CH$_3$), 1.21 (d, 6'-H), 1.24 (d, 16-H), 1.40 (s, 3"-CH$_3$), 1.56 (m, 17-H), 1.67 (dd, 2"-Hax), 1.68 (sex, 4"-OCOCH$_2$CH$_2$CH$_3$), 1.83 (m, 17-H), 2.02 (s, 2'-OCOCH$_3$), 2.28 (q, 3"-OCOCH$_2$CH$_3$), 2.31 (q, 3"-OCOCH$_2$CH$_3$), 2.37 (t, 4"-OCOCH$_2$CH$_2$CH$_3$), 2.40 (s, 3'-N(CH$_3$)$_2$), 2.56 (t, 3'-H), 2.77 (m, 2-H), 2.80 (d, 3-OCOHNCH$_3$), 3.11 (t, 4'-H), 3.18 (d, 2"-Heq), 3.27 (s, 18-OCH$_3$), 3.33 (s, 18-OCH$_3$), 3.33 (s, 4-OCH$_3$), 3.51 (br d, 5-H), 4.19 (dd, 9-H), 4.47 (dd, 18-H), 4.47 (dq, 5"-H), 4.49 (d, 1'-H), 4.55 (d, 4"-H), 4.70 (m, 3-H), 4.80 (d, 1"-H), 4.94 (m, 15-H), 4.97 (dd, 2'-H), 5.40 (ddd, 13-H), 5.79 (m, 10-H), 6.04 (dd, 11-H), 6.13 (br dd, 12-H).

Example 39

Preparation of 3-Epi-3-O-(N-methylamino) carbonylrokitamycin (Compound Represented by Formula (II) Wherein $R^1$ Represents Propionyl Group, $R^2$ Represents Normal Butyryl Group and $R^\beta$ Represents N-Methylaminocarbonyl Group)

91.1 mg of the compound of Example 38 was added with 3.0 ml of methanol:water (9:1) and reacted overnight at 45° C. The reaction mixture was concentrated under reduced pressure, and the resulting residue was purified by silica gel column chromatography (hexane:ethyl acetate (1:1)) to obtain 86.0 mg of a compound. 70.9 mg of this compound was added with 11 ml of acetonitrile and dissolved, further added with 11 ml of water and 22.0 μl of difluoroacetic acid, and the mixture was stirred overnight at room temperature. The reaction mixture was added with 20 ml of saturated aqueous sodium hydrogencarbonate and extracted with 80 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (300:30:1)) to obtain 47.9 mg of a compound.

Physicochemical Properties of the Compound (1) Molecular formula: $C_{44}H_{72}N_2O_{16}$; (2) Mass spectrum (TSP): m/z 885 (M+H)$^+$; (3) Specific rotation: $[\alpha]_D^{25}$ −91° (c 0.51, CHCl$_3$); (4) $^1$H NMR spectrum (300 MHz, CDCl$_3$) δ (ppm): 0.95 (t, 4"-OCOCH$_2$CH$_2$CH$_3$), 1.06 (d, 19-H), 1.06

(d, 6"-H), 1.10 (t, 3"-OCOCH$_2$CH$_3$), 1.14 (d, 6'-H), 1.24 (d, 16-H), 1.39 (s, 3"-CH$_3$), 1.66 (dd, 2"-Hax), 1.66 (m, 8-H), 1.66 (m, 7-H), 1.67 (sex, 4"-OCOCH$_2$CH$_2$CH$_3$), 2.12 (dt, 14-H), 2.25 (q, 3"-OCOCH$_2$CH$_3$), 2.27 (q, 3"-OCOCH$_2$CH$_3$), 2.35 (t, 4"-OCOCH$_2$CH$_2$CH$_3$), 2.49 (s, 3'-N(CH$_3$)$_2$), 2.74 (dd, 2-H), 2.82 (d, 3-OCOHNCH$_3$), 2.99 (dd, 17-H), 3.08 (t, 4'-H), 3.18 (d, 2"-Heq), 3.45 (s, 4-OCH$_3$), 3.62 (m, 4-H), 4.13 (br s, 9-H), 4.22 (d, 1'-H), 4.51 (dq, 5"-H), 4.55 (d, 4"-H), 4.79 (d, 1"-H), 4.90 (br d, 3-H), 5.02 (ddq, 15-H), 5.56 (ddd, 13-H), 5.68 (dd, 10-H), 6.03 (br dd, 12-H), 6.28 (dd, 11-H), 9.74 (br s, 18-H).

Example 40

Preparation of 3-Epi-2'-O-Acetyl-3-O-(N-benzylamino)carbonyl-9-O-tert-butyldimethylsilylrokitamycin 18-Dimethylacetal (Compound Represented by Formula (XIV) Wherein R$^1$ Represents Propionyl Group, R$^2$ Represents Normal Butyryl Group and R$^9$ Represents N-Benzylaminocarbonyl Group)

101 mg of the compound of Example 37 was added with 2.0 ml of THF and dissolved, further added with 440 µl of benzylamine, and then the mixture was reacted at 45° C. for 3 days. The reaction mixture was diluted with 50 ml of chloroform. The organic layer was washed successively with 5% KHSO$_4$ aqueous solution, saturated aqueous sodium hydrogencarbonate and saturated brine, and then dried over anhydrous sodium sulfate and filtered. The resulting residue was purified by silica gel column chromatography (hexane:ethyl acetate (10:1→5:1→3:1)) to obtain 73.6 mg of a compound.

Physicochemical Properties of the Compound (1) Molecular formula: C$_{60}$H$_{98}$N$_2$O$_{18}$Si; (2) Mass spectrum (TSP): m/z 1163 (M+H)$^+$; (3) Specific rotation: [α]$_D^{23}$ −112° (c 0.54, CHCl$_3$); (4) $^1$H NMR spectrum (300 MHz, CDCl$_3$) δ (ppm): 0.95 (d, 19-H), 0.97 (t, 4"-OCOCH$_2$CH$_2$CH$_3$), 1.05 (d, 6"-H), 1.15 (t, 3"-OCOCH$_2$CH$_3$), 1.16 (d, 16-H), 1.20 (d, 6'-H), 1.40 (s, 3"-CH$_3$), 1.54 (m, 17-H), 1.67 (dd, 2"-Hax), 1.68 (sex, 4"-OCOCH$_2$CH$_2$CH$_3$), 1.83 (br t, 17-H), 2.01 (s, 2'-OCOCH$_3$), 2.15 (br d, 2-H), 2.28 (q, 3"-OCOCH$_2$CH$_3$), 2.31 (q, 3"-OCOCH$_2$CH$_3$), 2.37 (t, 4"-OCOCH$_2$CH$_2$CH$_3$), 2.40 (s, 3'-N(CH$_3$)$_2$), 2.56 (t, 3'-H), 2.77 (br dd, 2-H), 3.11 (t, 4'-H), 3.18 (d, 2"-Heq), 3.26 (s, 18-OCH$_3$), 3.32 (s, 18-OCH$_3$), 3.38 (s, 4-OCH$_3$), 3.49 (br d, 5-H), 4.20 (dd, 9-H), 4.24 (dd, CH$_2$C$_6$H$_5$), 4.48 (m, 18-H), 4.48 (d, 1'-H), 4.48 (dd, CH$_2$C$_6$H$_5$), 4.49 (dq, 5"-H), 4.55 (d, 4"-H), 4.71 (m, 3-H), 4.80 (d, 1"-H), 4.92 (m, 15-H), 4.96 (dd, 2'-H), 5.38 (ddd, 13-H), 5.86 (m, 10-H), 6.02 (br dd, 12-H), 6.06 (dd, 11-H).

Example 41

Preparation of 3-Epi-3-O-(N-benzylamino) carbonylrokitamycin (Compound Represented by Formula (II) Wherein R$^1$ Represents Propionyl Group, R$^2$ Represents Normal Butyryl Group and R$^β$ Represents N-Benzylaminocarbonyl Group)

68.1 mg of the compound of Example 40 was added with 4.0 ml of methanol:water (9:1) and reacted at 45° C. for 3 days. The reaction mixture was concentrated under reduced pressure, and the resulting residue was purified by silica gel column chromatography (hexane:ethyl acetate (2:1)) to obtain 62.7 mg of a compound. 57.0 mg of this compound was added with 8.0 ml of acetonitrile and dissolved, further added with 8.0 ml of water and 16.0 µl of difluoroacetic acid and stirred at room temperature for 2 days. The reaction mixture was added with 20 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (300:30:1)) to obtain 42.7 mg of a compound.

Physicochemical Properties of the Compound (1) Molecular formula: C$_{50}$H$_{76}$N$_2$O$_{16}$; (2) Mass spectrum (TSP): m/z 961 (M+H)$^+$; (3) Specific rotation: [α]$_D^{25}$ −77° (c 0.56, CHCl$_3$); (4) $^1$H NMR spectrum (300 MHz, CDCl$_3$) δ (ppm): 0.96 (t, 4"-OCOCH$_2$CH$_2$CH$_3$), 1.06 (d, 6"-H), 1.08 (d, 16-H), 1.10 (t, 3"-OCOCH$_2$CH$_3$), 1.12 (d, 19-H), 1.13 (d, 6'-H), 1.39 (s, 3"-CH$_3$), 1.67 (dd, 2"-Hax), 1.67 (sex, 4"-OCOCH$_2$CH$_2$CH$_3$), 2.01 (dt, 14-H), 2.25 (q, 3"-OCOCH$_2$CH$_3$), 2.27 (q, 3"-OCOCH$_2$CH$_3$), 2.36 (t, 4"-OCOCH$_2$CH$_2$CH$_3$), 2.49 (s, 3'-N(CH$_3$)$_2$), 2.74 (dd, 2-H), 3.00 (dd, 17-H), 3.12 (t, 4'-H), 3.18 (d, 2"-Heq), 3.42 (dd, 2'-H), 3.47 (s, 4-OCH$_3$), 3.71 (m, 4-H), 4.14 (m, 9-H), 4.22 (d, 1'-H), 4.25 (dd, CH$_2$C$_6$H$_5$), 4.43 (dd, CH$_2$C$_6$H$_5$), 4.49 (dq, 5"-H), 4.56 (d, 4"-H), 4.80 (d, 1"-H), 4.90 (br d, 3-H), 4.93 (ddq, 15-H), 5.36 (ddd, 13-H), 5.66 (dd, 10-H), 5.97 (br dd, 12-H), 6.22 (dd, 11-H), 7.35 (m, CH$_2$C$_6$H$_5$), 9.73 (br s, 18-H).

Example 42

Preparation of 2'-O-Acetyl-9-O-tert-butyldimethylsilyl-3-deoxy-3-oxoleucomycin A$_7$ 18-Dimethylacetal (Compound Represented by Formula (IV) Wherein R$^1$ Represents Hydrogen Atom, R$^2$ Represents Propionyl Group, R$^3$ Represents tert-Butyldimethylsilyl Group and R$^4$ and R$^5$ Both Represent Methyl Group)

630 µl of dimethyl sulfoxide and 840 µl of trifluoroacetic acid anhydride were stirred in 20 ml of dichloromethane at −78° C. for 20 minutes. The mixture was added with a solution of 1.51 mg of the compound of Example 21 in dichloromethane (8.0 ml), stirred for 45 minutes, and then added with 2.2 ml of triethylamine and gradually warmed up to room temperature. The reaction mixture was added with 50 ml of saturated aqueous sodium hydrogencarbonate and extracted with 150 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (20:1→15:1)) to obtain 448 mg of a compound product. The compound product consisted of an inseparable keto-enol equilibrated mixture.

Physicochemical Properties of the Compound (1) Molecular formula: C$_{48}$H$_{83}$NO$_{16}$Si; (2) Mass spectrum (TSP): m/z 958 (M+H)$^+$; (3) Specific rotation: [α]$_D^{24}$ −59° (c 1.0, MeOH); (4) $^1$H NMR spectrum (keto compound) (300 MHz, CDCl$_3$) δ (ppm): 0.68 (br t, 7-H), 0.92 (d, 19-H), 1.10 (s, 3"-CH$_3$), 1.11 (d, 6"-H), 1.16 (t, 4"-OCOCH$_2$CH$_3$), 1.27 (d, 6'-H), 1.32 (d, 16-H), 1.52 (m, 6-H), 1.59 (m, 7-H), 1.61 (m, 17-H), 1.83 (m, 8-H), 1.83 (dd, 2"-Hax), 1.84 (m, 17-H), 1.99 (d, 2"-Heq), 2.04 (s, 2'-OCOCH$_3$), 2.39 (s, 3'-N(CH$_3$)$_2$), 2.42 (q, 4"-OCOCH$_2$CH$_3$), 2.43 (q, 4"-OCOCH$_2$CH$_3$), 2.71 (t, 3'-H), 3.25 (s, 18-OCH$_3$), 3.27 (s, 4-OCH$_3$), 3.37 (s, 18-OCH$_3$), 4.01 (br d, 5-H), 4.18 (dd, 9-H), 4.38 (dq, 5"-H), 4.47 (dd, 18-H), 4.60 (d, 4"-H), 4.79 (d, 1'-H), 4.99 (dd, 2'-H), 5.07 (d, 1"-H), 5.28 (ddq, 15-H), 5.40 (ddd, 13-H), 5.65 (dd, 10-H), 5.89 (br dd, 12-H), 5.94 (dd, 11-H); $^1$H NMR spectrum (enol compound) (300 MHz, CDCl$_3$) δ (ppm): 0.98 (d, 19-H), 1.10 (s, 3"-CH$_3$), 1.10 (d, 6"-H), 1.16 (t, 4"-OCOCH$_2$CH$_3$), 1.27 (d, 6'-H), 1.83 (dd, 2"-Hax), 1.98 (d, 2"-Heq), 2.06 (s, 2'-OCOCH$_3$), 2.35 (s, 3'-N(CH$_3$)$_2$), 2.42 (q, 4"-OCOCH$_2$CH$_3$), 2.43 (q, 4"-OCOCH$_2$CH$_3$), 2.68 (t, 3'-H), 3.27 (s, 18-OCH$_3$), 3.32 (s, 18-OCH$_3$), 3.48 (s, 4-OCH$_3$), 3.62 (m, 4-H), 4.18 (dd, 9-H), 4.27 (br d, 1'-H), 4.60 (d, 4"-H), 4.79 (d, 1'-H), 4.92 (s, 2-H), 4.94 (dd, 2'-H), 5.04 (d, 1"-H), 5.61 (dd, 10-H), 6.04 (dd, 11-H).

Example 43

Preparation of 3-Epi-2'-O-acetyl-9-O-tert-butyldimethylsilylleucomycin A$_7$ 18-Dimethylacetal (Compound Represented by Formula (XII) Wherein R$^1$ Represents Hydrogen Atom and R$^2$ Represents Propionyl Group)

346 mg of the compound of Example 42 was added with 8.0 ml of 1,4-dioxane and dissolved, further added with 65.0 mg of sodium borohydride, and then the mixture was reacted overnight at room temperature. The reaction mixture was added with 20 ml of water and extracted with 80 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (2:1→1:1)) to obtain 259 mg of a compound.
Physicochemical Properties of the Compound
  (1) Molecular formula: C$_{48}$H$_{75}$NO$_{16}$Si; (2) Mass spectrum (FAB): m/z 960 (M+H)$^+$; (3) Specific rotation: [α]$_D^{23}$ −91° (c 1.0, MeOH); (4) $^1$H NMR spectrum (300 MHz, CDCl$_3$) δ (ppm): 0.95 (d, 19-H), 1.10 (s, 3"-CH$_3$), 1.11 (d, 6"-H), 1.16 (t, 4"-OCOCH$_2$CH$_3$), 1.27 (d, 6'-H), 1.30 (d, 16-H), 1.49 (m, 17-H), 1.62 (m, 8-H), 1.83 (dd, 2"-Hax), 1.98 (d, 2"-Heq), 2.03 (s, 2'-OCOCH$_3$), 2.15 (dt, 14-H), 2.27 (br d, 2-H), 2.39 (s, 3'-N(CH$_3$)$_2$), 2.42 (q, 4"-OCOCH$_2$CH$_3$), 2.43 (q, 4"-OCOCH$_2$CH$_3$), 2.50 (m, 14-H), 2.59 (dd, 2-H), 2.71 (t, 3'-H), 3.28 (s, 18-OCH$_3$), 3.32 (s, 18-OCH$_3$), 3.46 (s, 4-OCH$_3$), 3.60 (br d, 5-H), 3.77 (m, 3-H), 4.16 (dd, 9-H), 4.39 (dq, 5"-H), 4.49 (dd, 18-H), 4.60 (d, 4"-H), 4.66 (d, 1'-H), 4.98 (dd, 2'-H), 5.06 (d, 1"-H), 5.23 (ddq, 15-H), 5.53 (ddd, 13-H), 5.66 (dd, 10-H), 6.01 (br dd, 12-H), 6.06 (dd, 11-H).

Example 44

Preparation of 3-Epileucomycin A$_7$ (Compound Represented by Formula (II) Wherein R$^1$ Represents Hydrogen Atom, R$^2$ Represents Propionyl Group and R$^\beta$ Represents Hydrogen Atom)

73.4 mg of the compound of Example 43 was added with 10 ml of methanol:water (9:1) and reacted overnight at 50° C. The reaction mixture was concentrated under reduced pressure, and the resulting residue was purified by silica gel column chromatography (chloroform:methanol (20:1→10:1)) to obtain 68.7 mg of a compound. 68.7 mg of this compound was added with 13 ml of acetonitrile and dissolved, further added with 13 ml of water and 24.0 μl of difluoroacetic acid, and the mixture was stirred overnight at room temperature. The reaction mixture was added with 30 ml of saturated aqueous sodium hydrogencarbonate and extracted with 80 ml of chloroform. The organic layer was washed with 30 ml of saturated brine, dried over anhydrous sodium sulfate and filtered. The filtrate was concentrated under reduced pressure, and the resulting residue was purified by silica gel column chromatography (chloroform:methanol:aqueous ammonia (450:3:0.1→600:6:1)) to obtain 44.4 mg of a compound.
Physicochemical Properties of the Compound
  (1) Molecular formula: C$_{38}$H$_{63}$NO$_{14}$; (2) Mass spectrum (FAB): m/z 758 (M+H)$^+$; (3) Specific rotation: [α]$_D^{23}$ −57° (c 1.0, CHCl$_3$); (4) $^1$H NMR spectrum (300 MHz, CDCl$_3$) δ (ppm): 1.10 (s, 3"-CH$_3$), 1.10 (d, 6"-H), 1.11 (d, 19-H), 1.16 (t, 4"-OCOCH$_2$CH$_3$), 1.19 (d, 6'-H), 1.30 (d, 16-H), 1.37 (m, 7-H), 1.61 (m, 8-H), 1.81 (dd, 2"-Hax), 1.98 (d, 2"-Heq) 2.19 (dt, 14-H), 2.42 (q, 4"-OCOCH$_2$CH$_3$), 2.43 (q, 4"-OCOCH$_2$CH$_3$), 2.47 (s, 3'-N(CH$_3$)$_2$), 2.61 (d, 2-H), 3.14 (m, 4-H), 3.21 (t, 4'-H), 3.28 (dq, 5'-H), 3.42 (s, 4-OCH$_3$), 3.57 (dd, 2'-H), 3.86 (br t, 5-H), 3.92 (br t, 3-H), 4.18 (m, 9-H), 4.20 (d, 1'-H), 4.47 (dq, 5"-H), 4.60 (d, 4"-H), 5.04 (d, 1"-H), 5.34 (ddq, 15-H), 5.65 (dd, 10-H), 5.65 (ddd, 13-H), 6.05 (br dd, 12-H), 6.18 (dd, 11-H), 9.72 (br s, 18-H).

Example 45

Preparation of 3-Epi-2'-O-acetyl-9-O-tert-butyldimethylsilyl-3-O-propionylleucomycin A$_7$ 18-Dimethylacetal (Compound Represented by Formula (XIII) Wherein R$^1$ Represents Hydrogen Atom, R$^2$ Represents Propionyl Group and R$^8$ Represents Propionyl Group)

101 mg of the compound of Example 43 was added with 1.2 ml of dichloromethane and dissolved, further added with 130 μl of pyridine, 50.0 μl of propionyl chloride and 12.7 mg of 4-dimethylaminopyridine, and then the mixture was reacted at room temperature for 4 hours. The reaction mixture was added with 20 ml of saturated aqueous sodium hydrogencarbonate and extracted with 50 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (5:1→2:1→1:1)) to obtain 55.1 mg of a compound.
Physicochemical Properties of the Compound
  (1) Molecular formula: C$_{51}$H$_{89}$NO$_{17}$Si; (2) Mass spectrum (FAB): m/z 1016 (M+H)$^+$; (3) Specific rotation: [α]$_D^{23}$ −127° (c 1.0, MeOH); (4) $^1$H NMR spectrum (300 MHz, CDCl$_3$) δ (ppm): 0.99 (d, 19-H), 1.10 (s, 3"-CH$_3$), 1.11 (d, 6"-H), 1.16 (t, 4"-OCOCH$_2$CH$_3$), 1.22 (t, 3-OCOCH$_2$CH$_3$), 1.24 (d, 16-H), 1.28 (d, 6'-H), 1.55 (m, 17-H), 1.78 (m, 8-H), 1.84 (dd, 2"-Hax), 1.98 (dt, 14-H), 2.00 (d, 2"-Heq), 2.03 (s, 2'-OCOCH$_3$), 2.20 (br d, 2-H), 2.36 (q, 3-OCOCH$_2$CH$_3$), 2.39 (s, 3'-N(CH$_3$)$_2$), 2.42 (q, 4"-OCOCH$_2$CH$_3$), 2.43 (q, 4"-OCOCH$_2$CH$_3$), 2.69 (t, 3'-H), 2.81 (dd, 2-H), 3.28 (s, 18-OCH$_3$), 3.34 (s, 18-OCH$_3$), 3.40 (dd, 4-H), 3.41 (s, 4-OCH$_3$), 3.46 (br d, 5-H), 4.21 (dd, 9-H), 4.38 (dq, 5"-H), 4.52 (dd, 18-H), 4.61 (d, 4"-H), 4.68 (d, 1'-H), 4.87 (br d, 3-H), 4.96 (dd, 2'-H), 5.07 (d, 1"-H), 5.10 (ddq, 15-H), 5.41 (ddd, 13-H), 5.89 (dd, 10-H), 6.95 (br dd, 12-H), 6.06 (dd, 11-H).

Example 46

Preparation of 3-Epi-3-O-propionylleucomycin A$_7$ (Compound Represented by Formula (II) Wherein R$^1$ Represents Hydrogen Atom, R$^2$ Represents Propionyl Group and R$^\beta$ Represents Propionyl Group)

55.1 mg of the compound of Example 45 was added with 8.0 ml of methanol:water (9:1) and reacted overnight at 50°

C. The reaction mixture was concentrated under reduced pressure, and the resulting residue was purified by silica gel column chromatography (chloroform:methanol (50:1→20:1)) to obtain 53.3 mg of a compound. 43.0 mg of the resulting compound was added with 7.5 ml of acetonitrile and dissolved, further added with 7.5 ml of water and 14.0 µl of difluoroacetic acid, and then the mixture was stirred at room temperature for 3 days. The reaction mixture was added with 20 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (400:20:1)) to obtain 24.8 mg of a compound.

Physicochemical Properties of the Compound (1) Molecular formula: $C_{41}H_{67}NO_{15}$; (2) Mass spectrum (FAB): m/z 814 $(M+H)^+$; (3) Specific rotation: $[\alpha]_D^{24}$ −99° (c 0.38, $CHCl_3$); (4) $^1H$ NMR spectrum (300 MHz, $CDCl_3$) δ (ppm): 1.07 (d, 19-H), 1.10 (s, 3"-$CH_3$), 1.11 (d, 6"-H), 1.16 (t, 4"-$OCOCH_2CH_3$), 1.20 (t, 3-$OCOCH_2CH_3$), 1.22 (d, 6'-H), 1.25 (ddd, 7-H), 1.25 (d, 16-H), 1.54 (ddd, 7-H), 1.58 (m, 8-H), 1.82 (dd, 2"-Hax), 1.98 (d, 2"-Heq), 2.09 (dt, 14-H), 2.16 (m, 6-H), 2.35 (t, 3-$OCOCH_2CH_3$), 2.42 (q, 4"-$OCOCH_2CH_3$), 2.43 (q, 4"-$OCOCH_2CH_3$), 2.48 (s, 3'-N($CH_3$)$_2$), 2.84 (dd, 2-H), 2.99 (dd, 17-H), 3.44 (s, 4-$OCH_3$), 3.48 (dd, 2'-H), 3.53 (d, 5-H), 4.11 (m, 9-H), 4.28 (d, 1'-H), 4.46 (dq, 5"-H), 4.61 (d, 4"-H), 5.03 (br d, 3-H), 5.05 (d, 1"-H), 5.06 (ddq, 15-H), 5.54 (ddd, 13-H), 5.77 (dd, 10-H), 5.99 (br dd, 12-H), 6.24 (dd, 11-H), 9.74 (br s, 18-H).

Example 47

Preparation of 3-Epi-2'-O-Acetyl-3-O-benzoyl-9-O-tert-butyldimethylsilylleucomycin $A_7$ 18-Dimethylacetal (Compound Represented by Formula (XIII) Wherein $R^1$ Represents Hydrogen Atom, $R^2$ Represents Propionyl Group and $R^8$ Represents Benzoyl Group)

70.4 mg of the compound of Example 43 was added with 1.0 ml of dichloromethane and dissolved, further added with 140 µl of pyridine, 84.0 µl of benzoyl chloride and 21.0 mg of 4-dimethylaminopyridine, and then the mixture was reacted at room temperature for 4 days. The reaction mixture was added with 20 ml of saturated aqueous sodium hydrogencarbonate and extracted with 50 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (5:1→3:1→2:1→1:1)) to obtain 72.6 mg of a compound.

Physicochemical Properties of the Compound (1) Molecular formula: $C_{55}H_{89}NO_{17}Si$; (2) Mass spectrum (FAB): m/z 1064 $(M+H)^+$; (3) Specific rotation: $[\alpha]_D^{20}$ −128° (c 0.53, $CHCl_3$); (4) $^1H$ NMR spectrum (300 MHz, $CDCl_3$) δ (ppm): 0.98 (d, 16-H), 1.03 (d, 19-H), 1.10 (s, 3"-$CH_3$), 1.11 (d, 6"-H), 1.15 (t, 4"-$OCOCH_2CH_3$), 1.29 (d, 6'-H), 1.56 (m, 17-H), 1.69 (dt, 14-H), 1.83 (m, 8-H), 1.83 (m, 17-H), 1.83 (dd, 2"-Hax), 1.98 (d, 2"-Heq), 1.98 (s, 2'-$OCOCH_3$), 2.27 (br d, 2-H), 2.27 (br d, 14-H), 2.37 (s, 3'-N($CH_3$)$_2$), 2.41 (q, 4"-$OCOCH_2CH_3$), 2.42 (q, 4"-$OCOCH_2CH_3$), 2.68 (t, 3'-H), 3.00 (dd, 2-H), 3.29 (s, 18-$OCH_3$), 3.35 (s, 18-$OCH_3$), 3.39 (s, 4-$OCH_3$), 3.52 (br d, 5-H), 3.61 (dd, 4-H), 4.24 (dd, 9-H), 4.38 (dq, 5"-H), 4.57 (dd, 18-H), 4.60 (d, 4"-H), 4.73 (d, 1'-H), 4.97 (dd, 2'-H), 5.05 (ddq, 15-H), 5.06 (d, 1-H), 5.08 (br d, 3-H), 5.38 (ddd, 13-H), 5.91 (br dd, 12-H), 5.98 (dd, 10-H), 6.08 (dd, 11-H), 7.46 (br t, 3-$OCOC_6H_5$), 7.58 (tt, 3-$OCOC_6H_5$), 8.11 (dd, 3-$OCOC_6H_5$).

Example 48

Preparation of 3-Epi-3-O-benzoylleucomycin $A_7$ (Compound Represented by Formula (II) Wherein $R^1$ Represents Hydrogen Atom, $R^2$ Represents Propionyl Group and $R^\beta$ Represents Benzoyl Group)

67.4 mg of the compound of Example 47 was added with 3.0 ml of methanol:water (9:1) and reacted at 50° C. for 2 days. The reaction mixture was concentrated under reduced pressure, and the resulting residue was purified by silica gel column chromatography (hexane:ethyl acetate (2:1)) to obtain 60.7 mg of a compound. 57.0 mg of the resulting compound was added with 13 ml of acetonitrile and dissolved, further added with 8.0 ml of water and 18.0 µl of difluoroacetic acid, and then the mixture was stirred at room temperature for 4 days. The reaction mixture was added with 20 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (150:10:1)) to obtain 28.3 mg of a compound.

Physicochemical Properties of the Compound (1) Molecular formula: $C_{45}H_{67}NO_{15}$; (2) Mass spectrum (TSP): m/z 862 $(M+H)^+$; (3) Specific rotation: $[\alpha]_D^{26}$ −112° (c 1.3, $CHCl_3$); (4) $^1H$ NMR spectrum (300 MHz, $CDCl_3$) δ (ppm): 0.99 (d, 16-H), 1.10 (s, 3"-$CH_3$), 1.12 (d, 19-H), 1.12 (d, 6"-H), 1.16 (t, 4"-$OCOCH_2CH_3$), 1.22 (d, 6'-H), 1.31 (br t, 7-H), 1.69 (ddd, 7-H), 1.82 (dd, 2"-Hax), 1.86 (m, 8-H), 1.90 (dt, 14-H), 1.99 (d, 2"-Heq), 2.20 (m, 6-H), 2.43 (q, 4"-$OCOCH_2CH_3$), 2.44 (q, 4"-$OCOCH_2CH_3$), 2.47 (s, 3'-N($CH_3$)$_2$), 2.62 (dd, 2-H), 3.03 (dd, 2-H), 3.03 (dd, 17-H), 3.24 (m, 5'-H), 3.25 (m, 4'-H), 3.42 (s, 4-$OCH_3$), 3.52 (dd, 2'-H), 3.54 (br d, 4-H), 3.81 (br d, 5-H), 4.15 (m, 9-H), 4.30 (d, 1'-H), 4.46 (dq, 5"-H), 4.61 (d, 4"-H), 5.00 (ddq, 15-H), 5.06 (d, 1"-H), 5.21 (br d, 3-H), 5.46 (ddd, 13-H), 5.83 (dd, 10-H), 5.98 (br dd, 12-H), 6.29 (dd, 11-H), 7.47 (br t, 3-$OCOC_6H_5$), 7.60 (br t, 3-$OCOC_6H_5$), 8.10 (br d, 3-$OCOC_6H_5$), 9.76 (s, 18-H).

Example 49

Preparation of 3-Epi-2'-O-acetyl-9-O-tertbutyldimethylsilyl-3-O-(4-methoxybenzoyl) leucomycin $A_7$ 18-Dimethylacetal (Compound Represented by Formula (XIII) Wherein $R^1$ Represents Hydrogen Atom, $R^2$ Represents Propionyl Group and $R^8$ Represents 4-Methoxybenzoyl Group)

71.3 mg of the compound of Example 43 was added with 1.5 ml of dichloromethane and dissolved, further added with 204 µl of pyridine, 190 ml of 4-methoxybenzoyl chloride and 10.3 mg of 4-dimethylaminopyridine, and then the mixture was reacted at room temperature for 4 days. The reaction mixture was added with 20 ml of saturated aqueous sodium hydrogencarbonate and extracted with 50 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (3:1→2:1→1:1)) to obtain 50.3 mg of a compound.

Physicochemical Properties of the Compound (1) Molecular formula: $C_{56}H_{91}NO_{18}Si$; (2) Mass spectrum (FAB): m/z 1094 (M+H)$^+$; (3) Specific rotation: $[\alpha]_D^{22}$ −122° (c 0.66, CHCl$_3$); (4) $^1$H NMR spectrum (300 MHz, CDCl$_3$) δ (ppm): 1.01 (d, 16-H), 1.03 (d, 19-H), 1.10 (s, 3"-CH$_3$), 1.11 (d, 6"-H), 1.16 (t, 4"-OCOCH$_2$CH$_3$), 1.29 (d, 6'-H), 1.70 (dt, 14-H), 1.82 (m, 8-H), 1.84 (dd, 2"-Hax), 1.99 (d, 2"-Heq), 1.99 (s, 2'-OCOCH$_3$), 2.25 (br d, 2-H), 2.28 (br d, 14-H), 2.38 (s, 3'-N(CH$_3$)$_2$), 2.41 (q, 4"-OCOCH$_2$CH$_3$), 2.42 (q, 4"-OCOCH$_2$CH$_3$), 2.69 (t, 3'-H), 2.98 (dd, 2-H), 3.29 (s, 18-OCH$_3$), 3.35 (s, 18-OCH$_3$), 3.39 (s, 4-OCH$_3$), 3.51 (br d, 5-H), 3.62 (dd, 4-H), 3.87 (s, 3-OCOC$_6$H$_4$OCH$_3$), 4.24 (dd, 9-H), 4.38 (dq, 5"-H), 4.57 (dd, 18-H), 4.60 (d, 4"-H), 4.73 (d, 1'-H), 4.97 (dd, 2'-H), 5.03 (br d, 3-H), 5.03 (m, 15-H), 5.07 (d, 1"-H), 5.39 (ddd, 13-H), 5.92 (br dd, 12-H), 5.98 (dd, 10-H), 6.08 (dd, 11-H), 6.94 (d, 3-OCOC$_6$H$_4$OCH$_3$), 8.07 (d, 3-OCOC$_6$H$_4$OCH$_3$).

Example 50

Preparation of 3-Epi-3-O-(4-methoxybenzoyl) leucomycin A$_7$ (Compound Represented by Formula (II) Wherein R$^1$ Represents Hydrogen Atom, R$^2$ Represents Propionyl Group and R$^\beta$ Represents 4-Methoxybenzoyl Group)

64.0 mg of the compound of Example 49 was added with 4.0 ml of methanol:water (9:1) and reacted at 50° C. for 2 days. The reaction mixture was concentrated under reduced pressure, and the resulting residue was purified by silica gel column chromatography (hexane:ethyl acetate (2:1)) to obtain 55.2 mg of a compound. 57.2 mg of this compound was added with 10 ml of acetonitrile and dissolved, further added with 9.0 ml of water and 17.5 µl of difluoroacetic acid, and then the mixture was stirred at room temperature for 3 days. The reaction mixture was added with 20 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (200:10:1)) to obtain 32.0 mg of a compound.

Physicochemical Properties of the Compound (1) Molecular formula: $C_{46}H_{69}NO_{16}$; (2) Mass spectrum (TSP): m/z 892 (M+H)$^+$; (3) Specific rotation: $[\alpha]_D^{21}$ −93° (c 0.53, CHCl$_3$); (4) $^1$H NMR spectrum (300 MHz, CDCl$_3$) δ (ppm): 1.01 (d, 16-H), 1.09 (s, 3"-CH$_3$), 1.11 (d, 19-H), 1.11 (d, 6"-H), 1.15 (t, 4"-OCOCH$_2$CH$_3$), 1.21 (d, 6'-H), 1.28 (ddd, 7-H), 1.70 (ddd, 7-H), 1.81 (dd, 2"-Hax), 1.88 (dt, 14-H), 1.98 (d, 2"-Heq) 2.21 (m, 6-H), 2.41 (q, 4"-OCOCH$_2$CH$_3$), 2.42 (q, 4"-OCOCH$_2$CH$_3$), 2.47 (s, 3'-N (CH$_3$)$_2$), 2.60 (br d, 2-H), 3.00 (dd, 2-H), 3.02 (dd, 17-H), 3.41 (s, 4-OCH$_3$), 3.51 (br d, 4-H), 3.52 (dd, 2'-H), 3.80 (br d, 5-H), 3.86 (s, 3-OCOC$_6$H$_4$OCH$_3$), 4.16 (m, 9-H), 4.29 (d, 1'-H), 4.45 (dq, 5"-H), 4.59 (d, 4"-H), 4.98 (ddq, 15-H), 5.05 (d, 1"-H), 5.16 (br d, 3-H), 5.45 (ddd, 13-H), 5.80 (dd, 10-H), 5.97 (br dd, 12-H), 6.28 (dd, 11-H), 6.93 (d, 3-OCOC$_6$H$_4$OCH$_3$), 8.04 (d, 3-OCOC$_6$H$_4$OCH$_3$), 9.76 (br s, 18-H).

Example 51

Preparation of 3-Epi-2'-O-acetyl-9-O-tertbutyldimethylsilyl-3-O-(4-nitrobenzoyl) leucomycin A$_7$ 18-Dimethylacetal (Compound Represented by Formula (XIII) Wherein R$^1$ Represents Hydrogen Atom, R$^2$ Represents Propionyl Group and R$^8$ Represents 4-Nitrobenzoyl Group)

70.4 mg of the compound of Example 43 was added with 1.5 ml of dichloromethane and dissolved, further added with 134 µl of pyridine, 128 ml of 4-nitrobenzoyl chloride and 9.2 mg of 4-dimethylaminopyridine, and then the mixture was reacted at room temperature for 4 days. The reaction mixture was added with 20 ml of water and extracted with 50 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (3:1)) to obtain 69.2 mg of a compound.

Physicochemical Properties of the Compound (1) Molecular formula: $C_{55}H_{88}N_2O_{19}Si$; (2) Mass spectrum (FAB): m/z 1109 (M+H)$^+$; (3) Specific rotation: $[\alpha]_D^{22}$ −132° (c 0.52, CHCl$_3$); (4) $^1$H NMR spectrum (300 MHz, CDCl$_3$) δ (ppm): 0.98 (d, 16-H), 1.03 (d, 19-H), 1.10 (s, 3"-CH$_3$), 1.11 (d, 6"-H), 1.16 (t, 4"-OCOCH$_2$CH$_3$), 1.29 (d, 6'-H), 1.57 (dd, 17-H), 1.67 (dt, 14-H), 1.83 (m, 8-H), 1.84 (dd, 2"-Hax), 1.98 (d, 2"-Heq), 1.99 (s, 2'-OCOCH$_3$), 2.32 (br d, 2-H), 2.38 (s, 3'-N(CH$_3$)$_2$), 2.41 (q, 4"-OCOCH$_2$CH$_3$), 2.43 (q, 4"-OCOCH$_2$CH$_3$), 2.69 (t, 3'-H), 3.03 (dd, 2-H), 3.29 (s, 18-OCH$_3$), 3.35 (s, 18-OCH$_3$), 3.38 (s, 4-OCH$_3$), 3.53 (br d, 5-H), 3.59 (dd, 4-H), 4.24 (dd, 9-H), 4.38 (dq, 5"-H), 4.56 (dd, 18-H), 4.60 (d, 4"-H), 4.71 (d, 1'-H), 4.97 (dd, 2'-H), 5.07 (m, 15-H), 5.07 (d, 1"-H), 5.12 (br d, 3-H), 5.39 (ddd, 13-H), 5.89 (br dd, 12-H), 5.95 (dd, 10-H), 6.10 (dd, 11-H), 8.29 (d, 3-OCOC$_6$H$_4$NO$_2$), 8.34 (d, 3-OCOC$_6$H$_4$NO$_2$).

Example 52

Preparation of 3-Epi-3-O-(4-nitrobenzoyl) leucomycin A$_7$ (Compound Represented by Formula (II) Wherein R$^1$ Represents Hydrogen Atom, R$^2$ Represents Propionyl Group and R$^\beta$ Represents 4-Nitrobenzoyl Group)

61.9 mg of the compound of Example 51 was added with 4.0 ml of methanol:water (9:1) and reacted at 50° C. for 2 days. The reaction mixture was concentrated under reduced pressure, and the resulting residue was purified by silica gel column chromatography (chloroform:methanol (100:1)) to obtain 53.8 mg of a compound. 53.3 mg of this compound was added with 10 ml of acetonitrile and dissolved, further added with 8.0 ml of water and 16.0 µl of difluoroacetic acid, and then the mixture was stirred at room temperature for 3 days. The reaction mixture was added with 20 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (200:15:1)) to obtain 25.7 mg of a compound.

Physicochemical Properties of the Compound (1) Molecular formula: $C_{45}H_{66}N_2O_{17}$; (2) Mass spectrum (TSP): m/z 907 (M+H)$^+$; (3) Specific rotation: $[\alpha]_D^{21}$ −109° (c 0.57, CHCl$_3$); (4) $^1$H NMR spectrum (300 MHz, CDCl$_3$) δ (ppm): 0.99 (d, 16-H), 1.09 (s, 3"-CH$_3$), 1.11 (d, 19-H), 1.11 (d, 6"-H), 1.16 (t, 4"-OCOCH$_2$CH$_3$), 1.21 (d, 6'-H), 1.34 (ddd, 7-H), 1.60 (ddd, 7-H), 1.82 (dd, 2"-Hax), 1.98 (d, 2"-Heq) 2.15 (m, 6-H), 2.41 (q, 4"-OCOCH$_2$CH$_3$), 2.43 (q, 4"-OCOCH$_2$CH$_3$), 2.47 (s, 3'-N(CH$_3$)$_2$), 2.66 (br d, 2-H), 3.02 (dd, 17-H), 3.07 (dd, 2-H), 3.40 (s, 4-OCH$_3$), 3.50 (dd, 2'-H), 3.55 (br d, 4-H), 3.77 (br d, 5-H), 4.12 (br dd, 9-H), 4.32 (d, 1'-H), 4.44 (dq, 5"-H), 4.59 (d, 4"-H), 5.03 (ddq, 15-H), 5.04 (d, 1"-H), 5.23 (br d, 3-H), 5.47 (ddd, 13-H), 5.86 (dd, 10-H), 5.94 (br dd, 12-H), 6.26 (dd, 11-H), 8.28 (d, 3-OCOC$_6$H$_4$NO$_2$), 8.33 (d, 3-OCOC$_6$H$_4$NO$_2$), 9.74 (br s, 18-H).

Example 53

Preparation of 3-Epi-2'-O-acetyl-9-O-tert-butyldimethylsilyl-3-O-(pyridin-4-yl)carbonylleucomycin A₇ 18-Dimethylacetal (Compound Represented by Formula (XIII) Wherein $R^1$ Represents Hydrogen Atom, $R^2$ Represents Propionyl Group and $R^8$ Represents Pyridin-4-ylcarbonyl Group)

73.4 mg of the compound of Example 43 was added with 2.2 ml of dichloromethane and dissolved, further added with 500 μl of triethylamine, 188 mg of pyridin-4-ylcarbonyl chloride and 30.7 mg of 4-dimethylaminopyridine, and then the mixture was reacted at room temperature for 3 days. The reaction mixture was added with 20 ml of water and extracted with 50 ml of chloroform. The organic layer was washed with saturated aqueous sodium hydrogencarbonate and saturated brine, dried over anhydrous sodium sulfate and filtered. The filtrate was concentrated under reduced pressure, and the resulting residue was purified by silica gel column chromatography (chloroform:methanol:aqueous ammonia (1000:3:0.3)) to obtain 55.5 mg of a compound.

Physicochemical Properties of the Compound (1) Molecular formula: $C_{54}H_{88}N_2O_{17}Si$; (2) Mass spectrum (FAB): m/z 1065 (M+H)⁺; (3) Specific rotation: $[\alpha]_D^{22}$ −128° (c 0.63, CHCl₃); (4) ¹H NMR spectrum (300 MHz, CDCl₃) δ (ppm): 0.98 (d, 16-H), 1.03 (d, 19-H), 1.10 (s, 3"-CH₃), 1.11 (d, 6"-H), 1.16 (t, 4"-OCOCH₂CH₃), 1.28 (d, 6'-H), 1.58 (dd, 17-H), 1.69 (dt, 14-H), 1.82 (m, 8-H), 1.83 (dd, 2"-Hax), 1.99 (d, 2"-Heq), 1.99 (s, 2'-OCOCH₃), 2.30 (br d, 2-H), 2.32 (br d, 14-H), 2.38 (s, 3'-N(CH₃)₂), 2.41 (q, 4"-OCOCH₂CH₃), 2.43 (q, 4"-OCOCH₂CH₃), 2.69 (t, 3'-H), 3.01 (dd, 2-H), 3.29 (s, 18-OCH₃), 3.35 (s, 18-OCH₃), 3.38 (s, 4-OCH₃), 3.52 (br d, 5-H), 3.57 (dd, 4-H), 4.24 (dd, 9-H), 4.38 (dq, 5"-H), 4.56 (dd, 18-H), 4.60 (d, 4"-H), 4.72 (d, 1'-H), 4.97 (dd, 2'-H), 5.07 (m, 15-H), 5.07 (d, 1"-H), 5.11 (br d, 3-H), 5.39 (ddd, 13-H), 5.89 (br dd, 12-H), 5.95 (dd, 10-H), 6.09 (dd, 11-H), 7.92 (dd, 3-OCO-pyridine), 8.82 (dd, 3-OCO-pyridine).

Example 54

Preparation of 3-Epi-3-O-(pyridin-4-yl)carbonylleucomycin A₇ (Compound Represented by Formula (II) Wherein $R^1$ Represents Hydrogen Atom, $R^2$ Represents Propionyl Group and $R^\beta$ Represents Pyridin-4-ylcarbonyl Group)

67.5 mg of the compound of Example 53 was added with 5.0 ml of methanol:water (9:1) and reacted at room temperature for 4 days. The reaction mixture was concentrated under reduced pressure, and the resulting residue was purified by silica gel column chromatography (chloroform:methanol (500:1→100:1→20:1)) to obtain 60.0 mg of a compound. 60.2 mg of this compound was added with 10 ml of acetonitrile and dissolved, further added with 10 ml of water and 19.5 μl of difluoroacetic acid, and then the mixture was stirred at room temperature for 3 days. The reaction mixture was added with 20 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (200:15:1)) to obtain 32.7 mg of a compound.

Physicochemical Properties of the Compound (1) Molecular formula: $C_{44}H_{66}N_2O_{15}$; (2) Mass spectrum (TSP): m/z 863 (M+H)⁺; (3) Specific rotation: $[\alpha]_D^{21}$ −106° (c 0.57, CHCl₃); (4) ¹H NMR spectrum (300 MHz, CDCl₃) δ (ppm): 0.98 (d, 16-H), 1.09 (s, 3"-CH₃), 1.10 (d, 19-H), 1.11 (d, 6"-H), 1.15 (t, 4"-OCOCH₂CH₃), 1.20 (d, 6'-H), 1.36 (ddd, 7-H), 1.59 (ddd, 7-H), 1.82 (dd, 2"-Hax), 1.97 (d, 2"-Heq) 2.13 (m, 6-H), 2.41 (q, 4"-OCOCH₂CH₃), 2.42 (q, 4"-OCOCH₂CH₃), 2.47 (s, 3'-N(CH₃)₂), 2.64 (br d, 2-H), 3.01 (dd, 17-H), 3.05 (dd, 2-H), 3.40 (s, 4-OCH₃), 3.50 (dd, 2'-H), 3.54 (br d, 4-H), 3.72 (br d, 5-H), 4.11 (br dd, 9-H), 4.31 (d, 1'-H), 4.44 (dq, 5"-H), 4.59 (d, 4"-H), 5.02 (ddq, 15-H), 5.04 (d, 1"-H), 5.21 (br d, 3-H), 5.46 (ddd, 13-H), 5.85 (dd, 10-H), 5.94 (br dd, 12-H), 6.25 (dd, 11-H), 7.90 (dd, 3-OCO-pyridine), 8.81 (dd, 3-OCO-pyridine), 9.73 (br s, 18-H).

Example 55

Preparation of 3-Epi-2'-O-acetyl-9-O-tert-butyldimethylsilyl-3-O-(3-phenylpropionyl)leucomycin A₇ 18-Dimethylacetal (Compound Represented by Formula (XIII) Wherein $R^1$ Represents Hydrogen Atom, $R^2$ Represents Propionyl Group and $R^8$ Represents 3-Phenylpropionyl Group)

67.6 mg of the compound of Example 43 was added with 1.0 ml of dichloromethane and dissolved, further added with 90.0 μl of pyridine, 58.0 μl of 3-phenylpropionyl chloride and 10.2 mg of 4-dimethylaminopyridine, and then the mixture was reacted at room temperature for 4 hours. The reaction mixture was added with 20 ml of saturated aqueous sodium hydrogencarbonate and extracted with 50 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (3:1→2:1)) to obtain 59.3 mg of a compound.

Physicochemical Properties of the Compound (1) Molecular formula: $C_{57}H_{93}NO_{17}Si$; (2) Mass spectrum (FAB): m/z 1092 (M+H)⁺; (3) Specific rotation: $[\alpha]_D^{22}$ −101° (c 0.36, CHCl₃); (4) ¹H NMR spectrum (300 MHz, CDCl₃) δ (ppm): 1.00 (d, 19-H), 1.00 (s, 3"-CH₃), 1.11 (d, 6"-H), 1.16 (t, 4"-OCOCH₂CH₃), 1.17 (d, 16-H), 1.27 (d, 6'-H), 1.51 (m, 17-H), 1.73 (dt, 14-H), 1.82 (dd, 2"-Hax), 1.97 (d, 2"-Heq), 2.01 (s, 2'-OCOCH₃), 2.17 (br d, 2-H), 2.32 (br d, 14-H), 2.38 (s, 3'-N(CH₃)₂), 2.41 (q, 4"-OCOCH₂CH₃), 2.42 (q, 4"-OCOCH₂CH₃), 2.66 (t, 3-OCOCH₂CH₂C₆H₅), 2.68 (t, 3'-H), 2.79 (dd, 2-H), 3.00 (t, 3-OCOCH₂CH₂C₆H₅), 3.27 (s, 18-OCH₃), 3.29 (s, 18-OCH₃), 3.32 (s, 4-OCH₃), 3.35 (dd, 4-H), 3.44 (br d, 5-H), 4.21 (dd, 9-H), 4.38 (dq, 5"-H), 4.51 (dd, 18-H), 4.60 (d, 4"-H), 4.66 (d, 1'-H), 4.85 (br d, 3-H), 4.95 (dd, 2'-H), 5.03 (m, 15-H), 5.06 (d, 1"-H), 5.36 (ddd, 13-H), 5.84 (br dd, 12-H), 5.90 (dd, 10-H), 6.04 (dd, 11-H), 7.19 (m, 3-OCOCH₂CH₂C₆H₅), 7.26 (m, 3-OCOCH₂CH₂C₆H₅).

Example 56

Preparation of 3-Epi-3-O-(3-phenylpropionyl)leucomycin A₇ (Compound Represented by Formula (II) Wherein $R^1$ Represents Hydrogen Atom, $R^2$ Represents Propionyl Group and $R^\beta$ Represents 3-Phenylpropionyl Group)

52.2 mg of the compound of Example 55 was added with 3.0 ml of methanol:water (9:1) and reacted at room temperature for 2 days and then overnight at 45° C. The reaction mixture was concentrated under reduced pressure, and the resulting residue was purified by preparative TLC (chloroform:methanol (400:10:1)) to obtain 45.6 mg of a compound. 44.1 mg of the resulting compound was added with 7.0 ml of acetonitrile and dissolved, further added with 7.0 ml of water and 13.0 µl of difluoroacetic acid, and then the mixture was stirred at room temperature for 2 days. The reaction mixture was added with 15 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (200:10:1)) to obtain 13.3 mg of a compound.

Physicochemical Properties of the Compound (1) Molecular formula: $C_{47}H_{71}NO_{15}$; (2) Mass spectrum (FAB): m/z 890 (M+H)$^+$; (3) Specific rotation: $[\alpha]_D^{21}$ −119° (c 0.67, CHCl$_3$); (4) $^1$H NMR spectrum (300 MHz, CDCl$_3$) δ (ppm): 1.09 (d, 19-H), 1.10 (s, 3"-CH$_3$), 1.11 (d, 6"-H), 1.16 (d, 16-H), 1.16 (t, 4"-OCOCH$_2$CH$_3$), 1.20 (d, 6'-H), 1.25 (m, 7-H), 1.53 (ddd, 7-H), 1.78 (m, 8-H), 1.82 (dd, 2"-Hax), 1.98 (d, 2"-Heq), 2.14 (m, 6-H), 2.42 (q, 4"-OCOCH$_2$CH$_3$), 2.43 (q, 4"-OCOCH$_2$CH$_3$), 2.48 (s, 3'-N(CH$_3$)$_2$), 2.66 (t, 3-OCOCH$_2$CH$_2$C$_6$H$_5$), 2.80 (dd, 2-H), 2.98 (t, 3-OCOCH$_2$CH$_2$C$_6$H$_5$), 2.99 (dd, 17-H), 3.32 (s, 4-OCH$_3$), 3.44 (br d, 4-H), 3.50 (dd, 2'-H), 3.52 (br d, 5-H), 4.12 (m, 9-H), 4.24 (d, 1'-H), 4.45 (dq, 5"-H), 4.60 (d, 4"-H), 4.99 (br d, 3-H), 5.00 (ddq, 15-H), 5.05 (d, 1"-H), 5.37 (ddd, 13-H), 5.76 (dd, 10-H), 5.90 (br dd, 12-H), 6.19 (dd, 11-H), 7.26 (m, 3-OCOCH$_2$CH$_2$C$_6$H$_5$), 9.73 (br s, 18-H).

Example 57

Preparation of 3-Epi-2'-O-acetyl-9-O-tert-butyldimethylsilyl-3-O-cyclohexylcarbonylleucomycin A$_7$ 18-Dimethylacetal (Compound Represented by Formula (XIII) Wherein R$^1$ Represents Hydrogen Atom, R$^2$ Represents Propionyl Group and R$^8$ Represents Cyclohexylcarbonyl Group)

47.7 mg of the compound of Example 43 was added with 1.0 ml of dichloromethane and dissolved, further added with 108 µl of pyridine, 82.0 µl of cyclohexanecarbonyl chloride and 7.6 mg of 4-dimethylaminopyridine, and then the mixture was reacted at room temperature for 2 days. The reaction mixture was added with 20 ml of saturated aqueous sodium hydrogencarbonate and extracted with 40 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (3:1)) to obtain 31.5 mg of a compound.

Physicochemical Properties of the Compound (1) Molecular formula: $C_{55}H_{95}NO_{17}Si$; (2) Mass spectrum (TSP): m/z 1070 (M+H)$^+$; (3) Specific rotation: $[\alpha]_D^{24}$ −100° (c 1.8, CHCl$_3$); (4) $^1$H NMR spectrum (300 MHz, CDCl$_3$) δ (ppm): 0.99 (d, 19-H), 1.10 (s, 3"-CH$_3$), 1.11 (d, 6"-H), 1.16 (t, 4"-OCOCH$_2$CH$_3$), 1.24 (d, 16-H), 1.28 (d, 6'-H), 1.49 (br q, 3-OCOC$_6$H$_{11}$), 1.50 (m, 17-H), 1.70 (m, 3-OCOC$_6$H$_{11}$), 1.81 (m, 3-OCOC$_6$H$_{11}$), 1.83 (dd, 2"-Hax), 2.00 (d, 2"-Heq), 2.02 (s, 2'-OCOCH$_3$), 2.20 (br d, 2-H), 2.31 (tt, 3-OCOC$_6$H$_{11}$), 2.38 (s, 3'-N(CH$_3$)$_2$), 2.42 (q, 4"-OCOCH$_2$CH$_3$), 2.43 (q, 4"-OCOCH$_2$CH$_3$), 2.69 (t, 3'-H), 2.81 (dd, 2-H), 3.27 (s, 18-OCH$_3$), 3.33 (s, 18-OCH$_3$), 3.41 (s, 4-OCH$_3$), 3.46 (br d, 5-H), 4.21 (dd, 9-H), 4.38 (dq, 5"-H), 4.51 (dd, 18-H), 4.61 (d, 4"-H), 4.67 (d, 1'-H), 4.81 (br d, 3-H), 4.96 (dd, 2'-H), 5.06 (d, 1"-H), 5.09 (ddq, 15-H), 5.41 (ddd, 13-H), 5.91 (br dd, 12-H), 5.91 (dd, 10-H), 6.04 (dd, 11-H).

Example 58

Preparation of 3-Epi-3-O-cyclohexylcarbonylleucomycin A$_7$ (Compound Represented by Formula (II) Wherein R$^1$ Represents Hydrogen Atom, R$^2$ Represents Propionyl Group and R$^\beta$ Represents Cyclohexylcarbonyl Group)

84.7 mg of the compound of Example 57 was added with 8.0 ml of methanol:water (9:1) and reacted overnight at 50° C. The reaction mixture was concentrated under reduced pressure, and the resulting residue was purified by silica gel column chromatography (hexane:ethyl acetate (1:1)) to obtain 41.0 mg of a compound. 60.3 mg of the resulting compound was added with 10 ml of acetonitrile and dissolved, further added with 10 ml of water and 19.0 µl of difluoroacetic acid, and then the mixture was stirred at room temperature for 2 days. The reaction mixture was added with 20 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol (10:1)) to obtain 27.3 mg of a compound.

Physicochemical Properties of the Compound (1) Molecular formula: $C_{45}H_{73}NO_{15}$; (2) Mass spectrum (FAB): m/z 868 (M+H)$^+$; (3) Specific rotation: $[\alpha]_D^{21}$ −87° (c 1.4, CHCl$_3$); (4) $^1$H NMR spectrum (300 MHz, CDCl$_3$) δ (ppm): 1.06 (d, 19-H), 1.10 (s, 3"-CH$_3$), 1.11 (d, 6"-H), 1.16 (t, 4"-OCOCH$_2$CH$_3$), 1.20 (d, 6'-H), 1.26 (d, 16-H), 1.49 (m, 3-OCOC$_6$H$_{11}$), 1.55 (ddd, 7-H), 1.68 (m, 3-OCOC$_6$H$_{11}$), 1.79 (m, 3-OCOC$_6$H$_{11}$), 1.81 (dd, 2"-Hax), 1.93 (m, 3-OCOC$_6$H$_{11}$), 1.98 (d, 2"-Heq), 2.09 (dt, 14-H), 2.16 (m, 6-H), 2.30 (tt, 3-OCOC$_6$H$_{11}$), 2.42 (q, 4"-OCOCH$_2$CH$_3$), 2.43 (q, 4"-OCOCH$_2$CH$_3$), 2.47 (s, 3'-N(CH$_3$)$_2$), 2.83 (dd, 2-H), 2.98 (dd, 17-H), 3.44 (s, 4-OCH$_3$), 3.48 (br d, 4-H), 3.50 (dd, 2'-H), 3.57 (br d, 5-H), 4.10 (br dd, 9-H), 4.24 (d, 1'-H), 4.45 (dq, 5"-H), 4.60 (d, 4"-H), 4.96 (br d, 3-H), 5.04 (ddq, 15-H), 5.05 (d, 1"-H), 5.52 (ddd, 13-H), 5.78 (dd, 10-H), 5.96 (br dd, 12-H), 6.20 (dd, 11-H), 9.73 (br s, 18-H).

Example 59

Preparation of 3-Epi-2'-O-acetyl-9-O-tert-butyldimethylsilyl-3-O-(6-phenylhexanoyl) leucomycin A$_7$ 18-Dimethylacetal (Compound Represented by Formula (XIII) Wherein R$^1$ Represents Hydrogen Atom, R$^2$ Represents Propionyl Group and R$^8$ Represents 6-Phenylhexanoyl Group)

102 mg of the compound of Example 43 was added with 1.5 ml of dichloromethane and dissolved, further added with 194.0 µl of pyridine, 140.0 µl of 6-phenylhexanoyl chloride and 16.5 mg of 4-dimethylaminopyridine, and then the mixture was reacted overnight at room temperature. The reaction mixture was added with 20 ml of saturated aqueous sodium hydrogencarbonate and extracted with 80 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (5:1→3:1→1:1)) to obtain 71.2 mg of a compound.

Physicochemical Properties of the Compound (1) Molecular formula: $C_{60}H_{99}NO_{17}Si$; (2) Mass spectrum (TSP): m/z 1134 (M+H)$^+$; (3) Specific rotation: $[\alpha]_D^{23}$ −87° (c 1.9, CHCl$_3$); (4) $^1$H NMR spectrum (300 MHz, CDCl$_3$) δ (ppm): 0.99 (d, 19-H), 1.10 (s, 3"-CH$_3$), 1.12 (d, 6"-H), 1.16 (t, 4"-OCOCH$_2$CH$_3$), 1.22 (d, 16-H), 1.28 (d, 6'-H), 1.67 (quint, 3-OCO(CH$_2$)$_5$C$_6$H$_5$), 1.83 (dd, 2"-Hax), 1.99 (d, 2"-Heq), 2.02 (s, 2'-OCOCH$_3$), 2.20 (br d, 2-H), 2.32 (t, 3-OCO(CH$_2$)$_5$C$_6$H$_5$), 2.39 (s, 3'-N(CH$_3$)$_2$), 2.42 (q, 4"-OCOCH$_2$CH$_3$), 2.43 (q, 4"-OCOCH$_2$CH$_3$), 2.63 (t, 3-OCO(CH$_2$)$_5$C$_6$H$_5$), 2.69 (t, 3'-H), 2.80 (dd, 2-H), 3.27 (s, 18-OCH$_3$), 3.33 (s, 18-OCH$_3$), 3.40 (s, 4-OCH$_3$), 3.46 (br d, 5-H), 4.21 (dd, 9-H), 4.39 (dq, 5"-H), 4.52 (dd, 18-H), 4.61 (d, 4"-H), 4.68 (d, 1'-H), 4.86 (br d, 3-H), 4.96 (dd, 2'-H), 5.06 (d, 1"-H), 5.08 (ddq, 15-H), 5.40 (ddd, 13-H), 5.90 (dd, 10-H),) 5.93 (br dd, 12-H), 6.06 (dd, 11-H), 7.15 (m, 3-OCO(CH$_2$)$_5$C$_6$H$_5$), 7.25 (m, 3-OCO(CH$_2$)$_5$C$_6$H$_5$).

Example 60

Preparation of 3-Epi-3-O-(6-phenylhexanoyl) leucomycin A$_7$ (Compound Represented by Formula (II) Wherein R$^1$ Represents Hydrogen Atom, R$^2$ Represents Propionyl Group and R$^β$ Represents 6-Phenylhexanoyl Group)

4.5 ml of methanol:water (9:1) was added with 76.5 mg of the compound of Example 59, and then the mixture was reacted at 50° C. for 2 days. The reaction mixture was concentrated under reduced pressure, and the resulting residue was purified by silica gel column chromatography (chloroform:methanol (200:1→100:1→10:1)) to obtain 72.1 mg of a compound. 68.1 mg of this compound was added with 10 ml of acetonitrile and dissolved, further added with 10 ml of water and 19.6 μl of difluoroacetic acid, and then the mixture was stirred at room temperature for 2 days. The reaction mixture was added with 20 ml of saturated aqueous sodium hydrogencarbonate and extracted with 60 ml of chloroform. The organic layer was washed with 30 ml of saturated brine, dried over anhydrous sodium sulfate and filtered. The filtrate was concentrated under reduced pressure, and the resulting residue was purified by preparative TLC (chloroform:methanol:aqueous ammonia (100:10:1)) to obtain 27.2 mg of a compound.
Physicochemical Properties of the Compound (1) Molecular formula: C$_{50}$H$_{77}$NO$_{15}$; (2) Mass spectrum (TSP): m/z 932 (M+H)$^+$; (3) Specific rotation: [α]$_D^{24}$ −92° (c 1.2, CHCl$_3$); (4) $^1$H NMR spectrum (300 MHz, CDCl$_3$) δ (ppm): 1.06 (d, 19-H), 1.09 (s, 3"-CH$_3$), 1.11 (d, 6"-H), 1.16 (t, 4"-OCOCH$_2$CH$_3$), 1.20 (d, 6'-H), 1.23 (d, 16-H), 1.39 (m, 3-OCO(CH$_2$)$_5$C$_6$H$_5$), 1.52 (ddd, 7-H), 1.65 (quint, 3-OCO(CH$_2$)$_5$C$_6$H$_5$), 1.67 (quint, 3-OCO(CH$_2$)$_5$C$_6$H$_5$), 1.78 (m, 8-H), 1.81 (dd, 2"-Hax), 1.98 (d, 2"-Heq), 2.07 (dt, 14-H), 2.31 (t, 3-OCO(CH$_2$)$_5$C$_6$H$_5$), 2.42 (q, 4"-OCOCH$_2$CH$_3$), 2.43 (q, 4"-OCOCH$_2$CH$_3$), 2.48 (s, 3'-N(CH$_3$)$_2$), 2.61 (t, 3-OCO(CH$_2$)$_5$C$_6$H$_5$), 2.81 (dd, 2-H), 2.99 (dd, 17-H), 3.41 (s, 4-OCH$_3$), 3.51 (dd, 2'-H), 4.10 (br t, 9-H), 4.27 (d, 1'-H), 4.45 (dq, 5"-H), 4.59 (d, 4"-H), 5.00 (br d, 3-H), 5.02 (m, 15-H), 5.05 (d, 1"-H), 5.52 (ddd, 13-H), 5.76 (dd, 10-H), 5.97 (br dd, 12-H), 6.22 (dd, 11-H), 7.16 (m, 3-OCO(CH$_2$)$_5$C$_6$H$_5$), 7.26 (m, 3-OCO(CH$_2$)$_5$C$_6$H$_5$), 9.72 (br s, 18-H).

Example 61

Preparation of 3-Epi-2'-O-acetyl-9-O-tert-butyldimethylsilyl-3-O-(quinolin-2-yl) carbonylleucomycin A$_7$ 18-Dimethylacetal (Compound Represented by Formula (XIII) Wherein R$^1$ Represents Hydrogen Atom, R$^2$ Represents Propionyl Group and R$^8$ Represents Quinolin-2-ylcarbonyl Group)

104 mg of the compound of Example 43 was added with 1.5 ml of dichloromethane and dissolved, further added with 599 μl of triethylamine, 264 mg of quinolin-2-ylcarbonyl chloride and 51.0 mg of 4-dimethylaminopyridine, and then the mixture was reacted at room temperature for 3 days. The reaction mixture was added with 30 ml of saturated aqueous sodium hydrogencarbonate and extracted with 80 ml of chloroform. The organic layer was washed with saturated brine, dried over anhydrous sodium sulfate and filtered. The filtrate was concentrated under reduced pressure, and the resulting residue was purified by silica gel column chromatography (hexane:ethyl acetate (4:1→3:1→2:1)) to obtain 71.2 mg of a compound.
Physicochemical Properties of the Compound (1) Molecular formula: C$_{58}$H$_{90}$N$_2$O$_{17}$Si; (2) Mass spectrum (FAB): m/z 1115 (M+H)$^+$; (3) Specific rotation: [α]$_D^{24}$ −136° (c 0.62, CHCl$_3$); (4) $^1$H NMR spectrum (300 MHz, CDCl$_3$) δ (ppm): 1.02 (d, 19-H), 1.04 (d, 16-H), 1.10 (s, 3"-CH$_3$), 1.11 (d, 6"-H), 1.15 (t, 4"-OCOCH$_2$CH$_3$), 1.30 (d, 6'-H), 1.56 (m, 17-H), 1.78 (m, 14-H), 1.83 (dd, 2"-Hax), 1.84 (m, 8-H), 1.98 (d, 2"-Heq), 1.98 (s, 2'-OCOCH$_3$), 2.30 (br d, 14-H), 2.33 (br d, 2-H), 2.37 (s, 3'-N(CH$_3$)$_2$), 2.41 (q, 4"-OCOCH$_2$CH$_3$), 2.42 (q, 4"-OCOCH$_2$CH$_3$), 2.67 (t, 3'-H), 3.12 (dd, 2-H), 3.30 (s, 18-OCH$_3$), 3.37 (s, 18-OCH$_3$), 3.40 (s, 4-OCH$_3$), 3.57 (br d, 5-H), 3.68 (dd, 4-H), 4.25 (dd, 9-H), 4.38 (dq, 5"-H), 4.59 (m, 18-H), 4.60 (d, 4"-H), 4.74 (d, 1'-H), 4.97 (dd, 2'-H), 5.07 (d, 1"-H), 5.12 (ddq, 15-H), 5.25 (br d, 3-H), 5.42 (ddd, 13-H), 6.06 (br dd, 12-H), 6.07 (dd, 10-H), 6.12 (dd, 11-H), 7.67 (ddd, 3-OCO-quinoline), 7.81 (ddd, 3-OCO-quinoline), 7.90 (br d, 3-OCO-quinoline), 8.20 (d, 3-OCO-quinoline), 8.33 (d, 3-OCO-quinoline), 8.37 (br d, 3-OCO-quinoline).

Example 62

Preparation of 3-Epi-3-O-(quinolin-2-yl) carbonylleucomycin A$_7$ (Compound Represented by Formula (II) Wherein R$^1$ Represents Hydrogen Atom, R$^2$ Represents Propionyl Group and R$^β$ Represents Quinolin-2-ylcarbonyl Group)

68.7 mg of the compound of Example 61 was added with 3.0 ml of methanol:water (9:1) and reacted at 45° C. for 2 days. The reaction mixture was concentrated under reduced pressure, and the resulting residue was purified by silica gel column chromatography (hexane:ethyl acetate (1:1)) to obtain 56.3 mg of a compound. 53.1 mg of this compound was added with 8.0 ml of acetonitrile and dissolved, further added with 8.0 ml of water and 18.5 μl of difluoroacetic acid and stirred at room temperature for 3 days. The reaction mixture was added with 20 ml of saturated aqueous sodium hydrogencarbonate and extracted with 50 ml of chloroform. The organic layer was washed with 20 ml of saturated brine, dried over anhydrous sodium sulfate and filtered. The filtrate was concentrated under reduced pressure, and the resulting residue was purified by preparative TLC (chloroform:methanol:aqueous ammonia (100:10:1)) to obtain 24.0 mg of a compound.
Physicochemical Properties of the Compound (1) Molecular formula: C$_{48}$H$_{68}$N$_2$O$_{15}$; (2) Mass spectrum (TSP): m/z 913 (M+H)$^+$; (3) Specific rotation: [α]$_D^{23}$ −132° (c 0.27, CHCl$_3$); (4) $^1$H NMR spectrum (300 MHz, CDCl$_3$) δ (ppm): 1.09 (d, 19-H), 1.10 (s, 3"-CH$_3$), 1.11 (d, 16-H), 1.11 (d, 6"-H), 1.16 (t, 4"-OCOCH$_2$CH$_3$), 1.21 (d, 6'-H), 1.33 (m, 7-H), 1.82 (dd, 2"-Hax), 1.84 (m, 8-H), 1.96 (m, 14-H), 1.98 (d, 2"-Heq), 2.23 (m, 6-H), 2.37 (br d, 14-H), 2.42 (q, 4"-OCOCH$_2$CH$_3$), 2.43 (q, 4"-OCOCH$_2$CH$_3$), 2.49 (s, 3'-N(CH$_3$)$_2$), 2.67 (br d, 2-H), 2.99 (dd, 17-H), 3.11 (dd, 2-H), 3.42 (s, 4-OCH$_3$), 3.53 (dd, 2'-H), 3.66 (br d, 5-H), 3.78 (br d, 4-H), 4.09 (dd, 9-H), 4.33 (d, 1'-H), 4.45 (dq, 5"-H), 4.60 (d, 4"-H), 5.00 (m, 15-H), 5.05 (d, 1"-H), 5.35 (br d, 3-H), 5.53 (ddd, 13-H), 5.94 (dd, 10-H), 6.14 (br dd, 12-H), 6.30 (dd, 11-H), 7.67 (ddd, 3-OCO-quinoline), 7.80 (ddd, 3-OCO-quinoline), 7.90 (br d, 3-OCO-quinoline), 8.19 (d, 3-OCO-quinoline), 8.32 (d, 3-OCO-quinoline), 8.41 (br d, 3-OCO-quinoline), 9.75 (br s, 18-H).

Test Example 1

Antibacterial Activity Test

In vitro antibacterial activities of the compounds of Examples 3, 5, 20, 23, 25 and 48 were determined as follows by referring to the standard method of the Japanese Society of Chemotherapy (Chemotherapy, 29, pp.76–79, 1981). For comparison, antibacterial activities of rokitamycin (RKM), leucomycin-$A_7$ (LM-$A_7$) and the compound described in U.S. Pat. No. 5,407,918, Example 7 were determined in the same manner.

For a solution of each test drug dissolved in methanol at 5000 μg/ml, a series of 2-fold dilutions were prepared. 200 μl of each solution of the test drug was added in a petri dish, added with 10 ml of agar medium for susceptibility measurement supplemented with 5% of sterile horse defibrinated blood, 15 μg/ml of β-nicotinamide adenine dinucleotide and 5 μg/ml of Hemin, and then mixed to prepare agar plates containing the test drug. A given volume of a culture broth for susceptibility measurement, which was prepared to contain a given cell numbers of bacteria to be tested, was inoculated to the agar plates containing the test drug by using a micro planter (Sakuma Seisakusho). After the inoculation, cultivation was carried out at 37° C. for about 20 hours. After the culture, presence or absence of the growth of the test bacteria on the plates was observed by visual inspection, and the minimum concentration at which no growth was observed was determined as minimum inhibitory concentration (MIC) of each test drug for each of the test bacteria The results are shown in Tables 1-1, 1-2 and 1-3.

TABLE 1-1

Minimum inhibitory concentration (MIC, μg/ml)

| Test bacterial strain | Compound of Example 3 | Compound of Example 5 | RKM |
|---|---|---|---|
| Staphylococcus aureus 209P JC-1 | 0.10 | 0.20 | 0.20 |
| Staphylococcus aureus MS15027 (ermC methylase) | 0.20 | 0.39 | 0.39 |
| Micrococcus luteus ATCC9341 | 0.025 | 0.10 | 0.05 |
| Streptococcus pneumoniae DP1 TypeI | 0.05 | 0.20 | 0.10 |
| Streptococcus pneumoniae PRC-53 (mefE efflux) | 0.10 | 0.20 | 0.20 |
| Streptococcus pyogenes Cook | 0.025 | 0.10 | 0.05 |
| Moraxella catarrhalis W-0500 | 0.20 | 0.39 | 0.20 |
| Haemophilus influenzae 9334 | 3.13 | 6.25 | 1.56 |

TABLE 1-2

Minimum inhibitory concentration (MIC, μg/ml)

| Test bacterial strain | Compound of Example 20 | Compound of US5407918 | Compound of Example 23 | LM-$A_7$ |
|---|---|---|---|---|
| Staphylococcus aureus 209P JC-1 | 0.20 | 0.20 | 0.20 | 0.39 |
| Staphylococcus aureus MS15027 (ermC methylase) | 0.39 | 0.39 | 0.20 | 0.39 |
| Micrococcus luteus ATCC9341 | 0.05 | 0.05 | 0.05 | 0.10 |
| Streptococcus pneumoniae DP1 TypeI | 0.10 | 0.10 | 0.10 | 0.20 |
| Streptococcus pneumoniae PRC-53 (mefE efflux) | 0.10 | 0.10 | 0.10 | 0.20 |
| Streptococcus pyogenes Cook | 0.10 | 0.05 | 0.10 | 0.10 |
| Moraxella catarrhalis W-0500 | 0.39 | 0.20 | 0.78 | 0.78 |
| Haemophilus influenzae 9334 | 1.56 | 1.56 | 1.56 | 1.56 |

Note:
The medium used was blood agar medium containing a medium for a disc for susceptibility test - N "Nissui" as a base medium.

TABLE 1-3

Minimum inhibitory concentration (MIC, μg/ml)

| Test bacterial strain | Compound of Example 25 | Compound of Example 48 | LM-$A_7$ |
|---|---|---|---|
| Staphylococcus aureus 209P JC-1 | 0.39 | 0.39 | 0.39 |
| Staphylococcus aureus MS15027 (ermC methylase) | 1.56 | 0.78 | 0.39 |
| Streptococcus pneumoniae IP692 | 0.39 | 0.20 | 0.39 |
| Streptococcus pneumoniae TH-662 (ermAM methylase) | >100 | 25 | >100 |
| Streptococcus pneumoniae PRC-91 (ermAM methylase) | >100 | 25 | >100 |
| Streptococcus pneumoniae PRC-53 (mefE efflux) | 0.39 | 0.20 | 0.20 |
| Moraxella catarrhalis W-0500 | 1.56 | 0.78 | 0.78 |
| Haemophilus influenzae 9334 | 6.25 | 6.25 | 1.56 |

The compounds of the present invention are demonstrated to have potent antibacterial activity against Gram-positive bacteria which are clinically important. In particular, the compound of Example 20 has almost the same antibacterial activity as that of the compound described in Example 7 of the U.S. Pat. No. 5,407,918, and as for the compounds of Examples 3 and 23, almost two-fold enhancement of the antibacterial activity was observed compared to RKM and LM-$A_7$. In addition, by comparison of the compound of Example 25 having the naturally occurring configuration and the compound of Example 48 having the reversed configuration at 3-position in the antibacterial activity tests mainly using resistant bacteria (types of resistance are indicated in the parentheses in the tables), the compound of Example 48 is revealed to have improvement in antibacterial activity against the resistant strains of Streptococcus pneumoniae causing problems recently, which indicates the fact that the derivatives with inversion of the configuration at the 3-position contribute to improvement of antibacterial activities.

Test Example 2

Plasma Stability Test

Stability of the compound of Example 3 in plasma was studied as follows. Stability of RKM in plasma was also studied in the same manner for comparison. Blood was collected from rat ventral aorta and centrifuged (3000 rpm, 15 minutes) to separate plasma. 10 μl of a solution of a test drug dissolved in methanol at a concentration of 1600 μg/ml was added to 190 μl of the rat plasma and reacted at 37° C. At the start of the reaction and after 1, 2 and 4 hours, a part of the reaction mixture was collected and added with a given volume of an acetonitrile solution to prepare a bioassay sample for measurement of test medicament concentration. A paper disc having a 8 mm diameter was impregnated with a given volume of the bioassay sample and placed on an agar plate which was prepared by suspending *Micrococcus luteus* ATCC9341 so as to contain given cell numbers of the bacteria, and the plate was incubated at 37° C. for about 20 hours. After the incubation, the diameter of the ring by growth inhibition of *Micrococcus luteus* ATCC9341 observed around the paper disc was measured by using a digital caliper. Further, standard solutions of the test drug prepared by diluting the drug with the rat plasma to known concentrations were treated in the same manner. Based on a calibration curve obtained from concentrations of the standard solutions and diameters of growth inhibition rings, concentrations of the test drug in the samples at several time points were calculated, and then, by using the calculated remaining concentrations of the test drug in the samples at the time points, ratios of activity (%) based on the concentration at the start of the reaction, which was taken as 100%, were calculated. The results are shown in FIG. 1. The compound of Example 3 was more stable in the rat plasma than RKM, and had a property that the antibacterial activity was maintained for a long time of period. Since only difference in chemical structure from RKM resides in the 3-position, it is apparent that the advantageous effects of the present invention are obtained by the alkylation of the hydroxyl group at the 3-position of leucomycins.

Industrial Applicability

The compounds of the present invention represented by the general formula (I) and (II) and pharmaceutically acceptable salts thereof are useful as active ingredients of medicaments for therapeutic and/or prophylactic treatment of infectious diseases such as those caused by Gram-positive bacteria. Further, the compounds of the present invention represented by the general formula (III) and (IV) and salts thereof are useful as synthetic intermediates for efficient preparation of the compounds represented by the aforementioned general formula (I) and (II) and pharmaceutically acceptable salt thereof.

What is claimed is:
1. A compound represented by the following formula (I) or a pharmaceutically acceptable salt thereof:

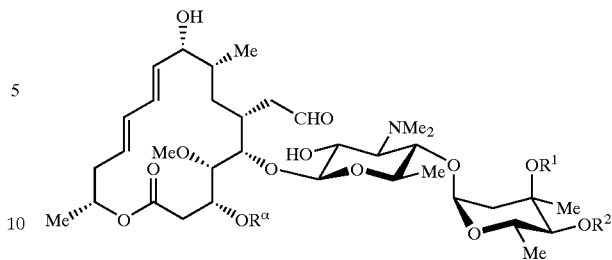

(I)

wherein $R^\alpha$ represents a C1–C10 alkyl group, a C3–C10 alkenyl group, a C7–C15 aralkyl group, a quinolinylalkyl group, a quinolinylalkenyl group, a C7–C15 aralkylcarbonyl group, a C4–C7 cycloalkylcarbonyl group, benzoyl group, an imidazolylcarbonyl group, a quinolinylcarbonyl group, an N-alkylaminocarbonyl group, an N,N-dialkylaminocarbonyl group, or an N-aralkylaminocarbonyl group; $R^1$ represents hydrogen atom, a C1–C10 alkyl group, or a C2–C10 alkylcarbonyl group; and $R^2$ represents hydrogen atom, a C1–C10 alkyl group or a C2–C10 alkylcarbonyl group.

2. The compound or a pharmaceutically acceptable salt thereof according to claim 1, wherein $R^\alpha$ represents a C1–C10 alkyl group, a C3–C10 alkenyl group, a quinolinylalkenyl group, a C7–C15 aralkylcarbonyl group, benzoyl group, an imidazolylcarbonyl group, a quinolinylcarbonyl group, a C4–C7 cycloalkylcarbonyl group, an N-alkylaminocarbonyl group, an N,N-dialkylaminocarbonyl group, or an N-aralkylaminocarbonyl group; $R^1$ represents hydrogen atom, a C1–C10 alkyl group, or a C2–C10 alkylcarbonyl group; and $R^2$ represents hydrogen atom, a C1–C10 alkyl group, or a C2–C10 alkylcarbonyl group.

3. The compound or a pharmaceutically acceptable salt thereof according to claim 1, wherein $R^\alpha$ represents a C1–C10 alkyl group, a C3–C10 alkenyl group, a quinolinylalkenyl group, an imidazolylcarbonyl group, an N-alkylaminocarbonyl group, an N,N-dialkylaminocarbonyl group, quinolinylcarbonyl group, or an N-aralkylaminocarbonyl group; $R^3$ represents a C2–C10 alkylcarbonyl group; and $R^2$ represents a C2–C10 alkylcarbonyl group.

4. The compound or a pharmaceutically acceptable salt thereof according to claim 1, wherein $R^\alpha$ represents a C1–C10 alkyl group; $R^1$ represents a C1–C10 alkyl group; and $R^2$ represents a C1–C10 alkyl group.

5. The compound or a pharmaceutically acceptable salt thereof according to claim 1, wherein $R^\alpha$ represents a C1–C10 alkyl group; $R^1$ represents hydrogen atom; and $R^2$ represents a C2–C10 alkylcarbonyl group.

6. A compound represented by the following formula (II) or a pharmaceutically acceptable salt thereof:

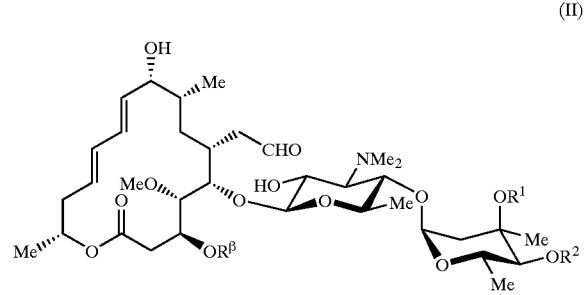

(II)

wherein R$^\beta$ represents hydrogen atom, a C2–C10 alkylcarbonyl group, a C4–C7 cycloalkylcarbonyl group, a C7–C15 aralkylcarbonyl group, benzoyl group, a 4-pyridinylcarbonyl group, a 2-quinolinylcarbonyl group, an N-alkylaminocarbonyl group, or an N-aralkylaminocarbonyl group; R$^1$ represents hydrogen atom, or a C2–C10 alkylcarbonyl group; and R$^2$ represents hydrogen atom, or a C2–C10 alkylcarbonyl group.

7. The compound or a pharmaceutically acceptable salt thereof according to claim 6, wherein R$^\beta$ represents hydrogen atom, a C2–C10 alkylcarbonyl group, a C4–C7 cycloalkylcarbonyl group, a C7–C15 aralkylcarbonyl group, benzoyl group, 2-quinolinylcarbonyl group, 4-pyridinylcarbonyl group; R$^1$ represents hydrogen atom; and R$^2$ represents a C2–C10 alkylcarbonyl group.

8. The compound or a pharmaceutically acceptable salt thereof according to claim 6, wherein R$^\beta$ represents hydrogen atom, benzoyl group, an N-alkylaminocarbonyl group, or an N-aralkylaminocarbonyl group; R$^1$ represents a C2–C10 alkylcarbonyl group; and R$^2$ represents a C2–C10 alkylcarbonyl group.

9. The compound or a pharmaceutically acceptable salt thereof according to claim 6, wherein R$^\beta$ represents hydrogen atom, a C2–C10 alkylcarbonyl group, benzoyl group, a C4–C7 cycloalkylcarbonyl group, a C7–C15 aralkylcarbonyl group, 2-quinolinylcarbonyl group, or 4-pyridinylcarbonyl group, R$^1$ represents hydrogen atom, and R$^2$ represents a C2–C10 alkylcarbonyl group.

10. A medicament in a form of pharmaceutical composition comprising one or more additives for pharmaceutical preparations together with the compound of claim 1 or a pharmaceutically acceptable salt thereof.

11. A method for therapeutic treatment of a bacterial infectious disease, which comprises the step of administering a therapeutically effective amount of the compound according to any one of the claims 1 to 9 or a pharmaceutically acceptable salt thereof to a mammal.

12. A compound represented by the following formula (III) or a pharmaceutically acceptable salt thereof:

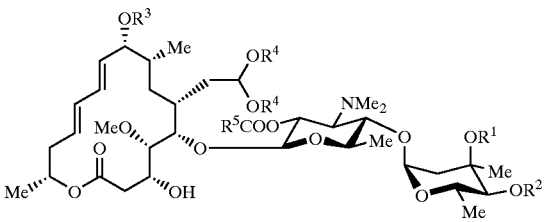

(III)

wherein R$^1$ represents hydrogen atom, a C1–C10 alkyl group or a C2–C10 alkylcarbonyl group; R$^2$ represents hydrogen atom, a C1–C10 alkyl group, or a C2–C10 alkylcarbonyl group; R$^3$ represents triethylsilyl group, triisopropylsilyl group, triphenylsilyl group, tribenzylsilyl group, dimethylisopropylsilyl group, t-butyldimethylsilyl group, or t-butyldiphenylsilyl group, R$^4$ represents a C1–C5 alkyl group, and R$^5$ represents a C1–C5 alkyl group.

13. A compound represented by the following formula (IV) or a pharmaceutically acceptable salt thereof:

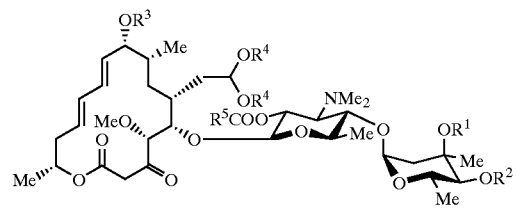

(IV)

wherein R$^1$ represents hydrogen atom, a C1–C10 alkyl group, or a C2–C10 alkylcarbonyl group; R$^2$ represents hydrogen atom, a C1–C10 alkyl group, or a C2–C10 alkylcarbonyl group; R$^3$ represents triethylsilyl group, triisopropylsilyl group, triphenylsilyl group, tribenzylsilyl group, dimethylisopropylsilyl group, t-butyldimethylsilyl group, or t-butyldiphenylsilyl group; R$^4$ represents a C1–C5 alkyl group; and R$^5$ represents a C1–C5 alkyl group.

* * * * *